US008067571B2

(12) United States Patent
Weller et al.

(10) Patent No.: US 8,067,571 B2
(45) Date of Patent: *Nov. 29, 2011

(54) ANTIBACTERIAL ANTISENSE OLIGONUCLEOTIDE AND METHOD

(75) Inventors: Dwight D. Weller, Corvallis, OR (US);
Bruce L. Geller, Corvallis, OR (US);
Patrick L. Iversen, Corvallis, OR (US);
Lucas D. Tilley, Burlington, VT (US);
Jed N. Hassinger, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 161 days.

This patent is subject to a terminal disclaimer.

(21) Appl. No.: 11/803,107

(22) Filed: May 11, 2007

(65) Prior Publication Data
US 2008/0194463 A1 Aug. 14, 2008

Related U.S. Application Data

(63) Continuation-in-part of application No. 11/487,009, filed on Jul. 13, 2006, now Pat. No. 7,790,694.

(60) Provisional application No. 60/699,280, filed on Jul. 13, 2005.

(51) Int. Cl.
*C07H 21/02* (2006.01)
*C07H 21/04* (2006.01)
*A61K 31/70* (2006.01)
*C12Q 1/68* (2006.01)

(52) U.S. Cl. ..... 536/24.5; 435/6.11; 435/375; 536/23.1; 536/24.1; 514/44 A

(58) Field of Classification Search ............... None
See application file for complete search history.

(56) References Cited

U.S. PATENT DOCUMENTS

| | | |
|---|---|---|
| 5,034,506 A | 7/1991 | Summerton et al. |
| 5,142,047 A | 8/1992 | Summerton et al. |
| 5,166,315 A | 11/1992 | Summerton et al. |
| 5,185,444 A | 2/1993 | Summerton et al. |
| 5,217,866 A | 6/1993 | Summerton et al. |
| 5,506,337 A | 4/1996 | Summerton et al. |
| 5,521,063 A | 5/1996 | Summerton et al. |
| 5,580,767 A | 12/1996 | Cowsert et al. |
| 5,698,685 A | 12/1997 | Summerton et al. |
| 5,892,023 A | 4/1999 | Pirotzky et al. ............... 536/24.5 |
| 6,060,456 A | 5/2000 | Arnold et al. |
| 6,133,246 A | 10/2000 | McKay et al. |
| 6,228,579 B1 | 5/2001 | Zyskind et al. |
| 6,239,265 B1 | 5/2001 | Cook |
| 6,365,351 B1 | 4/2002 | Iversen |
| 6,495,663 B1 | 12/2002 | Rothbard |
| 6,548,651 B1 | 4/2003 | Nielsen et al. |
| 6,677,153 B2 | 1/2004 | Iversen |
| 6,828,105 B2 | 12/2004 | Stein et al. |
| 6,841,542 B2 | 1/2005 | Bartelmez et al. |
| 7,049,431 B2 | 5/2006 | Iversen et al. |
| 7,094,765 B1 | 8/2006 | Iversen et al. |
| 7,625,873 B2 | 12/2009 | Geller et al. |
| 7,943,762 B2 | 5/2011 | Weller et al. |
| 2003/0224353 A1 | 12/2003 | Stein et al. |
| 2004/0110296 A1 | 6/2004 | Vargeese et al. |
| 2006/0148747 A1 | 7/2006 | Stein et al. |
| 2006/0281701 A1 | 12/2006 | Stein et al. |
| 2007/0021362 A1 | 1/2007 | Geller et al. |
| 2007/0135333 A1 | 6/2007 | Geller et al. |
| 2008/0194463 A1 | 8/2008 | Weller et al. |

FOREIGN PATENT DOCUMENTS

| | | |
|---|---|---|
| WO | 9301286 A2 | 1/1993 |
| WO | 9740854 A2 | 11/1997 |
| WO | 0149775 A2 | 7/2001 |
| WO | 02079467 A2 | 10/2002 |
| WO | 02094250 A2 | 11/2002 |
| WO | WO2004/097017 | 11/2004 |
| WO | 2006047683 A2 | 5/2006 |
| WO | WO2006/050414 | 5/2006 |
| WO | 2006085973 A2 | 8/2006 |
| WO | WO2007/009094 | 1/2007 |

OTHER PUBLICATIONS

Agrawal et al., "Site-specific excision from RNA by RNase H and mixed-phosphate-backbone oligodeoxynucleotides" Proc. Natl. Acad. Sci. USA 87(4): 1401-1405, 1990.
Agrawal et al., "Antisense therapeutics: is it as simple as complementary base recognition?" Molecular Med. Today 6: 72-81, 2000.
Agrawal, "Antinsense oligonucleotides: towards clinical trials" Tibtech 14(10): 376-387, 1996.
Branch, "A good antisense molecule is hard to find" Trends in Biochem. Sci. 23: 45-50, 1998.
Crooke, Antisense Research and Applications, ed. Springer, 1999, Chapter 1, "Basic Principles of Antisense Therapeutics" pp. 1-50.
Deere et al., "Antisense Phosphorodiamidate Morpholino Oligomer Length and Target Position Effects on Gene-Specific Inhibition in *Escherichia coli*" Antimicrobial Agents and Chemotherapy 49(1): 249-255, 2005. Dryselius et al., "The Translation Start Codon Region Is Sensitive to Antisense PNA Inhibition in *Escherichia coli*" Oligonucleotides 13: 427-433, 2003.
Galloway et al., "A Mutant of *Escherichia coli* Defective in the First Step of Endotoxin Biosynthesis" J. Biol. Chem. 265 (11): 6394-6402, 1990.
Geller et al., "Antisense Antibacterial Method and Compound" U.S. Appl. No. 12/613,428, filed Nov. 5, 2009.
Geller et al., "Antisense Antibacterial Method and Compound" U.S. Appl. No. 12/723,035, filed Mar. 12, 2010.
Good et al., "Antisense PNA effects in *Escherichia coli* are limited by the outer-membrane LPS layer" Microbiology 146 (Pt 10): 2665-2670, 2000.
Green et al., "Antisense Oligonucleotides: An Evolving Technology for the Modulation of Gene Expression in Human Disease" J. Am. Coll. Surg. 191(1): 93-105, 2000.
Greenberg et al., "Antisense Phosphorodiamidate Morpholino Oligomers Targeted to an Essential Gene Inhibit Burkholderia cepacia Complex" The Journal of Infectious Diseases 201(12): 000-000, 2010.

(Continued)

Primary Examiner — Sean McGarry
(74) Attorney, Agent, or Firm — Seed IP Law Group PLLC

(57) ABSTRACT

A method for enhancing, by at least 10 fold, the antibacterial activity of an antisense oligonucleotide composed of morpholino subunits linked by phosphorus-containing intersubunit linkages. The method includes one or both of: conjugating an arginine-rich carrier to a 3' or 5' end of the oligonucleotide and modifying the oligonucleotide to contain 20%-50% intersubunit linkages that are positively charged at physiological pH. Also disclosed is an antisense oligonucleotide having enhanced antibacterial activity by virtue of one or both modifications.

17 Claims, 37 Drawing Sheets

OTHER PUBLICATIONS

International Search Report, mailed Aug. 11, 2006, for PCT/US2005/023553, 6 pages.

Jackowski et al., "Ratio of Active to Inactive Forms of Acyl Carrier Protein in *Escherichia coli*" J. Biol. Chem. 258(24): 15186-15191, 1983.

Jen et al., "Suppression of Gene Expression by Targeted Disruption of Messenger RNA: Available Options and Current Strategies" Stem Cells 18: 307-319, 2000.

Mellbye et al., "Variations in Amino Acid Composition of Antisense Peptide-Phosphorodiamidate Morpholino Oligomer Affect Potency against *Escherichia coli* In Vitro and In Vivo" Antimicrobial Agents and Chemotherapy 53(2): 525-530, 2009.

Micklefield, "Backbone Modification of Nucleic Acids: Synthesis, Structure and Therapeutic Applications" Curr. Med. Chem. 8(10): 1157-1179, 2001.

Mitev et al., "Inhibition of Intracellular Growth of *Salmonella enterica* Serovar Typhimurium in Tissue Culture by Antisense Peptide-Phosphorodiamidate Morpholino Oligomer" Antimicrobial Agents and Chemotherapy 53(9): 3700-3704, 2009.

Moulton et al., "Cellular Uptake of Antisense Morpholino Oligomers Conjugated to Arginine-Rich Peptides" Bioconjugate Chem. 15: 290-299, 2004.

Moulton et al., "HIV Tat Peptide Enhances Cellular Delivery of Antisense Morpholino Oligomers" Antisense & Nucleic Acid Drug Dev. 13: 31-43, 2003.

Moulton et al., "Peptide-assisted delivery of steric-blocking antisense oligomers" Curr. Opin. Mol. Ther. 5(2): 123-132, 2003.

Nelson et al., "Arginine-Rich Peptide Conjugation to Morpholino Oligomers: Effects on Antisense Activity and Specificity" Bioconjugate Chem. 16: 959-966, 2005.

Nielsen, "Peptide nucleic acids as antibacterial agents via the antisense principle" Exp. Opin. Invest. Drugs 10(2): 331-341, 2001.

Nielsen, "Peptide nucleic acids: on the road to new gene therapeutic drugs" Pharmacol. Toxicol. 86(1): 3-7, 2000.

Partridge et al., "A Simple Method for Delivering Morpholino Antisense Oligos into the Cytoplasm of Cells" Antisense & Nucleic Acid Drug Dev. 6(3): 169-175, 1996.

Petersen et al., "Synthesis of Thymidine Dimers Containing Piperazine in the Internucleoside Linkage and their Incorporation into Oligodeoxynucleotides" Tetrahedron 51(7): 2145-2154, 1995.

Polacco et al., "A Mutant of *Escherichia coli* Conditionally Defective in the Synthesis of Holo-[Acyl Carrier Protein]" J. Biol. Chem. 256(11): 5750-5754, 1981.

Rothbard et al., "Arginine-Rich Molecular Transporters for Drug Delivery: Role of Backbone Spacing in Cellular Uptake" J. Med. Chem. 45: 3612-3618, 2002.

Stein et al., "A Specificity Comparison of Four Antisense Types: Morpholino, 2'-O-Methyl RNA, DNA, and Phosphorothioate DNA" Antisense & Nucleic Acid Drug Development 7(3): 151-157, 1997.

Summerton, "Morpholino antisense oligomers: the case for an RNase H-independent structural type" Biochim. et. Biophys. ACTA 1489(1): 141-157, 1999.

Summerton, Peptide Nucleic Acids, Morpholinos and Related Antisense Biomolecules, Landes Bioscience/Eurekah.com and Kluwer Academic/Plenum Publishers, ed. C.G. Janson and M.J. During, 2006, Chapter 6, "Morpholinos and PNAs Compared" pp. 97-101.

Uhlmann et al., "Antisense Oligonucleotides: A New Therapeutic Principle" Chemical Reviews 90(4): 544-584, 1990.

Wang et al., "Assessment of the utilization of the antisense RNA strategy to identify essential genes in heterologous bacteria" FEMS Microbiology Letters 220(2): 171-176, 2003.

Weller et al., "Antibacterial Antisense Oligonucleotide and Method" U.S. Appl. No. 12/723,413, filed Mar. 12, 2010.

Wiersinga, "Beyond Antibiotics: New Horizons in Treating Burkholderia Species Infections" The Journal of Infectious Diseases 201(12): 000-000, 2010.

Anderson et al., *Antimicrobial Agents and Chemotherapy*, 40(9):2004-2011 (1996).

Blommers et al., *Nucleic Acids Res*, 22(20):4187-4194 (1994).

Bramhill et al. *Annu Rev Cell Dev Biol.*, 13:395-424 (1997).

Cross, C. W., J. S. Rice, et al. (1997). "Solution structure of an RNA×DNA hybrid duplex containing a 3'-thioformacetal linker and an RNA A-tract." *Biochemistry* 36(14):4096-107.

Donachie, W.D. (1993). *Annu. Rev. Microbiol.*, 47:199-230.

Gait, M. J., A. S. Jones, et al. (1974). "Synthetic-analogues of polynucleotides XII. Synthesis of thymidine derivatives containing an oxyacetamido- or an oxyformamido-linkage instead of a phosphodiester group." *J Chem Soc [Perkin 1]* 0(14): 1684-6.

Geller et al., *Antimicrobial Agents and Chemotherapy*, 47(10):3233-3239 (2003).

Geller et al., *J. Biol. Chem.*, 264(28):16465-16469 (1989).

Geller et al., *J. Biol. Chem.*, 55:983-988 (2005).

Gerdes et al., *J. Bacteriol.*, 185(19):5673-5684 (2003).

Good et al., *Nature Biotechnology*, 19(4):360-364 (2001).

Good et al., *PNAS*, 95:2073-2076 (1998).

Hale et al., *J. Bacteriol.*, 181(1):167-176 (1999).

Lesnikowski, Z. J., M. Jaworska, et al., "Octa(thymidine methanephosphonates) of partially defined stereochemistry: synthesis and effect of chirality at phosphorus on binding to pentadecadeoxyriboadenylic acid." *Nucleic Acids Res* 18(8): 2109-15 (1990).

Lutkenhaus, J. and Addinall, S.G., *Annu. Rev. Biochem.*, 66:93-116 (1997).

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem* 12(1): 154-7.

Pari et al., *Antimicrobial Agents and Chemotherapy*, 39(5):1157-1161 (1995).

Rahman et al., *Antisense Research and Development*, 1:319-327 (1991).

Summerton, J. and D. Weller (1997). "Morpholino antisense oligomers: design, preparation, and properties." Antisense Nucleic Acid Drug Dev 7(3): 187-95.

Summerton et al., *Antisense & Nucleic Acid Drug Development*, 7:63-70 (1997).

Tan et al., *Antimicrobial Agents and Chemotherapy*, 49(8):3202-3207 (2005).

Tilley et al., *Antimicrobial Agents and Chemotherapy*, 50(8):2789-2796 (2006).

Zhang, Y and Cronan, J.E., *J. Bacteriology*, 178(12):3614-3620 (1996).

Agrawal et al., "Oligodeoxynucleoside phosphoramidates and phosphorothioates as inhibitors of human immunodeficiency virus," *Proc. Natl. Acad. Sci. USA* 85:7079-7083, 1988.

Geller et al., "Antisense phosphorodiamidate morpholino oligomer inhibits viability of *Escherichia coli* in pure culture and in mouse peritonitis," *Journal of Antimicrobial Chemotherapy* 55:983-988, 2005.

Geller et al., "Antisense Antibacterial Method and Compound," Office Action mailed Sep. 29, 2010, U.S. Appl. No. 11/173,847, 25 pages.

Iversen et al., "Splice-Region Antisense Composition and Method," Office Action mailed on Apr. 23, 2010, U.S. Appl. No. 11/433,214, 17 pages.

Iversen et al., "Antisense Antiviral Compound and Method for Treating ssRNA Viral Infection," Office Action mailed Oct. 19, 2010, U.S. Appl. No. 11/432,031, 25 pages.

Stein et al., "Antisense Antiviral Agent and Method for Treating ssRNA Viral Infection," Office Action mailed Feb. 17, 2010, U.S. Appl. No. 11/431,968, 19 pages.

ANTIBACTERIAL ANTISENSE OLIGONUCLEOTIDE AND METHOD

This application claims priority to U.S. patent application Ser. No. 11/487,009 filed on Jul. 13, 2006, which claims priority to U.S. Provisional Patent Application No. 60/699,280 filed on Jul. 13, 2005, now abandoned, both of which are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_438C1_SEQUENCE_LISTING.txt. The text file is 6 KB, was created on Apr. 9, 2010, and is being submitted electronically via EFS-Web.

FIELD OF THE INVENTION

The present invention relates to peptide-conjugated morpholino oligonucleotide compounds having partially charged backbones and that are antisense to bacterial genes, and methods for use of such compounds in inhibiting bacterial growth, e.g., in an infected mammalian subject.

REFERENCES

Anderson, K. P., M. C. Fox, et al. (1996). *Antimicrob Agents Chemother* 40(9): 2004-11.
Bramhill, D. (1997). *Annu Rev Cell Dev Biol* 13: 395-424.
Donachie, W. D. (1993). *Annu Rev Microbiol* 47:199-230.
Geller, B. L., J. D. Deere, et al. (2003). *Antimicrob Agents Chemother* 47(10): 3233-9.
Geller, B. L. and H. M. Green (1989). *J Biol Chem* 264(28): 16465-9.
Gerdes, S. Y., M. D. Scholle, et al. (2003). *J Bacteriol* 185(19): 5673-84.
Good, L., S. K. Awasthi, et al. (2001). *Nat Biotechnol* 19(4): 360-4.
Hale, C. A. and P. A. de Boer (1999). *J Bacteriol* 181(1): 167-76.
Lutkenhaus, J. and S. G. Addinall (1997). *Annu Rev Biochem* 66: 93-116.
Pari, G. S., A. K. Field, et al. (1995). *Antimicrob Agents Chemother* 39(5): 1157-61.
Summerton, J., D. Stein, et al. (1997). *Antisense Nucleic Acid Drug Dev* 7(2): 63-70.
Summerton, J. and D. Weller (1997). *Antisense Nucleic Acid Drug Dev* 7(3): 187-95.
Zhang, Y. and J. E. Cronan, Jr. (1996). *J Bacteriol* 178(12): 3614-20.

BACKGROUND OF THE INVENTION

Currently, there are several types of antibiotic compounds in use against bacterial pathogens, and these compounds act through a variety of anti-bacterial mechanisms. For example, beta-lactam antibiotics, such as penicillin and cephalosporin, act to inhibit the final step in peptidoglycan synthesis. Glycopeptide antibiotics, including vancomycin and teichoplanin, inhibit both transglycosylation and transpeptidation of muramyl-pentapeptide, again interfering with peptidoglycan synthesis. Other well-known antibiotics include the quinolones, which inhibit bacterial DNA replication, inhibitors of bacterial RNA polymerase, such as rifampin, and inhibitors of enzymes in the pathway for production of tetrahydrofolate, including the sulfonamides.

Some classes of antibiotics act at the level of protein synthesis. Notable among these are the aminoglycosides, such as kanamycin and gentamycin. This class of compounds targets the bacterial 30S ribosome subunit, preventing the association with the 50S subunit to form functional ribosomes. Tetracyclines, another important class of antibiotics, also target the 30S ribosome subunit, acting by preventing alignment of aminoacylated tRNA's with the corresponding mRNA codon. Macrolides and lincosamides, another class of antibiotics, inhibit bacterial synthesis by binding to the 50S ribosome subunit, and inhibiting peptide elongation or preventing ribosome translocation.

Despite impressive successes in controlling or eliminating bacterial infections by antibiotics, the widespread use of antibiotics both in human medicine and as a feed supplement in poultry and livestock production has led to drug resistance in many pathogenic bacteria. Antibiotic resistance mechanisms can take a variety of forms. One of the major mechanisms of resistance to beta lactams, particularly in Gram-negative bacteria, is the enzyme beta-lactamase, which renders the antibiotic inactive. Likewise, resistance to aminoglycosides often involves an enzyme capable of inactivating the antibiotic, in this case by adding a phosphoryl, adenyl, or acetyl group. Active efflux of antibiotics is another way that many bacteria develop resistance. Genes encoding efflux proteins, such as the tetA, tetG, tetL, and tetK genes for tetracycline efflux, have been identified. A bacterial target may develop resistance by altering the target of the drug. For example, the so-called penicillin binding proteins (PBPs) in many beta-lactam resistant bacteria are altered to inhibit the critical antibiotic binding to the target protein. Resistance to tetracycline may involve, in addition to enhanced efflux, the appearance of cytoplasmic proteins capable of competing with ribosomes for binding to the antibiotic. For those antibiotics that act by inhibiting a bacterial enzyme, such as for sulfonamides, point mutations in the target enzyme may confer resistance.

The appearance of antibiotic resistance in many pathogenic bacteria—in many cases involving multi-drug resistance—has raised the specter of a pre-antibiotic era in which many bacterial pathogens are simply untreatable by medical intervention. There are two main factors that could contribute to this scenario. The first is the rapid spread of resistance and multi-resistance genes across bacterial strains, species, and genera by conjugative elements, the most important of which are self-transmissible plasmids. The second factor is a lack of current research efforts to find new types of antibiotics, due in part to the perceived investment in time and money needed to find new antibiotic agents and bring them through clinical trials, a process that may require a 20-year research effort in some cases.

In addressing the second of these factors, some drug-discovery approaches that may accelerate the search for new antibiotics have been proposed. For example, efforts to screen for and identify new antibiotic compounds by high-throughput screening have been reported, but to date no important lead compounds have been discovered by this route.

Several approaches that involve antisense agents designed to block the expression of bacterial resistance genes or to target cellular RNA targets, such as the rRNA in the 30S ribosomal subunit (see, for example, co-owned U.S. Pat. No. 6,677,153, which is incorporated by reference herein), or by targeting the mRNA of bacterial proteins that are critical in bacterial replication, such as acyl carrier protein (acpP), gyrase A subunit (gyrA), or the cell division protein ftsZ (see co-owned U.S. patent applications 20070021362 and 20070049542, both of which are incorporated by reference herein). Although these approaches have been shown to be successful in blocking bacterial replication, they have been limited in commercial applications by the concentrations of antisense compounds required for efficacy in treating bacterial infections in a mammalian host.

There is thus a continuing need for new antibiotics that (i) are not subject to the principal types of antibiotic resistance currently hampering antibiotic treatment of bacteria, (ii) can be developed rapidly and with some reasonable degree of predictability as to target-bacteria specificity, (iii) are effective at low doses, and (iv) show relatively few side effects.

SUMMARY OF THE INVENTION

The invention includes, in one aspect, a method for enhancing the antibacterial activity of an antisense oligonucleotide composed of morpholino subunits linked by phosphorus-containing intersubunit linkages joining a morpholino nitrogen of one subunit to a 5' exocyclic carbon of an adjacent subunit, where the oligonucleotide contains between 10-20 bases and a targeting sequence of at least 10 contiguous bases complementary to a bacterial RNA target, and where binding of the oligonucleotide to the RNA target region is effective to inhibit growth of an infectious bacterium in a mammalian host. The method includes one or both of the steps of:

(a) conjugating to the oligonucleotide, a carrier peptide (i) containing 6-16, preferably 8-14 amino acids composed of the subsequences selected from the group represented by XXY, XY, XZZ and XZ, where (a) each X subunit independently represents arginine or an arginine analog, said analog being a cationic α-amino acid comprising a side chain of the structure R1N=C(NH2)R2, where R1 is H or R; R2 is R, NH2, NHR, or NR2, where R is lower alkyl or lower alkenyl and may further include oxygen or nitrogen; R1 and R2 may together form a ring; and the side chain is linked to said amino acid via R1 or R2; (b) each Y subunit independently represents a neutral linear amino acid —C(O)—(CHR)m-NH—, where (i) m is 1 to 7 and each R is independently H or methyl, and (c) Z is an α-amino acid having a neutral side chain selected from a substituted or unsubstituted aralkyl, and (ii) coupled to the oligonucleotide at the peptide's C terminus, and (b) modifying the oligonucleotide to contain 10%-80%, preferably 20%-50% intersubunit cationic linkages that are positively charged at physiological pH.

The carrier peptide in step (a) may be represented by the sequence $(RY'R)_n$, or $(RY')_n$, where R is arginine and Y' is a linear alkanoic acid having 2-7 carbon atoms in its backbone chain, such as the peptides $(RAhxR)_4$, where Ahx is 6-amino hexanoic acid; and $(RAhx)_6$, where Ahx is 6-amino hexanoic acid.

The carrier peptide in step (a) may be linked at its C-terminus to the 5' end of the oligonucleotide through a one- or two-amino acid linker. Exemplary linkers include AhxβAla, where Ahx is 6-aminohexanoic acid and βAla is β-alanine. Carrier peptide length, e.g., 8-14, is considered independent of the presence of one or more amino-acid linkers.

The enhancement in activity produced by step (a) alone or step (b) alone may be effective to enhance the anti-bacterial activity of an uncharged oligonucleotide, as measured by inhibition in bacterial growth in vitro over an eight-hour period, by a factor of at least 10 relative to the measured inhibition of the uncharged oligonucleotide in the absence of the carrier peptide. The enhancement in activity produced by step (a) and step (b) together may be effective to enhance the anti-bacterial activity of the peptide-conjugated oligonucleotide, as measured by inhibition in bacterial growth in vitro over an eight-hour period, by a factor of at least $10^2$ relative to the measured inhibition of the uncharged oligonucleotide in the absence of the carrier peptide.

The morpholino subunits in the oligonucleotide may be joined by phosphorodiamidate linkages, including both uncharged and cationic linkages, in accordance with the structure:

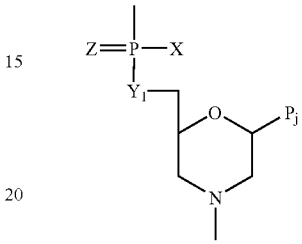

where
Z is S or O,
$X=NR^1R^2$ or $OR^6$,
$Y=O$ or $NR^7$,
and each said linkage is selected from:
(a) uncharged linkage (a), where each of $R^1$, $R^2$, $R^6$ and $R^7$ is independently selected from hydrogen and lower alkyl;
(b1) cationic linkage (b1), where $X=NR^1R^2$ and $Y=O$, and $NR^1R^2$ represents an optionally substituted piperazino group, such that $R^1R^2$=—CHRCHRN($R^3$)($R^4$)CHRCHR—, where each R is independently H or $CH_3$,
$R^4$ is H, $CH_3$ or an electron pair, and
$R^3$ is selected from H, lower alkyl, C(=NH)NH$_2$, Z-L-NHC(=NH)NH$_2$, and [C(O)CHR'NH]$_m$H, where Z is carbonyl (C(O)) or a direct bond, L is an optional linker up to 18 atoms in length having bonds selected from alkyl, alkoxy, and alkylamino, R' is a side chain of a naturally occurring amino acid or a one- or two-carbon homolog thereof, and m is 1 to 6;
(b2) cationic linkage (b2), where $X=NR^1R^2$ and $Y=O$, $R^1=H$ or $CH_3$, and $R^2=LNR^3R^4R^5$, where L, $R^3$, and $R^4$ are as defined above, and $R^5$ is H, lower alkyl, or lower (alkoxy) alkyl; and
(b3) cationic linkage (b3), where $Y=NR^7$ and $X=OR^6$, and $R^7=LNR^3R^4R^5$, where L, $R^3$, $R^4$ and $R^5$ are as defined above, and $R^6$ is H or lower alkyl; and at least one said linkage is selected from cationic linkages (b1), (b2), and (b3);

In various embodiments of the backbone linkages: (i) each of $R^1$ and $R^2$, in linkages of type (a), is methyl; (ii) at least one linkage is of type (b1), and each R is H, $R^4$ is H, $CH_3$, or an electron pair, and $R^3$ is selected from H, $CH_3$, C(=NH)NH$_2$, and C(O)-L-NHC(=NH)NH$_2$; (iii) at least one linkage is of type (b1), and each R is H, $R^4$ is an electron pair, and $R^3$ is selected from C(=NH)NH$_2$ and C(O)-L-NHC(=NH)NH$_2$; (iv) at least one linkage is of type (b1), and each R is H, $R^4$ is an electron pair, and $R^3$ is selected from C(=NH)NH$_2$ and C(O)-L-NHC(=NH)NH$_2$, and more particularly, $R^3$ is C(O)-L-NHC(=NH)NH$_2$, and L is a hydrocarbon having the structure —(CH$_2$)$_n$—, where n is 1 to 12; (v) at least one linkage is of type (b1), and each R is H, and each of $R^3$ and $R^4$ is independently H or $CH_3$.

Considering the oligonucleotide to have approximately equal-length 5', 3' and center regions, and the percentage of cationic linkages in step (b) said center region may be greater than about 70%.

Where the antisense oligonucleotide is intended for use in treating a gram-negative bacterial infection, the targeting sequence of the oligonucleotide may be complementary to a target sequence containing or within 20 bases, in a downstream direction, of the translational start codon of a bacterial mRNA that encodes acyl carrier protein (acpP). For example, the targeting sequence may be complementary to at least ten contiguous bases in a sequence selected from the group consisting of SEQ ID NOS: 2, 5, 8, 11, 14, 17, 20, 23, 28, 31, 34, 36, 39, 42, 45, 48, 51, 54, 57 and 60.

Where the antisense oligonucleotide is intended for use treating a gram-negative bacterial infection, wherein the targeting sequence is complementary to a target sequence containing or within 20 bases, in a downstream direction, of the translational start codon of a bacterial mRNA that encodes gyrase A subunit (gyrA). For example, the targeting sequence may be complementary to at least ten contiguous bases in a sequence selected from the group consisting of SEQ ID NOS: 3, 6, 9, 12, 15, 18, 24, 29, 32, 35, 37, 40, 43, 46, 49, 52, 55, 58 and 61.

Where the antisense oligonucleotide is intended for targeting a bacterial mRNA encoding a bacterial ftsZ protein, the compound targeting sequence may be complementary to at least ten contiguous bases in a sequence selected from the group consisting of SEQ ID NOS: 1, 4, 7, 10, 13, 16, 19, 22, 27, 30, 33, 38, 41, 44, 47, 50, 53, 56 and 59.

Other bacterial RNA targets may include the AUG start site regions, e.g., the AUG start site itself and up to 15 bases downstream thereof, of a variety of other essential bacterial proteins, and the 16S or 23S rRNA of the 30S bacterial ribosomal subunit.

In another aspect, the invention includes an improved antisense oligonucleotide useful for treating a bacterial infection, where the oligonucleotide is composed of morpholino subunits linked by phosphorus-containing intersubunit linkages joining a morpholino nitrogen of one subunit to a 5' exocyclic carbon of an adjacent subunit, where the oligonucleotide contains between 10-20 bases and a targeting sequence of at least 10 contiguous bases complementary to a bacterial RNA target, and where binding of the oligonucleotide to the RNA target region is effective to inhibit growth of the infectious bacterium. The improvement includes one or both of the modifications (a) and (b):

(a) conjugated to the oligonucleotide, a carrier peptide that is (i) represented by the sequence selected from the group consisting of $(XYX)_n$, $(XY)_n$ and $(XZZ)_n$, where (a) each X subunit independently represents arginine or an arginine analog, said analog being a cationic α-amino acid comprising a side chain of the structure R1N=C(NH2)R2, where R1 is H or R; R2 is R, NH2, NHR, or NR2, where R is lower alkyl or lower alkenyl and may further include oxygen or nitrogen; R1 and R2 may together form a ring; and the side chain is linked to said amino acid via R1 or R2; (b) each Y subunit independently represents a neutral linear amino acid —C(O)—(CHR)m-NH—, where (i) m is 1 to 7 and each R is independently H or methyl, or (ii) m is 1 and R is a neutral side chain selected from substituted or unsubstituted alkyl, alkenyl, alkynyl, aryl, and aralkyl, wherein said neutral side chain, when selected from substituted alkyl, alkenyl, and alkynyl, includes at most one heteroatom for every four carbon atoms; and (c) each Z subunit independently represents an amino acid selected from alanine, asparagine, cysteine, glutamine, glycine, histidine, lysine, methionine, serine, and threonine, and n is selected to yield a total of 8-14 amino acids in the peptide sequence, and (ii) coupled to the oligonucleotide at the peptide's C terminus, and (b) the presence in the oligonucleotide of 10%-80%, preferably 20%-50% intersubunit cationic linkages that are positively charged at physiological pH.

Also discloses is a method for treating a bacterial infection using the improved antisense oligonucleotide.

These and other objects and features of the claimed subject matter will become more fully apparent when the following detailed description is read in conjunction with the accompanying drawings.

BRIEF DESCRIPTION OF THE FIGURES

FIG. 2O illustrates the introduction of peptides into the backbone morpholino oligomers.

DETAILED DESCRIPTION

I. Definitions

Figure 1A:
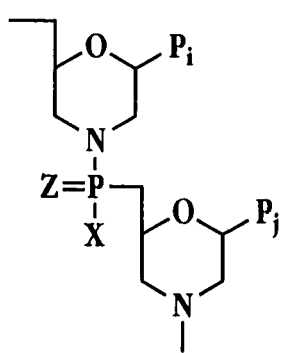
FIGS. 1A-D show the repeating subunit segment of exemplary morpholino oligonucleotides, designated A through D, constructed using subunits having 5-atom (A), six-atom (B) and seven-atom (C-D) linking groups suitable for forming polymers.

The terms below, as used herein, have the following meanings, unless indicated otherwise:

As used herein, the terms "compound", "agent", "oligomer" and "oligonucleotide" may be used interchangeably with respect to the antisense oligonucleotides of the claimed subject matter.

As used herein, the terms "antisense oligonucleotide" and "oligonucleotide" or "antisense compound" or "oligonucleotide compound" are used interchangeably and refer to a sequence of subunits, each having a base carried on a backbone subunit composed of morpholino backbone groups, and where the backbone groups are linked by intersubunit linkages (both charged and uncharged) that allow the bases in the compound to hybridize to a target sequence in an RNA by Watson-Crick base pairing, to form an RNA:oligonucleotide heteroduplex within the target sequence. The oligonucleotide may have exact sequence complementarity to the target sequence or near complementarity. Such antisense oligonucleotides are designed to block or inhibit translation of the mRNA containing the target sequence, or to inhibit bacterial protein synthesis by binding to bacterial 16S or 23S rRNA, and may be said to be "directed to" a sequence with which it hybridizes. Exemplary structures for antisense oligonucleotides for use in the claimed subject matter in include the morpholino subunit types shown in FIGS. 1A-D.

The term "oligonucleotide" or "antisense oligonucleotide" also encompasses an oligonucleotide having one or more additional moieties conjugated to the oligonucleotide, e.g., at its 3'- or 5'-end, such as a polyethyleneglycol moiety or other hydrophilic polymer, e.g., one having 10-100 monomeric subunits, which may be useful in enhancing solubility.

A carrier peptide conjugated to an antisense oligonucleotide, e.g., by covalent linkage between the peptide's C terminal end and the 5'- or 3'-end of the oligonucleotide, is separately named, and typically not included within the term "oligonucleotide," unless understood otherwise from the context of the statement. The carrier peptide and covalently attached antisense oligonucleotide are also referred to herein as a conjugate or conjugate compound. More generally, a "peptide-conjugated morpholino antisense oligonucleotide" is a morpholino antisense oligonucleotide conjugated at either its 5' or 3' termini to an arginine-rich peptide carrier.

By "arginine-rich carrier peptide" is meant that the carrier peptide has at least 2 arginine residues and preferably 50% or more arginine or arginine-analog residues (Arg residue), each Arg residue or ArgArg residue pair preferably being separated by one or more uncharged, preferably non-polar amino acid residues. Preferred arginine-rich carrier peptides in the invention contain 8-14 amino acids composed of the subsequences selected from the group represented by XXY, XY, XZZ and XZ, where (a) each X subunit independently represents arginine or an arginine analog ("Arg residue"), said analog being a cationic α-amino acid comprising a side chain of the structure R1N=C(NH2)R2, where R1 is H or R; R2 is R, NH2, NHR, or NR2, where R is lower alkyl or lower alkenyl and may further include oxygen or nitrogen; R1 and R2 may together form a ring; and the side chain is linked to said amino acid via R1 or R2; (b) each Y subunit independently represents a neutral linear amino acid —C(O)—(CHR)m-NH—, where (i) m is 1 to 7, such as β-alanine (m=2) and 6-amino hexanoic acid (m=6), and each R is independently H or methyl, and (c) Z is an α-amino acid having a neutral side chain selected from a substituted or unsubstituted aralkyl, such as phenylalanine, and (ii) coupled to the oligonucleotide at the peptide's C terminus. Exemplary arginine rich peptides are listed as SEQ ID NOS:79-87.

The carrier peptide may be linked at its C-terminus to one end of the oligonucleotide, e.g., the 5'-end, through a one- or two-amino acid linker, such as the linker is AhxβAla, where Ahx is 6-aminohexanoic acid and βAla is β-alanine, and where the linker forms part of the carrier peptide.

Figure 1B:
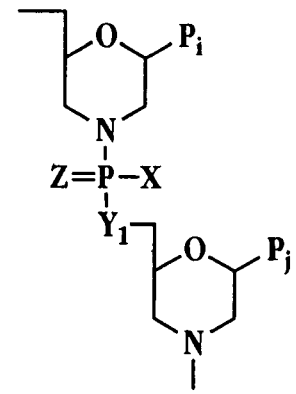
Figure 1C:
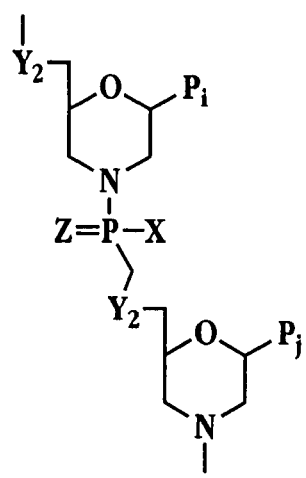
Figure 1D:
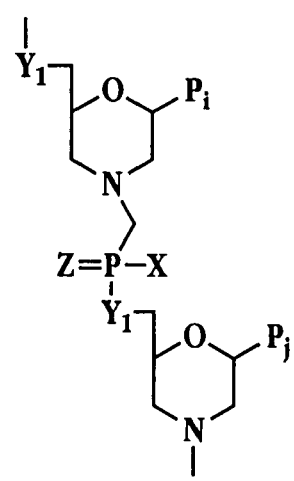

As used herein, a "morpholino oligomer" or "morpholino oligonucleotide" refers to an antisense oligonucleotide having a backbone which supports bases capable of hydrogen bonding to natural polynucleotides, e.g., DNA or RNA, is composed of morpholino subunit structures of the form shown in FIGS. 1A-1D, where (i) the structures are linked together by phosphorous-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. Various subunit and backbone linkage structures in an oligonucleotide composed of morpholino subunits linked by phosphorus-containing intersubunit linkages are shown in FIGS. 1A-1D, as described further below. Morpholino oligonucleotides of this type (including antisense oligonucleotides) are detailed, for example, in co-owned U.S. Pat. Nos. 5,698,685, 5,217,866, 5,142,047, 5,034,506, 5,166, 315, 5,185,444, 5,521,063, and 5,506,337, all of which are expressly incorporated by reference herein. FIG. 1A shows a 1-atom phosphorous-containing linkage which forms the five atom repeating-unit backbone where the morpholino rings are linked by a 1-atom phosphonamide linkage. FIG. 1B shows a six atom repeating-unit backbone where the atom Y linking the 5' morpholino carbon to the phosphorous group may be sulfur, nitrogen, carbon or, preferably, oxygen. The X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures. FIGS. 1C-D show 7-atom unit-length backbones. In FIG. 1C the X moiety is as in Structure B of FIG. 1 and the moiety Y may be a methylene, sulfur, or preferably oxygen. In the structure shown in FIG. 1D the X and Y moieties are as in FIG. 1B. In all subunits depicted in FIGS. 1A-D, Z is O or S, and $P_i$ or $P_j$ is adenine, cytosine, guanine, thymine, uracil or inosine.

A "phosphoramidate" group comprises phosphorus having three attached oxygen atoms and one attached nitrogen atom, while a "phosphorodiamidate" group (see e.g. FIGS. 1A-B) comprises phosphorus having two attached oxygen atoms and two attached nitrogen atoms. In the uncharged or the cationic intersubunit linkages of the oligomers described herein, one nitrogen is always pendant to the backbone chain. The second nitrogen, in a phosphorodiamidate linkage, is typically the ring nitrogen in a morpholino ring structure (again, see FIGS. 1A-B). In a thiophosphoramidate orthiophosphorodiamidate linkage, one oxygen atom, typically the oxygen pendant to the backbone in the oligomers described herein, is replaced with sulfur. Preferred morpholino oligonucleotides include those composed of morpholino subunit structures of the form shown in FIG. 1B, where X=$NH_2$, $N(CH_3)_2$, or 1-piperazine or other charged group, Y=O, and Z=O. An oligonucleotide compound having this backbone structure is generally referred to herein as a "PMO" (phosphorodiamidate morpholino oligonucleotide), where "P-PMO" refers to a peptide-conjugated PMO, "PMO+" refers to a PMO with charged backbone linkages, and "P-PMO+" refers to a peptide-conjugated PMO having cationic backbone linkages.

The terms "charged", "uncharged", "cationic" and "anionic" as used herein refer to the predominant state of a chemical moiety at near-neutral pH, e.g. about 6 to 8. Preferably, the term refers to the predominant state of the chemical moiety at physiological pH, that is, about 7.4. Thus a cationic backbone linkage is predominantly positively charged at pH 7.4.

"Lower alkyl" refers to an alkyl radical of one to six carbon atoms, as exemplified by methyl, ethyl, n-butyl, i-butyl, t-butyl, isoamyl, n-pentyl, and isopentyl. In selected embodiments, a "lower alkyl" group has one to four carbon atoms, or 1-2 carbon atoms; i.e. methyl or ethyl. Analogously, "lower alkenyl" refers to an alkenyl radical of two to six, preferably three or four, carbon atoms, as exemplified by allyl and butenyl.

A "non-interfering" substituent is one that does not adversely affect the ability of an antisense oligomer as described herein to bind to its intended target. Such substituents include small and preferably non-polar groups such as methyl, ethyl, methoxy, ethoxy, hydroxy, or fluoro.

As used herein, an oligonucleotide has (or is modified to have) a specified percentage of cationic linkages in its backbone linkages if at least that percentage of phosphorus-containing backbone linkages are cationic, i.e., substantially positively charged at physiological pH, where substantially all of the remainder backbone linkages are uncharged at physiological pH. Thus, a 16mer oligonucleotide containing between 20% and 50% cationic linkages would include between 3-8 cationic linkages. Preferred cationic backbone linkages, and the synthesis of morpholino oligonucleotides containing such linkages are detailed below.

As used herein, a "nuclease-resistant" oligonucleotide molecule (oligonucleotide) is one whose backbone is not susceptible to nuclease cleavage of a phosphodiester bond.

As used herein, an antisense oligonucleotide "specifically hybridizes" to a target polynucleotide if the oligonucleotide hybridizes to the target under physiological conditions, with a Tm greater than 37° C. As will be seen below, the antisense oligonucleotides of the claimed subject matter have a preferred Tm values with respect to their target mRNAs of at least 45° C., typically between 50°-60° C. or greater.

The "Tm" of an oligonucleotide compound, with respect to its target mRNA, is the temperature at which 50% of a target sequence hybridizes to a complementary polynucleotide. Tm is determined under standard conditions in physiological saline, as described, for example, in Miyada C. G. and Wallace R. B. 1987. Oligonucleotide hybridization techniques. *Methods Enzymol.* 154:94-107.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

As used herein, a first sequence is an "antisense sequence" with respect to a second sequence, typically an RNA sequence, if a polynucleotide whose sequence is the first sequence specifically binds to, or specifically hybridizes with, the second polynucleotide sequence under physiological conditions.

As used herein, a "base-specific intracellular binding event involving a target RNA" refers to the sequence specific binding of an oligonucleotide to a target RNA sequence inside a cell. For example, a single-stranded polynucleotide can specifically bind to a single-stranded polynucleotide that is complementary in sequence.

As used herein, "essential bacterial genes" are those genes whose products play an essential role in an organism's functional repertoire as determined using genetic footprinting or other comparable techniques to identify gene essentiality.

An agent is "actively taken up by bacterial cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane.

As used herein, the terms "modulating expression" and "antisense activity" relative to an oligonucleotide refers to the ability of an antisense oligonucleotide to either enhance or reduce the expression of a given protein by interfering with the expression, or translation of RNA. In the case of reduced protein expression, the antisense oligonucleotide may directly block expression of a given gene, or contribute to the accelerated breakdown of the RNA transcribed from that gene.

As used herein, the term "inhibiting bacterial growth," refers to blocking or inhibiting replication and/or reducing the rate of replication of bacterial cells in a given environment, for example, in an infective mammalian host.

As used herein, the term "pathogenic bacterium," or "pathogenic bacteria," or "pathogenic bacterial cells," refers to bacterial cells capable of infecting and causing disease in a mammalian host, as well as producing infection-related symptoms in the infected host, such as fever or other signs of inflammation, intestinal symptoms, respiratory symptoms, dehydration, and the like.

As used herein, the terms "Gram-negative pathogenic bacteria" or "Gram-negative bacteria" refer to the phylum of proteobacteria, which have an outer membrane composed largely of lipopolysaccharides. All proteobacteria are gram negative, and include, but are not limited to *Escherichia coli, Salmonella*, other Enterobacteriaceae, *Pseudomonas, Burkholderi, Moraxella, Helicobacter, Stenotrophomonas, Bdellovibrio*, acetic acid bacteria, and *Legionella*. Other notable groups of gram negative bacteria include *Haemophilus influenzae*, the cyanobacteria, spirochaetes, green sulfur and green non-sulfur bacteria. The pathogenic capability of gram negative bacteria is usually associated with components of the bacterial cell wall, in particular the lipopolysaccharide (also known as LPS or endotoxin) layer.

As used herein, the terms "Gram-positive pathogenic bacteria" or "Gram-positive bacteria" refer to those bacteria that are stained dark blue or violet by Gram staining, in contrast to Gram-negative bacteria, which cannot retain the stain, instead taking up the counterstain and appearing red or pink. The stain is caused by a high amount of peptidoglycan in the cell wall, which typically, but not always, lacks the secondary membrane and lipopolysaccharide layer found in Gram-negative bacteria.

Gram-positive bacteria include many well-known genera such as *Bacillus, Listeria, Staphylococcus, Streptococcus, Enterococcus*, and *Clostridium*. It has also been expanded to include the Mollicutes, and bacteria such as *Mycoplasma*, which lack cell walls and so cannot be stained by Gram, but are derived from such forms.

As used herein, "effective amount" or "therapeutically effective amount" or "growth-inhibiting amount" relative to an antisense oligonucleotide refers to the amount of antisense oligonucleotide administered to a mammalian subject, either as a single dose or as part of a series of doses and which is effective to inhibit bacterial replication in an infected host, by inhibiting translation of a selected bacterial target nucleic acid sequence. The ability to block or inhibit bacterial replication in an infected host may be evidenced by a reduction in infection-related symptoms.

As used herein "treatment" of an individual or a cell is any type of intervention used in an attempt to alter the natural course of the individual or cell. Treatment includes, but is not limited to, administration of e.g., a pharmaceutical composition, and may be performed either prophylactically, or subsequent to the initiation of a pathologic event or contact with an etiologic agent.

II. Constructing the Antisense Oligonucleotide

Examples of morpholino oligonucleotides having phosphorus-containing backbone linkages are illustrated in FIGS. 1A-1D. Especially preferred is a phosphorodiamidate-linked morpholino oligonucleotide such as shown in FIG. 1B, which is modified, in accordance with one aspect of the present invention, to contain positively charged groups at 10%-80%, preferably 20%-50% of its backbone linkages. Morpholino oligonucleotides with uncharged backbone linkages, including antisense oligonucleotides, are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: 1) the ability to be linked in a oligomeric form by stable, uncharged or positively charged backbone linkages; 2) the ability to support a nucleotide base (e.g. adenine, cytosine, guanine, thymidine, uracil and inosine) such that the polymer formed can hybridize with a complementary-base target nucleic acid, including target RNA, Tm values above about 45° C. in relatively short oligonucleotides (e.g., 10-15 bases); 3) the ability of the oligonucleotide to be actively or passively transported into bacterial cells; and 4) the ability of the oligonucleotide: and an antisense:RNA heteroduplex to resist RNAse and RNaseH degradation, respectively.

Exemplary backbone structures for antisense oligonucleotides of the claimed subject matter include the morpholino subunit types shown in FIGS. 1A-1D, each linked by an uncharged or positively charged, phosphorus-containing subunit linkage. FIG. 1A shows a phosphorus-containing linkage which forms the five atom repeating-unit backbone, where the morpholino rings are linked by a 1-atom phosphoamide linkage. FIG. 1B shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines.

Alkyl, alkoxy and thioalkoxy preferably include 1-6 carbon atoms. The Z moieties are sulfur or oxygen, and are preferably oxygen.

The linkages shown in FIGS. 1C and 1D are designed for 7-atom unit-length backbones. In Structure 1C, the X moiety is as in Structure 1B, and the moiety Y may be methylene, sulfur, or, preferably, oxygen. In Structure 1D, the X and Y moieties are as in Structure 1B. Particularly preferred morpholino oligonucleotides include those composed of morpholino subunit structures of the form shown in FIG. 1B, where $X=NH_2$, $N(CH_3)_2$, or 1-piperazine or other charged group, $Y=O$, and $Z=O$.

As noted above, the substantially uncharged oligonucleotide may be modified, in accordance with an aspect of the invention, to include charged linkages, e.g. up to about 1 per every 2-5 uncharged linkages, such as about 4-5 per every 10 uncharged linkages. Optimal improvement in antisense activity may be seen when about half of the backbone linkages are cationic. Suboptimal enhancement is typically seen with a small number e.g., 10-20% cationic linkages, and where the number of cationic linkages are in the range 50-80%, and typically above about 6-%, the sequence specificity of the antisense binding to its target may be compromised or lost.

Additional experiments conducted in support of the present invention indicate that the enhancement seen with added cationic backbone charges may, in some cases, be further enhanced by distributing the bulk of the charges close of the "center-region" backbone linkages of the antisense oligonucleotide, e.g., in a 20mer oligonucleotide with 8 cationic backbone linkages, having at least 70% of these charged linkages localized in the 10 centermost linkages.

The antisense compounds can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or for attachment or modification of an antisense oligomer, it is generally of course desirable to select chemical compounds of groups that are biocompatible and likely to be tolerated by a subject without undesirable side effects.

A. Oligomers with Cationic Intersubunit Linkages

This section considers the structures and synthesis of antisense oligonucleotides that are modified, in accordance with one aspect of the invention, to include multiple cationic charges in the backbone linkages. The intersubunit linkages, both uncharged and cationic, preferably are phosphorus-containing linkages, having the structure:

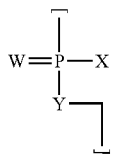

where
W is S or O, and is preferably O,
X=NR$^1$R$^2$ or OR$^6$,
Y=O or NR$^7$,
and each said linkage in the oligomer is selected from:
(a) uncharged linkage (a), where each of R$^1$, R$^2$, R$^6$ and R$^7$ is independently selected from hydrogen and lower alkyl;
(b1) cationic linkage (b1), where X=NR$^1$R$^2$ and Y=O, and NR$^1$R$^2$ represents an optionally substituted piperazino group, such that R$^1$R$^2$=—CHRCHRN(R$^3$)(R$^4$)CHRCHR—, where
each R is independently H or CH$_3$, R$^4$ is H, CH$_3$, or an electron pair, and
R$^3$ is selected from H, lower alkyl, e.g. CH$_3$, C(=NH)NH$_2$, Z-L-NHC(=NH)NH$_2$, and [C(O)CHR'NH]$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;
(b2) cationic linkage (b2), where X=NR$^1$R$^2$ and Y=O, R$^1$=H or CH$_3$, and R$^2$=LNR$^3$R$^4$R$^5$, where L, R$^3$, and R$^4$ are as defined above, and R$^5$ is H, lower alkyl, or lower (alkoxy)alkyl; and
(b3) cationic linkage (b3), where Y=NR$^7$ and X=OR$^6$, and R$^7$=LNR$^3$R$^4$R$^5$, where L, R$^3$, R$^4$ and R$^5$ are as defined above, and R$^6$ is H or lower alkyl;

and at least one said linkage is selected from cationic linkages (b1), (b2), and (b3).

Preferably, the oligomer includes at least two consecutive linkages of type (a) (i.e. uncharged linkages). In further embodiments, at least 5% of the linkages in the oligomer are cationic linkages (i.e. type (b1), (b2), or (b3)); for example, 10% to 60%, and preferably 20-50% linkages may be cationic linkages.

In one embodiment, at least one linkage is of type (b1), where, preferably, each R is H, R$^4$ is H, CH$_3$, or an electron pair, and R$^3$ is selected from H, lower alkyl, e.g. CH$_3$, C(=NH)NH$_2$, and C(O)-L-NHC(=NH)NH$_2$. The latter two embodiments of R$^3$ provide a guanidino moiety, either attached directly to the piperazine ring, or pendant to a linker group L, respectively. For ease of synthesis, the variable Z in R$^3$ is preferably C(O) (carbonyl), as shown.

The linker group L, as noted above, contains bonds in its backbone selected from alkyl (e.g. —CH$_2$—CH$_2$—), alkoxy (—C—O—), and alkylamino (e.g. —CH$_2$—NH—), with the proviso that the terminal atoms in L (e.g., those adjacent to carbonyl or nitrogen) are carbon atoms. Although branched linkages (e.g. —CH$_2$—CHCH$_3$—) are possible, the linker is preferably unbranched. In one embodiment, the linker is a hydrocarbon linker. Such a linker may have the structure —(CH$_2$)$_n$—, where n is 1-12, preferably 2-8, and more preferably 2-6.

The morpholino subunits have the structure:

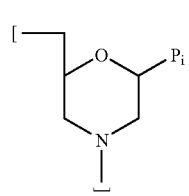

(i)

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) and (b3) above to link morpholino subunits may be illustrated graphically as follows:

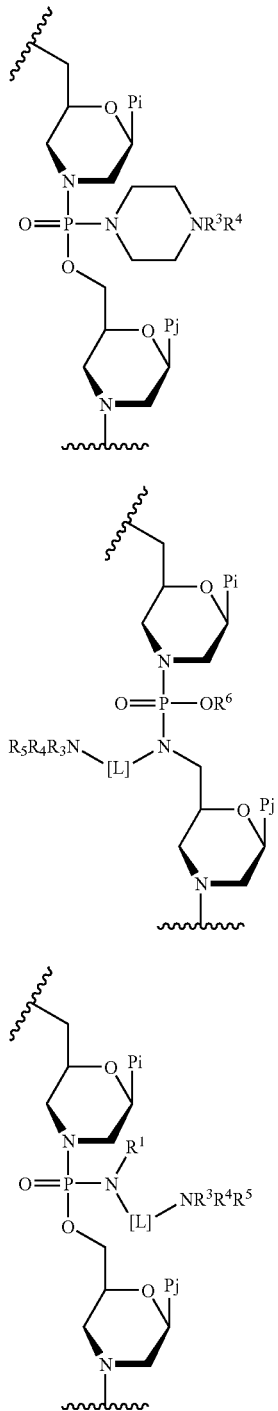

Preferably, all cationic linkages in the oligomer are of the same type; i.e. all of type (b1), all of type (b2), or all of type (b3).

In further embodiments, the cationic linkages are selected from linkages (b1') and (b1") as shown below, where (b1") is referred to herein as a "Pip" linkage and (b1"') is referred to herein as a "GuX" linkage:

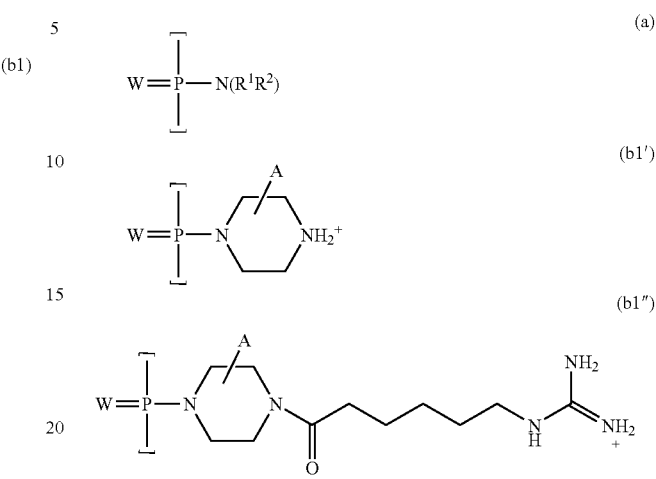

In the structures above, W is S or O, and is preferably O; each of $R^1$ and $R^2$ is independently selected from hydrogen and lower alkyl, and is preferably methyl; and A represents hydrogen or a non-interfering substituent on one or more carbon atoms in (b1') and (b1"). Preferably, the ring carbons in the piperazine ring are unsubstituted; however, they may include non-interfering substituents, such as methyl or fluorine. Preferably, at most one or two carbon atoms is so substituted.

In further embodiments, at least 10% of the linkages are of type (b1') or (b1"); for example, 10%-60% and preferably 20% to 50%, of the linkages may be of type (b1') or (b1").

In other embodiments, the oligomer contains no linkages of the type (b1') above. Alternatively, the oligomer contains no linkages of type (b1) where each R is H, $R^3$ is H or $CH_3$, and $R^4$ is H, $CH_3$, or an electron pair.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5'nitrogen atom on a morpholino ring could be employed in a sulfamide linkage (see e.g. FIG. 2G) or a urea linkage (where phosphorus is replaced with carbon or sulfur, respectively) and modified in a manner analogous to the 5'-nitrogen atom in structure (b3) above.

Oligomers having any number of cationic linkages are provided, including fully cationic-linked oligomers. Preferably, however, the oligomers are partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 10 to 25 subunits, and typically 10-20 bases. For example, an oligomer of the invention having 19-20 subunits, a useful length for an antisense oligomer, may ideally have two to ten, e.g. four to eight, cationic linkages, and the remainder uncharged linkages. An oligomer having 14-15 subunits may ideally have two to five, e.g. 3 or 7, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (A, G, C, T, or U) or an analog, such as hypoxanthine (the base component of the nucleoside inosine) or 5-methyl cytosine.

B. Carrier Peptides

This section considers the structures and synthesis of antisense oligonucleotides that are modified, in accordance with another aspect of the invention, to include an arginine-rich carrier peptide which enhances the antibacterial activity of the oligonucleotide, at least in part, by enhances transport of the oligomer into bacterial cells. The transport moiety is preferably attached to a terminus of the oligomer, as shown, for example, in FIGS. 2P-2Q.

Preferably, the transport moiety comprises 6 to 16, preferably 8-14, amino acids and is composed of subsequences selected from the group represented by (X'Y'X'), (X'Y'), (X'Z'), and (X'Z'Z'), where (a) each X' subunit independently represents lysine, arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y' subunit independently represents a neutral linear amino acid $—C(O)—(CHR)_m—NH—$, where m is 1 to 7 and each R is independently H or methyl; and (c) each Z' subunit independently represents an α-amino acid having a neutral aralkyl side chain.

As used herein, a carrier protein is "composed of the subsequences selected from the group represented by X'Y'X', X'Y', X'Z'Z' and X'Z'" if substantially all of its amino acids can be represented by a non-overlapping series of the subsequences, or positional variations thereof, e.g., $(X'X'Y')_n$, $(X'Y'X')_n$, $(Y'X'X')_n$, $(Y'X')_n$, $(X'Y')(X'X'Y')(X'Y')(X'X'Y')$, $(X'Y')_n(X'X'Y')_m$, $(X'FF)_n$ or $(FFX')_n$. The protein may accommodate a small number, e.g., 1-3, of neutral amino acids other than Y or Z.

In selected embodiments, the peptide comprises a sequence which consists of at least two, or at least three, repeats of a single subsequence selected from (X'Y'X'), (X'Y'), (X'Z'), and (X'Z'Z'). For example, the peptide may comprise a sequence represented by one of $(X'Y'X')_p$, $(X'Y')_m$, and $(X'Z'Z')_p$, where p is 2 to 5 and m is 2 to 8.

In selected embodiments, for each X', the side chain moiety is independently selected from the group consisting of guanidyl ($HN=C(NH_2)NH—$), amidinyl ($HN=C(NH_2)C<$), 2-aminodihydropyrimidyl, 2-aminotetrahydropyrimidyl, 2-aminopyridinyl, and 2-aminopyrimidonyl, and it is preferably selected from guanidyl and amidinyl.

In preferred embodiments, for each X', the side chain moiety is guanidyl, as in the amino acid subunit arginine (Arg). In further embodiments, each Y' is $—CO—(CH_2)_m—R—NH—$, where m is 1 to 7 and R is H. For example, when m is 5 and R is H, Y' is a 6-aminohexanoic acid subunit, abbreviated herein as Ahx; when m is 2 and R is H, Y' is a β-alanine subunit.

The aralkyl side chain of the Z' subunit is preferably benzyl ($—CH_2C_6H_6$) or phenethyl ($—CH_2CH_2C_6H_6$), which are preferably not further substituted but may include a non-interfering substituent as defined herein. Preferably, the side chain is benzyl ($—CH_2C_6H_6$), such that each Z' is phenylalanine (F).

One type of preferred peptides of this type include those comprising arginine dimers alternating with single Y' subunits, where Y' is preferably Ahx. Examples include peptides having the formula $(RY'R)_4$ or the formula $(RRY')_4$, where Y' is preferably Ahx. In one embodiment, Y' is a 6-aminohexanoic acid subunit, R is arginine, and p is 4. In a further embodiment, the peptide comprises a sequence represented by $(X'Z'Z')_p$, where R is arginine, each Z' is phenylalanine, and p is 3 or 4.

The conjugated peptide is preferably linked to a terminus of the oligomer via a linker Ahx-B, where Ahx is a 6-aminohexanoic acid subunit and B is a β-alanine subunit. The Y' subunits are either contiguous, in that no X' subunits intervene between Y' subunits, or interspersed singly between X' subunits. However, the linking subunit may be between Y' subunits. In one embodiment, the Y' subunits are at a terminus of the transporter; in other embodiments, they are flanked by X' subunits.

In addition to enhanced uptake, the carrier peptide may help to stabilize a heteroduplex between an antisense oligomer and its target nucleic acid sequence, by virtue of electrostatic interaction between the positively charged transport moiety and the negatively charged nucleic acid. The number of charged subunits in the transporter is less than 14, as noted above, and preferably between 6 and 11, since too high a number of charged subunits may lead to a reduction in sequence specificity.

Exemplary peptide transporters, including linkers (B or AhxB) are given below:

| Peptide | Sequence (N-terminal to C-terminal) | SEQ ID NO: |
|---|---|---|
| (RRAhx)<sub>4</sub>B | RRAhxRRAhxRRAhxRRAhxB | 99 |
| (RAhxR)<sub>4</sub>AhxB | RAhxRRAhxRRAhxRRAhxRAhxB | 100 |
| (AhxRR)<sub>4</sub>AhxB | AhxRRAhxRRAhxRRAhxRRAhxB | 101 |
| (RAhx)<sub>6</sub>B | RAhxRAhxRAhxRAhxRAhxRAhxB | 102 |
| (RAhx)<sub>8</sub>B | RAhxRAhxRAhxRAhxRAhxRAhxRAhxRAhxB | 103 |
| (RAhxR)<sub>3</sub>AhxB | RAhxRRAhxRRAhxR AhxB | 104 |
| (RAhxRRBR)<sub>2</sub>AhxB | RAhxRRBRRAhxRRBRAhxB | 105 |
| ((RB)3RAhx)2B | RBRBRBRAhxRBRBRBRAhxB | 106 |

C. Preparation of Oligomers Having Cationic Intersubunit Linkages

Figure 2A:
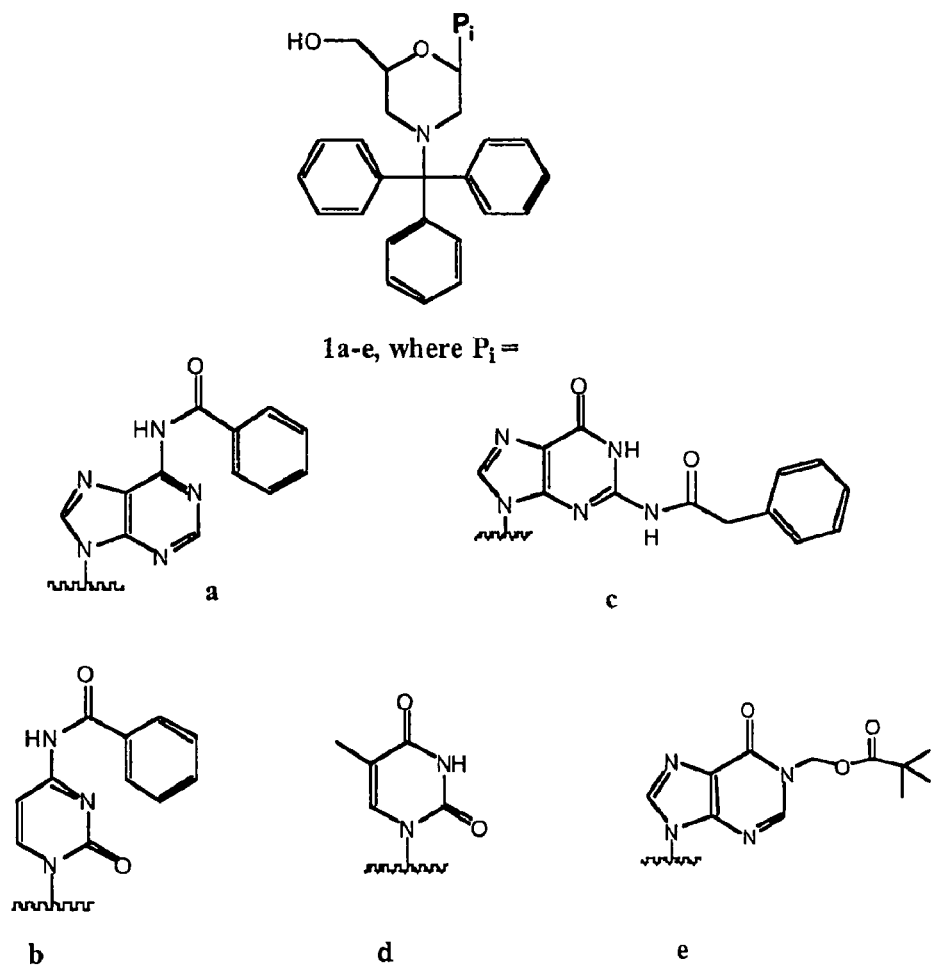
FIG. 2A shows representative morpholino subunits 1a-e with protected recognition moieties $P_i$ of A, C, G, T, and 1.
Figure 2B:
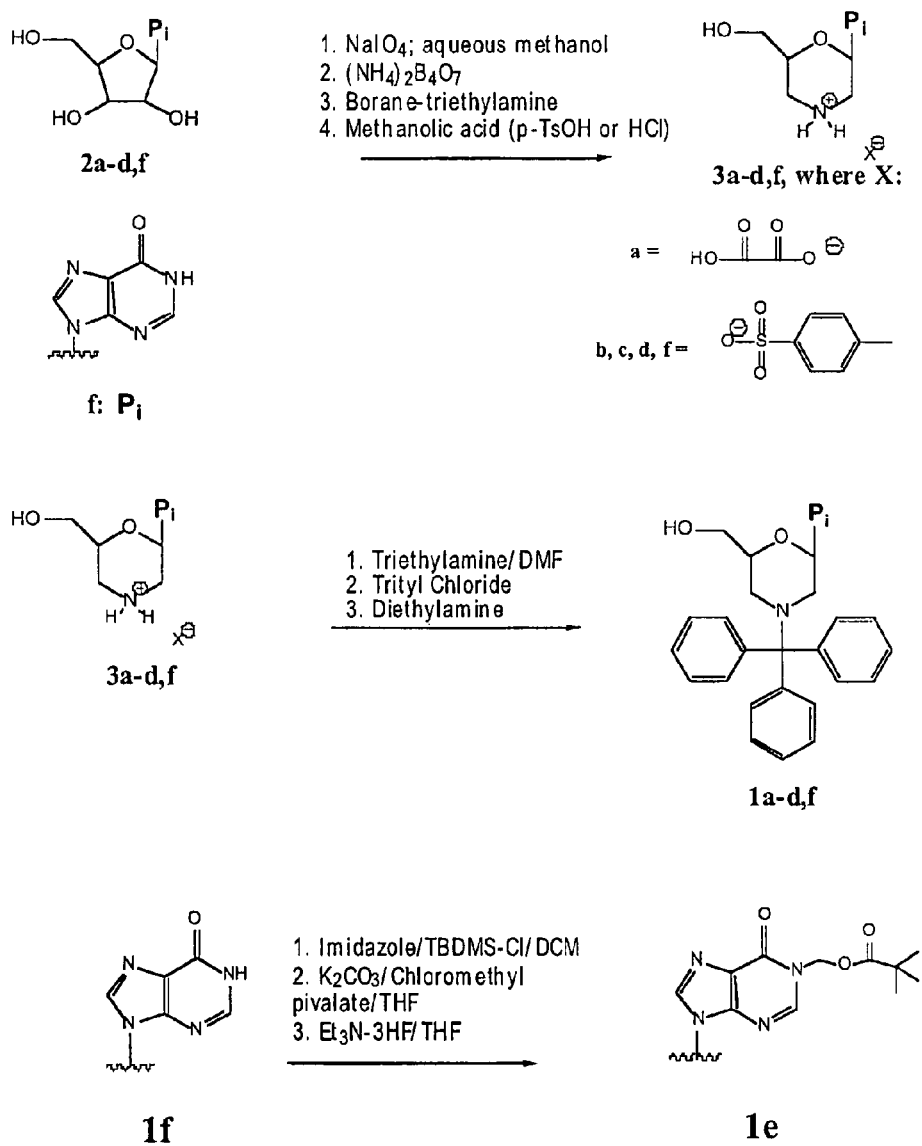
FIG. 2B shows synthetic schemes for preparation of the subunits of FIG. 2A from the corresponding ribonucleosides.
Figure 2C:
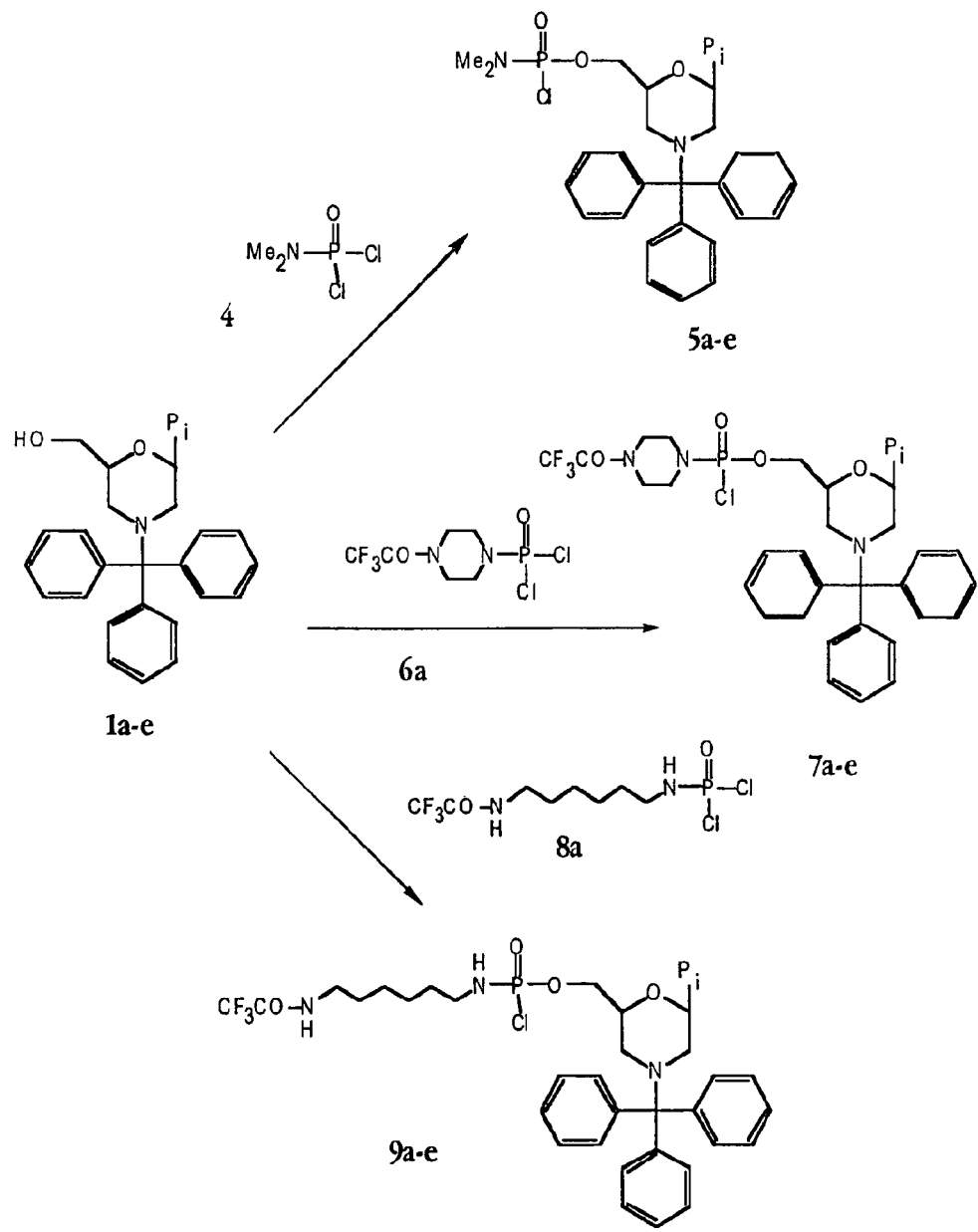
FIG. 2C illustrates the preparation of activated, protected subunits for preparation of linkage type (a) (uncharged) and linkage types (b1) and (b2) (charged) as designated herein.
Figure 2D:
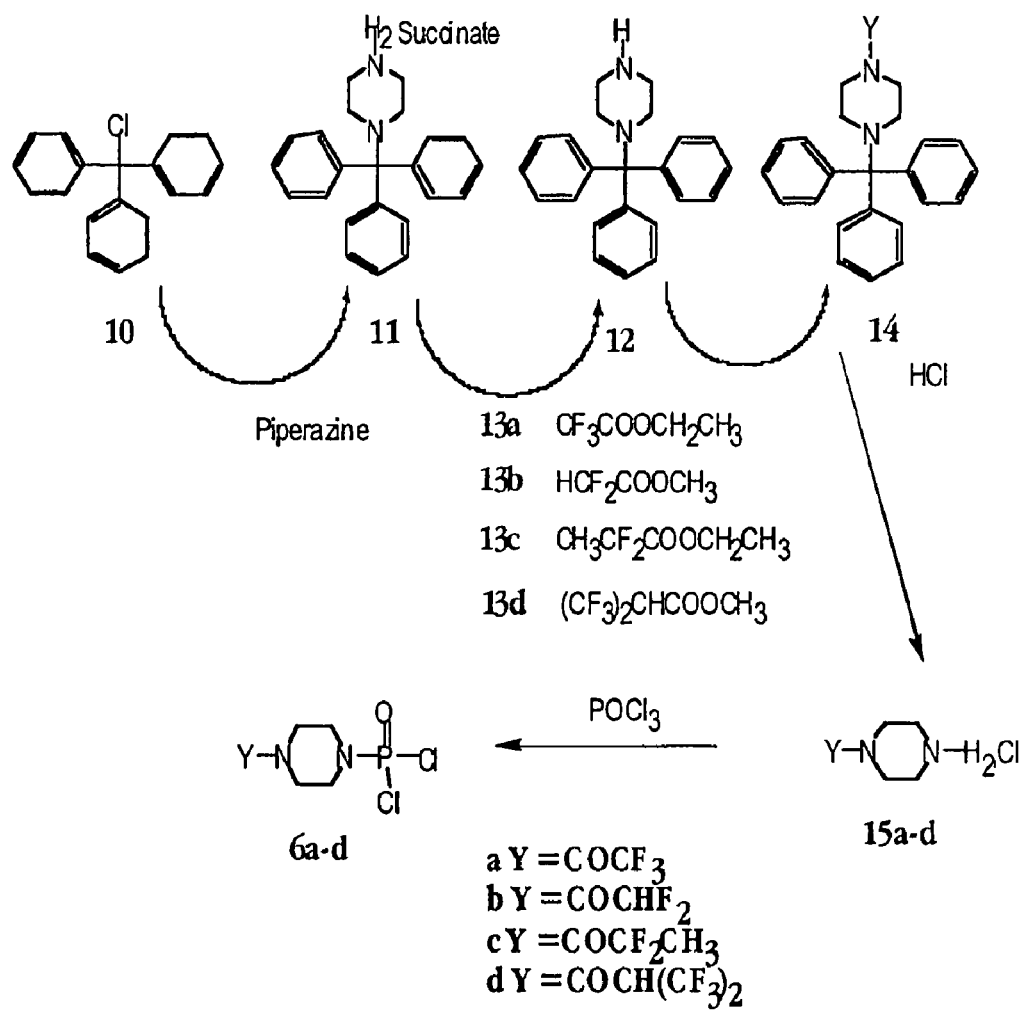
FIG. 2D is a schematic of a synthetic pathway that can be used to make morpholino subunits containing the (1-piperazino) phosphinylideneoxy ("Pip") linkage.
Figure 2E:
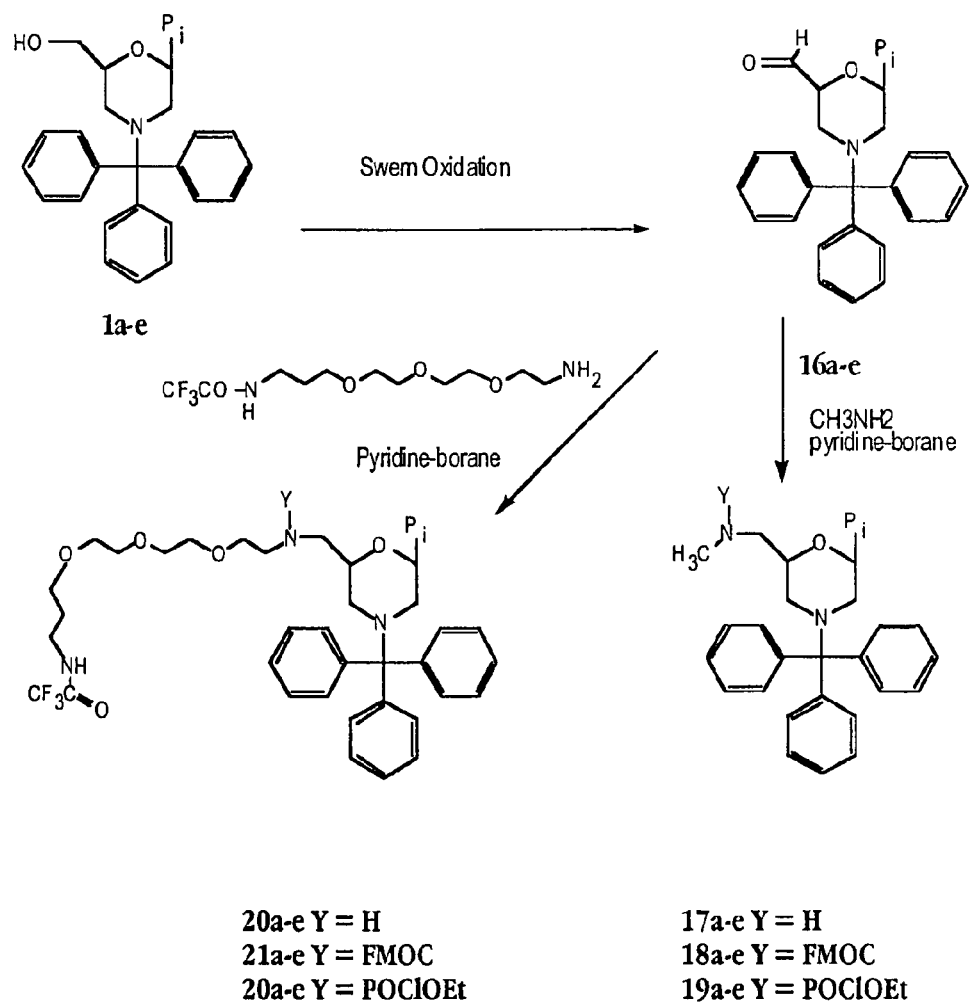
FIGS. 2E and 2F illustrate the preparation of activated, protected subunits for preparation of linkages of type (b3) (charged) as designated herein.
Figure 2F:
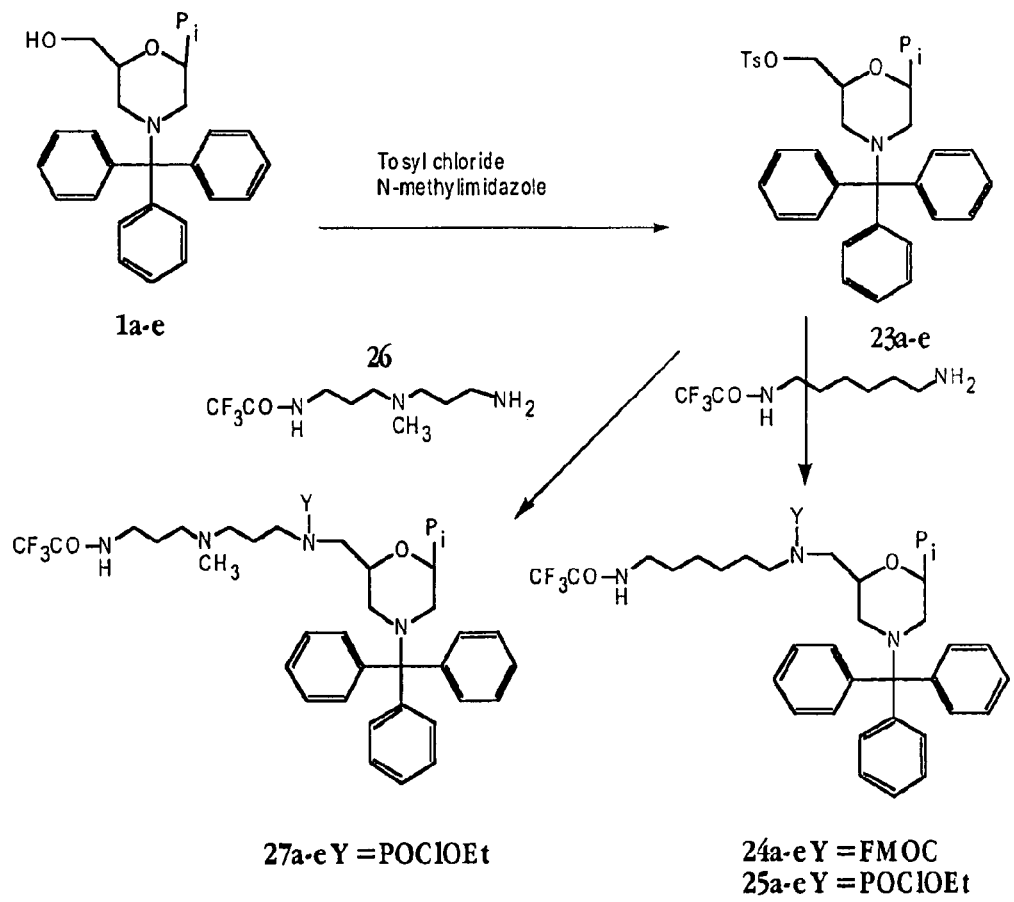
Figure 2G:
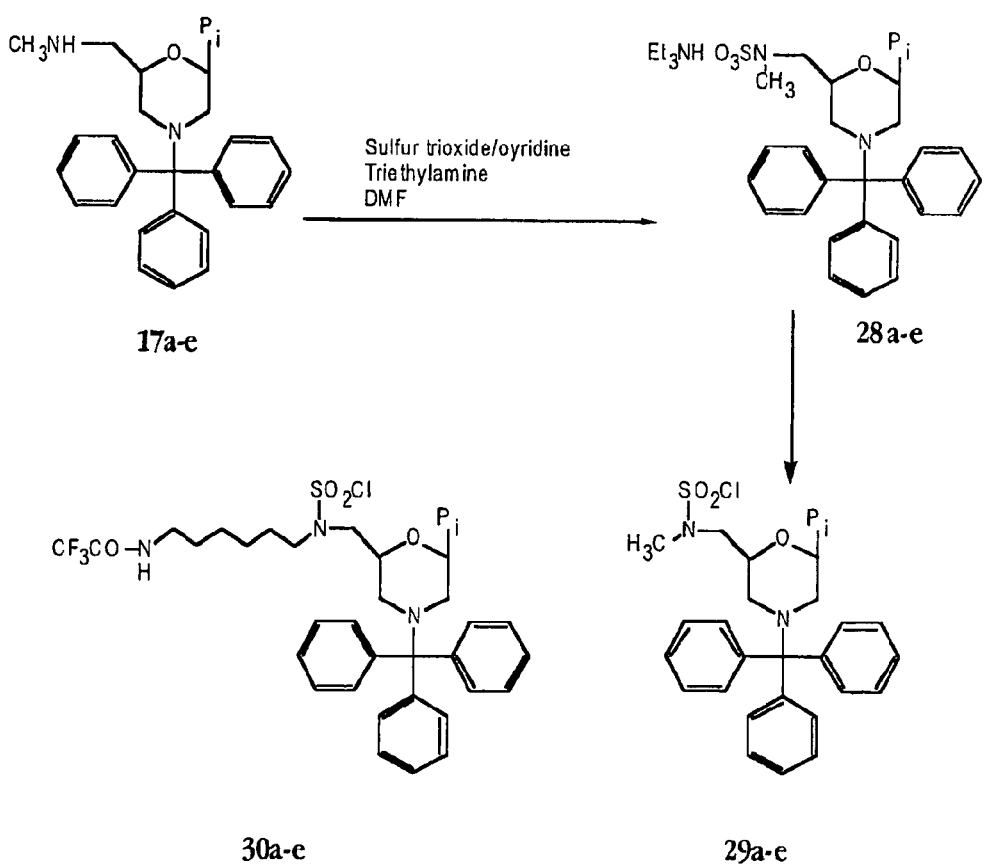
FIG. 2G illustrates the preparation of subunits that can be used to prepare linkages analogous to type (b3) (charged) but based on non-phosphorus-containing linkages, specifically sulfonamide linkages.
Figure 2H:
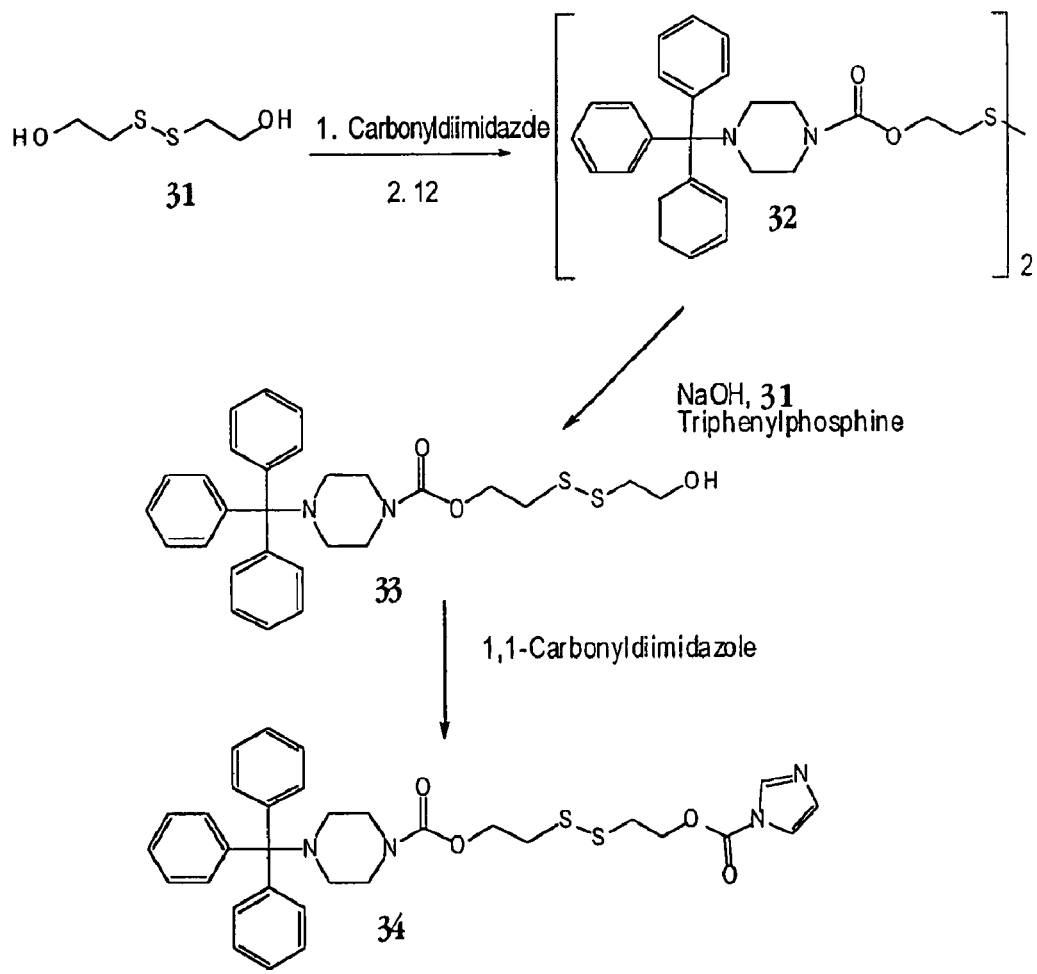
FIG. 2H illustrates preparation of a disulfide anchor, for use in modification of a synthesis resin used for stepwise preparation of a morpholino oligomer, allowing facile release of the oligomer by treatment with a thiol.
Figure 2I:
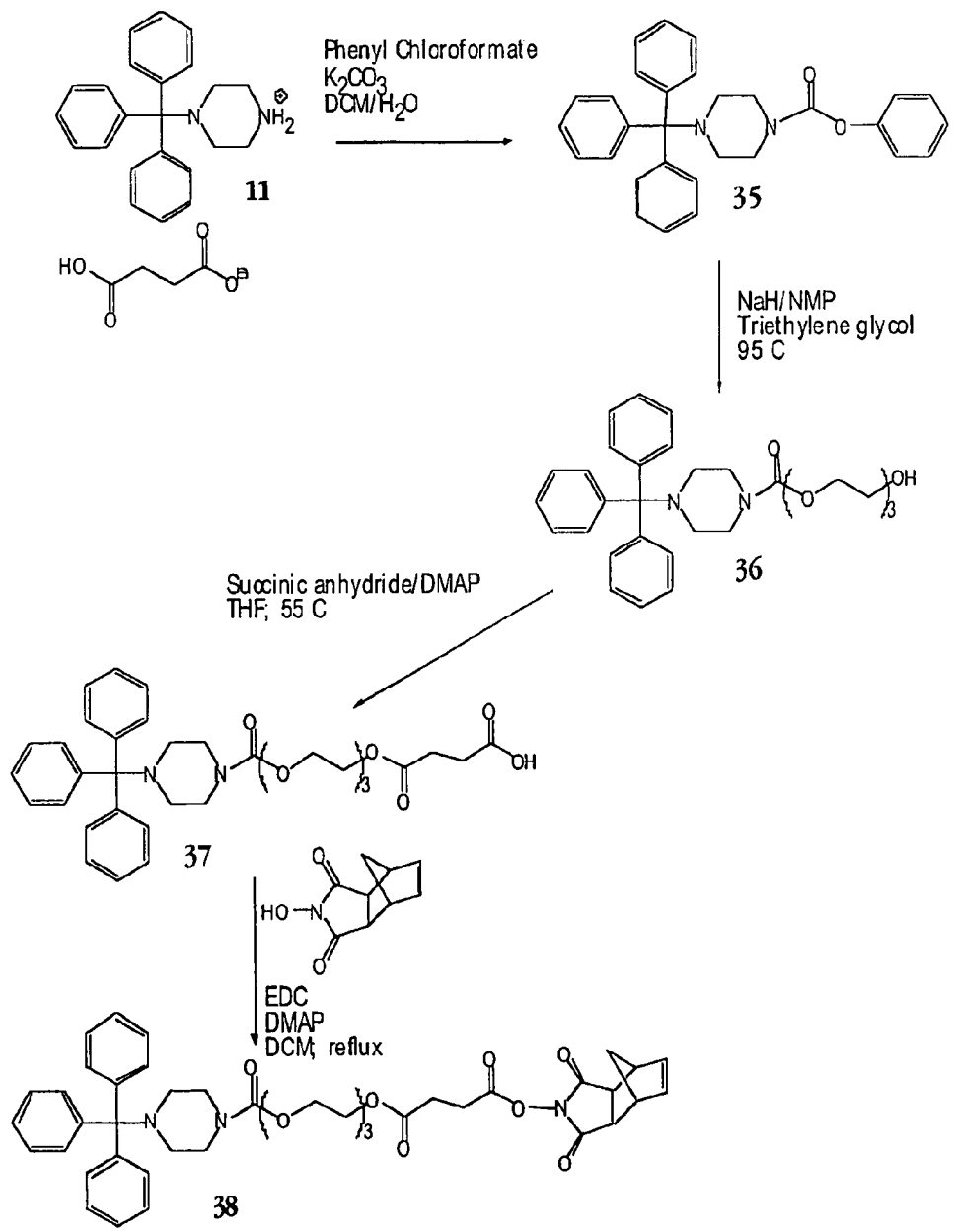
FIG. 2I illustrates the introduction a triethylene glycol containing moiety ("Tail") which increases aqueous solubility of synthetic antisense oligomers.
Figure 2J:
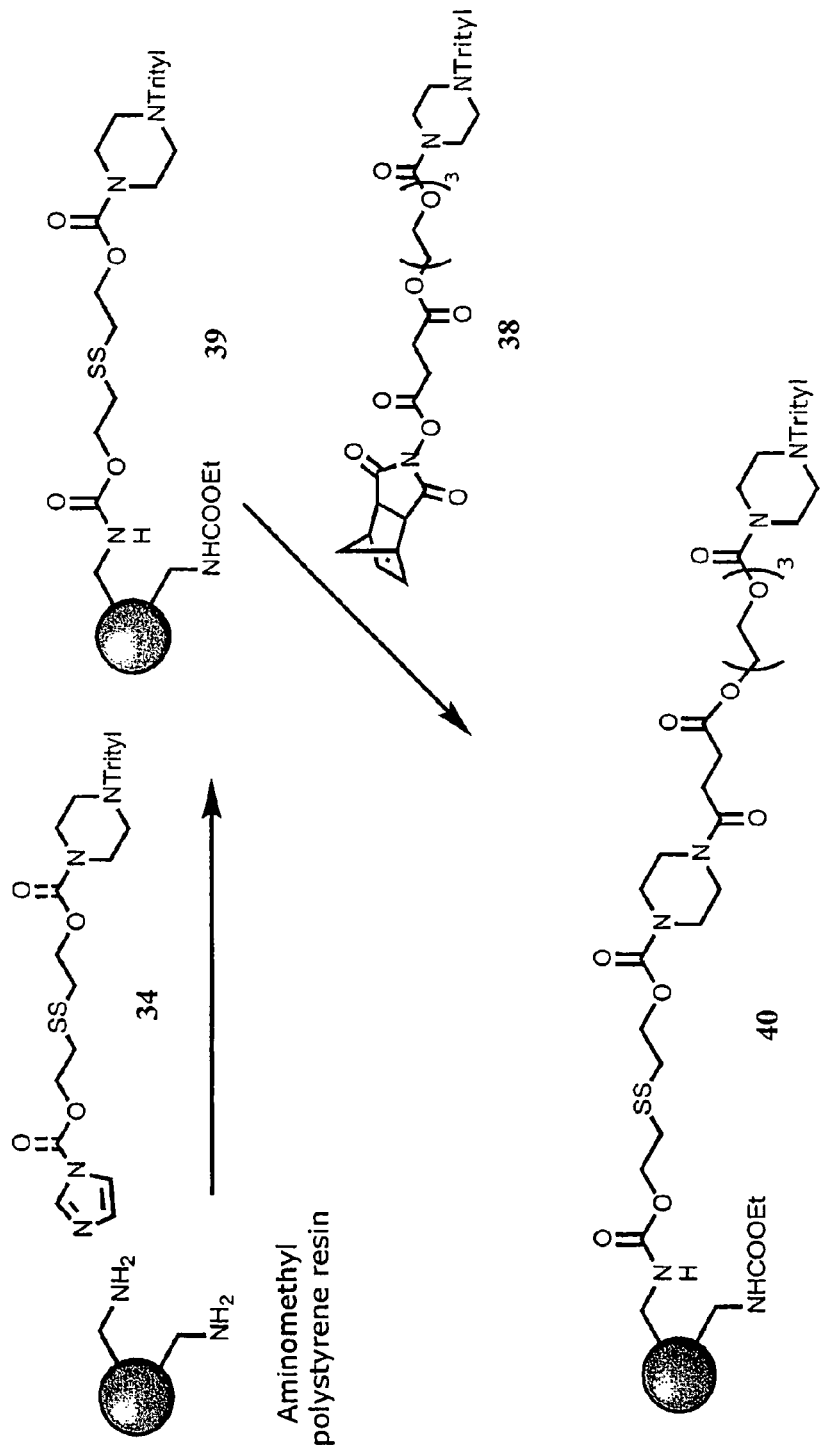
FIG. 2J illustrates the preparation of resins useful for the solid phase synthesis of morpholino oligomers.
Figure 2K:
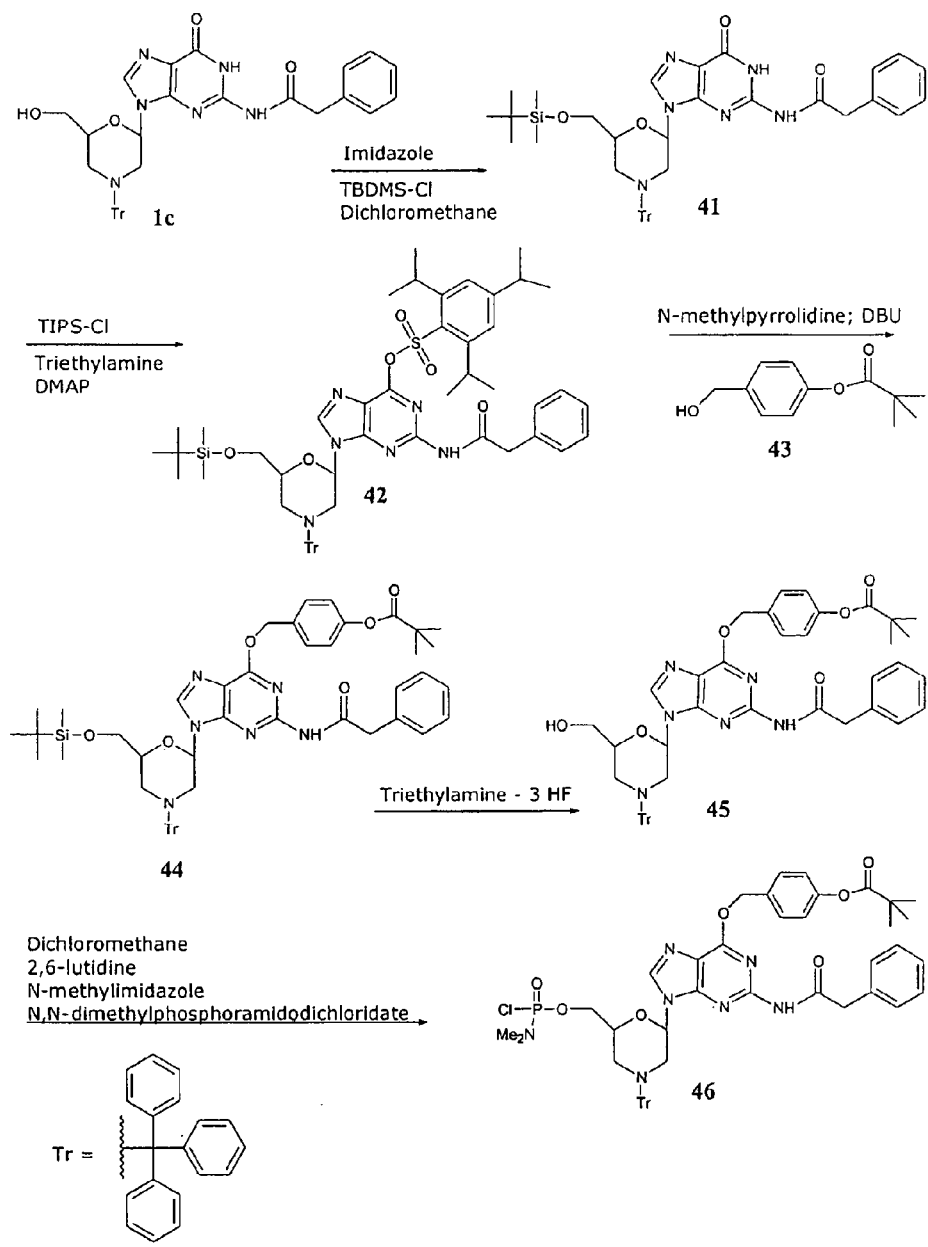
FIG. 2K illustrates the preparation of N2, O6-protected morpholino G Subunit for large scale oligomer synthesis
Figure 2L:
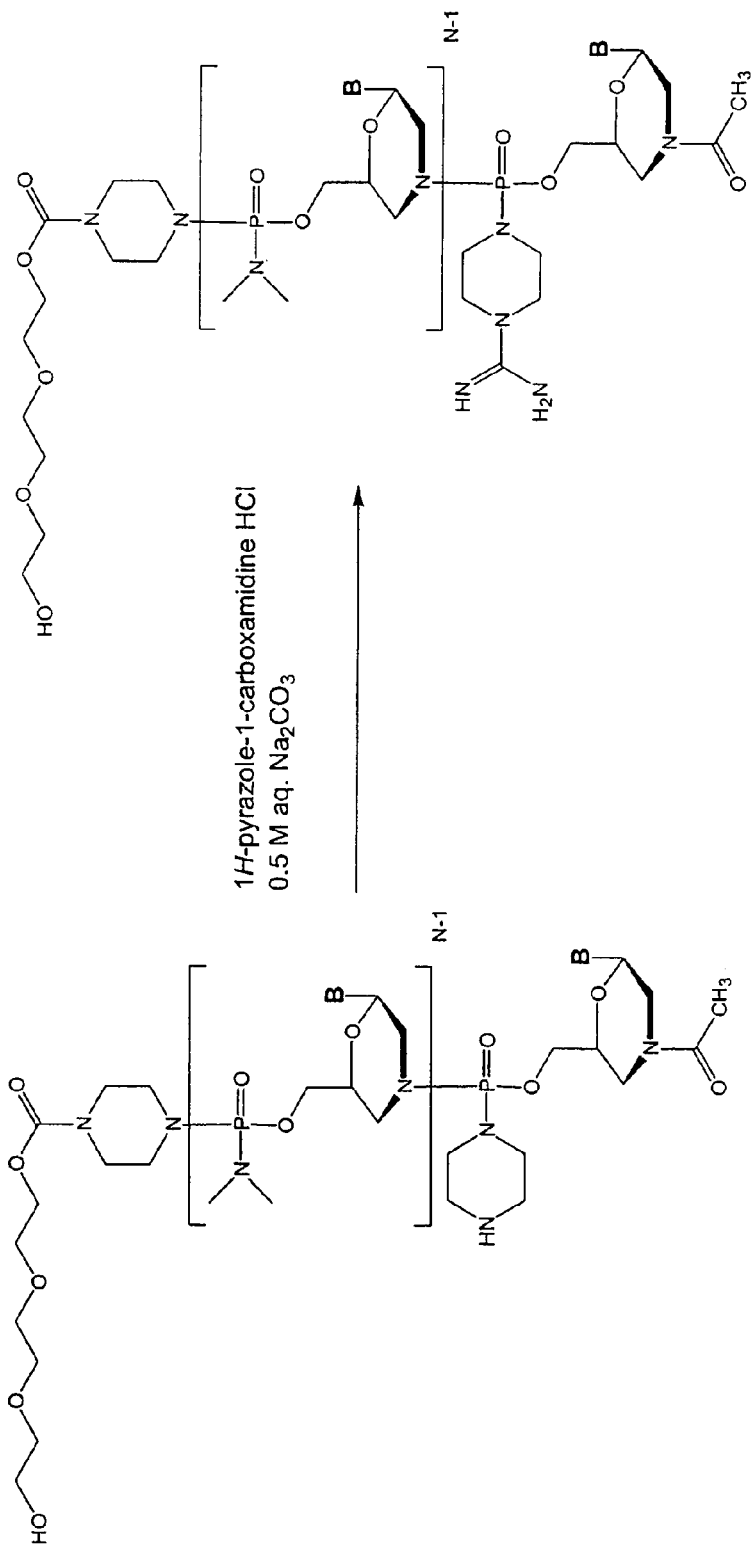
FIG. 2L illustrates the introduction of guanidinium groups by direct guanylation of amines on the morpholino oligomer.
Figure 2M:
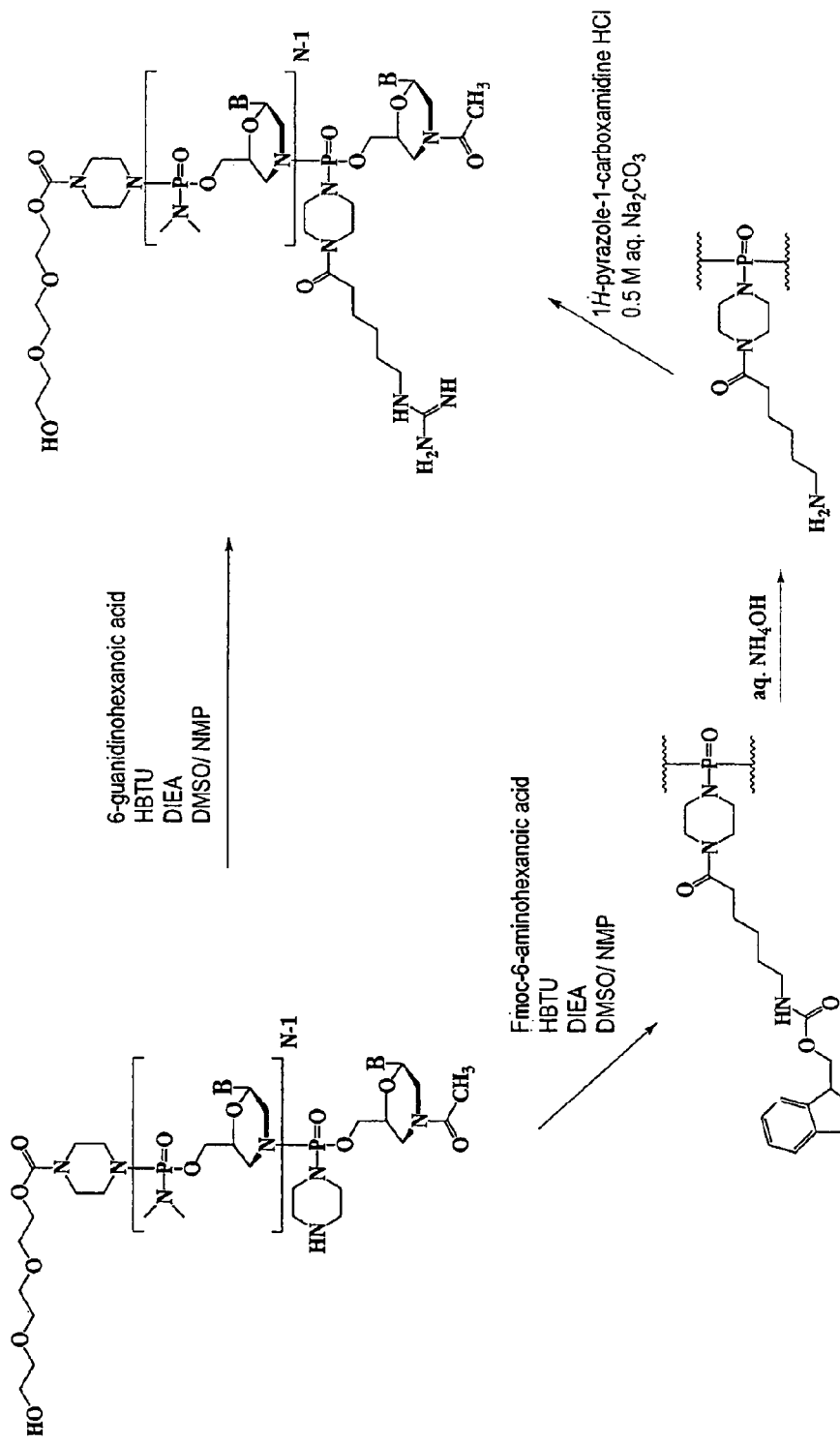
FIG. 2M illustrates the introduction of guanidinium groups into morpholino oligomers by incorporation of amino acids and guanidino acids.
Figure 2N:
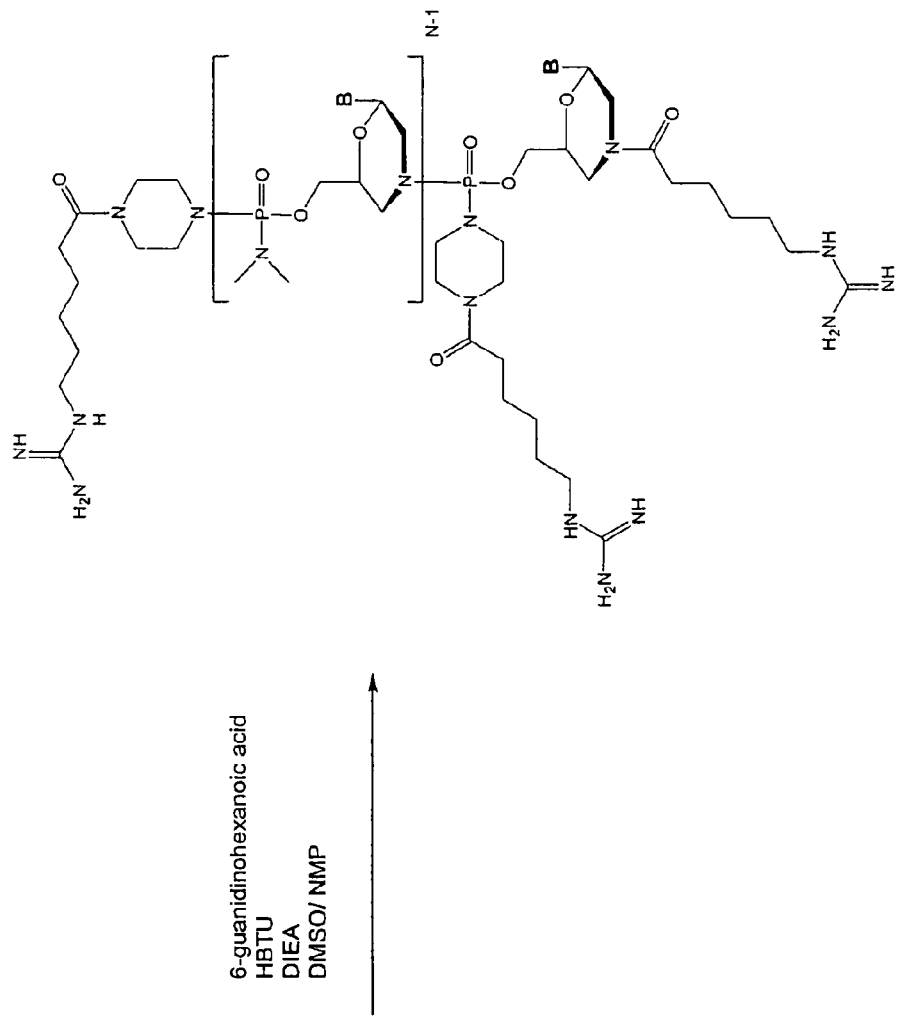
FIG. 2N illustrates the introduction of guanidinium groups into morpholino oligomers by incorporation of guanidino acids at both backbone and terminal positions.
Figure 2N:
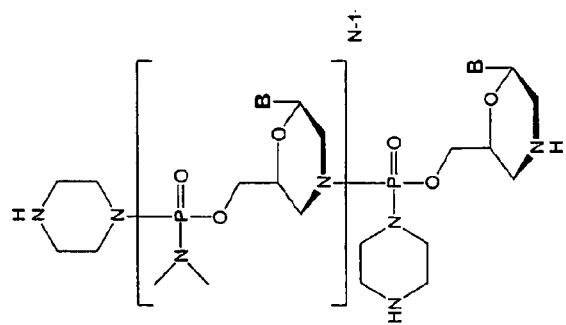
Figure 2P:
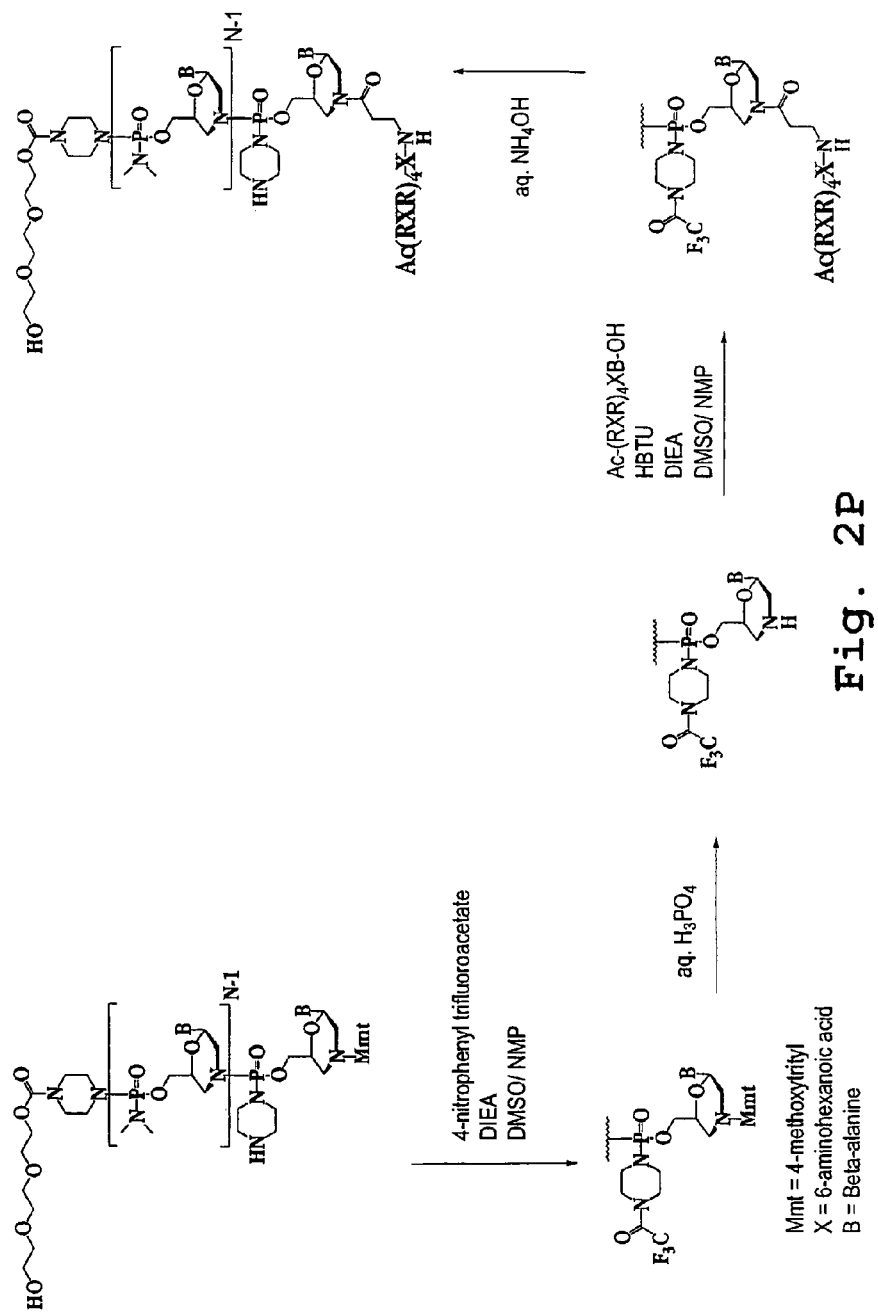
FIG. 2P illustrates the introduction of a transport peptides at the 3'-terminus of morpholino oligomers having charged groups of linkage type b1 in the backbone.
Figure 2Q:
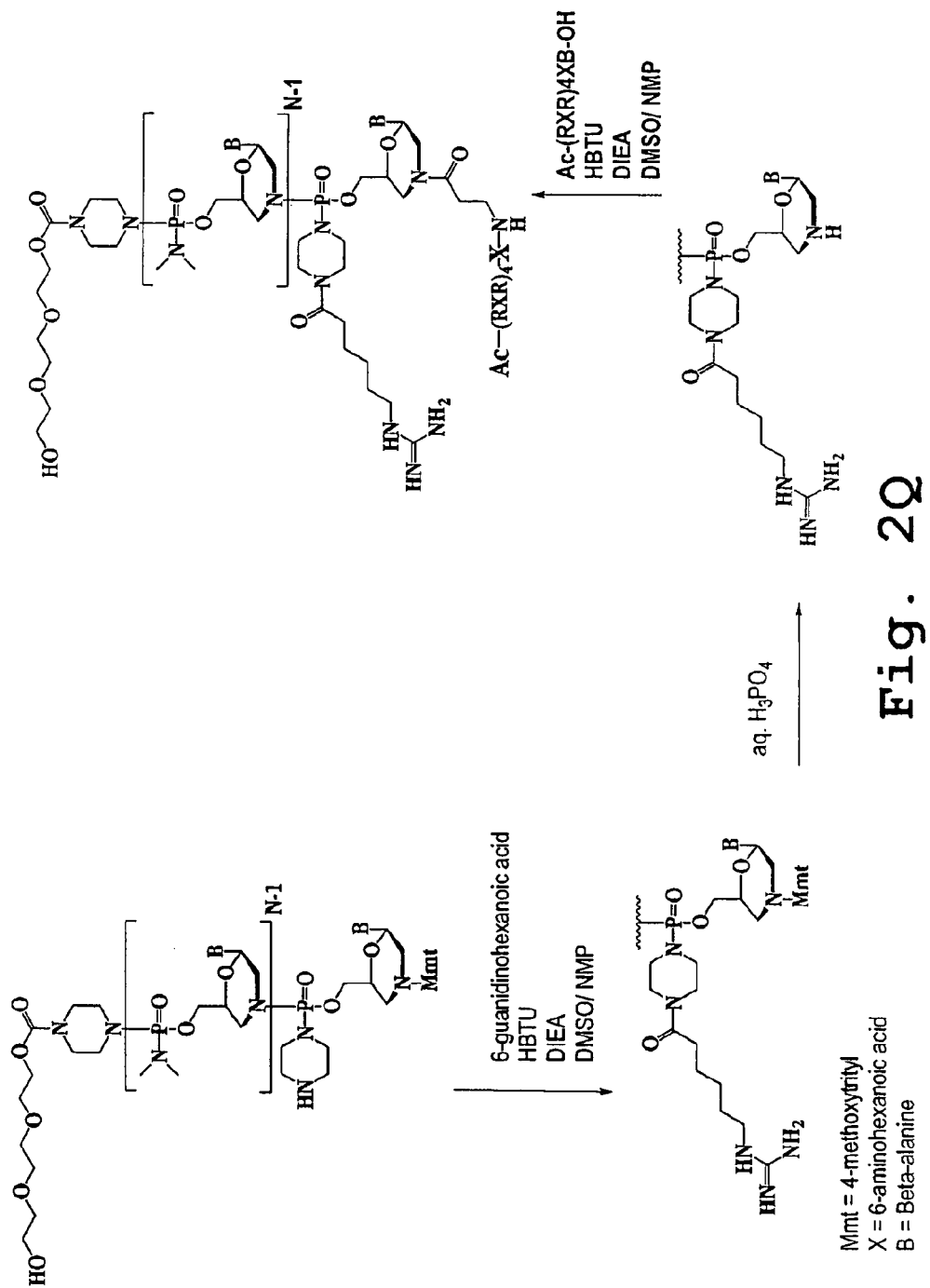
FIG. 2Q illustrates the introduction of a transport peptides at the 3'-terminus of morpholino oligomers having GuX linkages in the backbone.
Figure 2R:
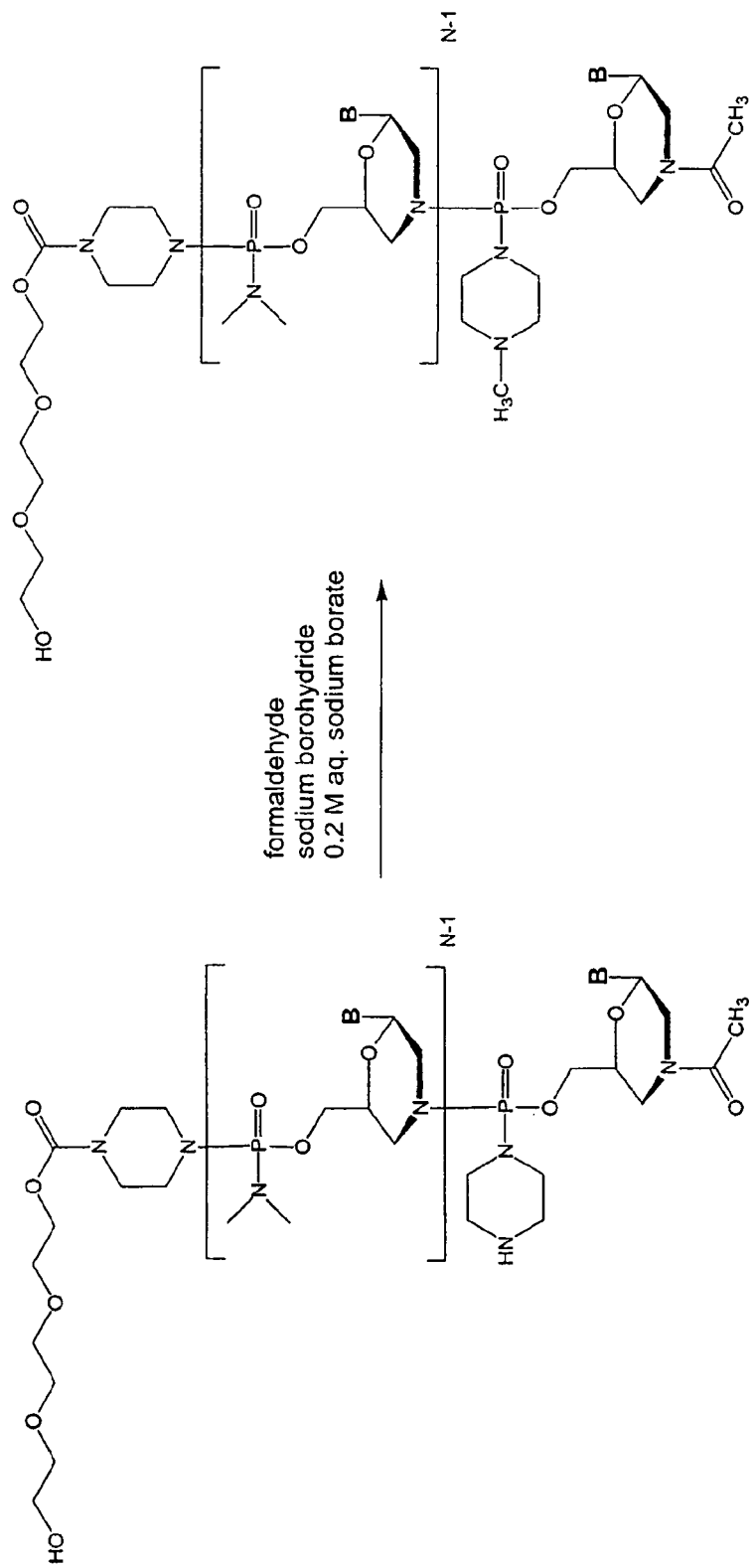
FIG. 2R illustrates the reductive alkylation of amines of morpholino oligomers.

FIGS. 2A through 2R illustrate the preparation of morpholino subunits having suitably protected base-pairing groups, and the conversion of these subunits into morpholino oligomers having cationic linkages. Further experimental detail is provided in Materials and Methods, below. The charged-linkage subunits can be used in standard stepwise oligomer synthesis, as described, for morpholino oligomers, in U.S. Pat. No. 5,185,444 or in Summerton and Weller, 1997 (cited above).

FIG. 2A shows representative morpholino subunits 1a-e with base-pairing moieties Pi of A, C, G, T, and I. These subunits can be prepared from the corresponding ribonucleosides as illustrated in FIG. 2B and described in Example 1. Suitable protecting groups are used for the nucleoside bases, where necessary; for example, benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base as shown in FIG. 2B. Although an unprotected hypoxanthine subunit, as in 1f, may be employed, yields in activation reactions are far superior when the base is protected.

Treatment of the 5'-hydroxy (1) with a reactive acid chloride, such as N,N-dimethylphosphoramidodichloridate (4), provides type (a) (uncharged linkage) activated subunits 5a-e, as shown in FIG. 2C and described in Example 2. Although the unprotected hypoxanthine containing subunit, as in 1f, may be employed, yields in activation reactions are far superior when the base is protected.

FIG. 2C also illustrates the use of alternate reactive acid chlorides, such as 6a, to convert 5'-hydroxy subunits 1a-e into type (b1) (charged linkage) activated subunits 7a-e.

Similarly, an acyclic reactive acid chloride, such as 8a, can be used to convert 5'-hydroxy subunits 1a-e into type (b2) (charged linkage) activated subunits 9a-e. These charged-linkage subunits may be incorporated into phosphorodiamidate-linked morpholino oligomers and, upon treatment with the usual reagents that remove the base protecting groups, preferably ammonia, produce oligomers containing type (b1) and (b2) cationic phosphorodiamidate linkages.

A schematic of a synthetic pathway that can be used to make morpholino subunits containing the (1-piperazino) phosphinylideneoxy linkage (type b1'; "Pip") is shown in FIG. 2D and described in Example 3. Reaction of piperazine and trityl chloride 10 gives trityl piperazine, which can be isolated as the succinate salt 11. Reaction with ethyl trifluoroacetate 13a in the presence of a weak base, e.g. diisopropylethylamine, provides 1-trifluoroacetyl-4-trityl piperazine 14, which upon treatment with HCl provide the detritylated salt 15 in good yield. Introduction of the dichlorophosphoryl moiety on the free eing nitrogen was performed with phosphorus oxychloride in toluene, yielding the piperazine-P(O)Cl$_2$ moiety 6a. This reagent can be reacted with 5'-hydroxy morpholino subunits to produce activated subunits containing the protected (1-piperazino) phosphinylideneoxy linkage, which can be incorporated into oligomers using the oligomer synthesis protocol below.

Selectively protected acyclic amines, suitable for incorporation into morpholino subunits for the preparation of type (b2) cationic linkages, may be prepared by methods analogous to that described and illustrated for the cyclic amines; see Example 4. Alternatively, treatment of a solution of a diamine with 1.6 equivalents of the reactive ester 13a-d provides a solution with <5% of the free diamino species. The solution was used directly for activation with POCl$_3$ and activation of the morpholino subunits 1a-e. A person skilled in the art would find it possible to prepare oligomers with more complex cationic sides chains using the methods above.

Subunits for the introduction of type (b3) cationic linkages, i.e. having a nitrogen at the 5'-position, into oligomers may be prepared, as shown in FIG. 2E and described in Example 5, by oxidation of a morpholino subunit to the corresponding aldehyde (16a-e) and reductive amination with a suitably protected diamine, which affords a representative 5'-aminomorpholino subunit 20a-e. It is often preferable to isolate the amine as the 9-fluorenylmethyloxycarbonyl (FMOC) derivative 21a-e following treatment with FMOC chloride. The free amine can be easily regenerated when needed by treatment with triethylamine or 1,8-diazabicyclo[5.4.0]undec-7-ene (DBU). Activation of the amine with ethyl phosphorodichloridate gives type (b3) activated subunits 22a-e, which can be incorporated into oligomers in the same manner as type (a), (b1) and (b2) subunits.

A method for the preparation of variants of 22a-e, containing various side chains on the 5'-nitrogen, involves alkylation of an activated 5'-morpholino subunit with suitably protected amines. As shown in FIG. 2F for two examples, and described in Example 6, hexamethylene diamine was first protected, then reacted with 5'-O-p-toluenesulfonated subunit 23a-e. Using the methods in FIGS. 2E and 2F and in the corresponding Examples, a person skilled in the art could prepare a wide range of 5'-amino substituted subunits suitable for incorporation into cationic morpholino oligomers.

As noted above, cationic linkages may also be prepared from non-phosphorus-containing linkages. For example, subunits capable of providing sulfonamide linkages with pendant cationic groups may be introduced from the amine used in (b3) type linkages, as shown in FIG. 2G and described in Example 7. Reaction of the aminated subunits with sulfurtrioxide/pyridine in N,N-dimethylformamide containing triethylamine provides a sulfamic acid that was treated with phosgene in dichloromethane containing pyridine to give the activated sulfamoyl chloride containing subunit.

Morpholino oligomers can be prepared from such subunits in a stepwise manner on a solid support, preferably an aminomethyl polystyrene solid support, e.g. as described in U.S. Pat. No. 5,185,444 or in Summerton and Weller, 1997 (cited above). The resin is preferably modified by reaction with a disulfide "anchor", which allows production of the morpholino oligomer on the support and facile release upon treatment with a thiol, as shown in FIG. 2H and described in Example 8.

In some cases it is advantageous to introduce a triethylene glycol containing moiety ("tail") which increases aqueous solubility of the morpholino oligomers. One method for accomplishing this is illustrated in FIG. 2I and described in Example 9.

In a typical synthesis, the disulfide anchor 34 is reacted as shown in FIG. 2J with aminomethylpolystyrene resin in 1-methyl-2-pyrrolidinone (NMP) to give resin-anchor 39, suitable for incorporation of activated subunits. Optionally, the Tail moiety can be introduced onto the 5'-terminus of the oligomer by reaction of the disulfide anchor-resin with 38 to produce Tail-resin 40. Use of resin 40 will cause the HOCH$_2$CH$_2$OCH$_2$CH$_2$OCH$_2$CH$_2$OC(O) group (=EG3) to become attached to the 5'-terminus of the oligomer.

The activated subunits, containing the appropriate intersubunit linkage type, are introduced stepwise by solid phase synthesis on resin 39 containing anchor or, optionally, the Tail resin 40. A cycle of solid phase synthesis performed using an automated synthesizer consists of washing the resin with NMP or dichloromethane (DCM), followed by treatment with 11% cyanoacetic acid in 20% acetonitrile/DCM (v/v). After neutralization with a 5% solution of diisopropylethylamine (DIEA) in 20% isopropanol/DCM, the resin is reacted with a 0.2 M solution of the activated subunit in 1,3-dimethyl-2-imidazolidinone (DMI) (or Tail in NMP) containing 0.4 M 4-ethylmorpholine. After washing with neutralization solution, the cycle may be repeated to introduce the next subunit.

Optionally, following the final subunit addition, the trityl group at the end of the resin is removed and methoxytrityl chloride introduced to prepare the 3'-methoxytritylated oligomer. The more labile methoxytrityl species provides benefit in the aqueous detritylation step which follows "trityl-ON/trityl-OFF" purification of the crude oligomers.

The reactor design used for the preparation of the bulk resins 39 and 40 was employed for larger scale synthesis of morpholino oligomers. On the large scale, the detritylation steps performed when phosphorodiamidate linkages had been introduced onto the resin used a solution of 4-cyanopyridinium trifluoroacetate in 20% trifluoroethanol/DCM. This provided less hydrolysis of the somewhat acid labile phosphorodiamidate linkages than did carboxylic acid based detritylation reagents. Additionally, the use of doubly protected G subunit was found to be advantageous. FIG. 2K illustrates synthesis of the N2,O6-protected G species 46 that was employed.

The synthesized oligomers were released from the solid support by treatment with a solution of 1,4-dithiothreitol and triethylamine in NMP. The solution was treated with concentrated ammonia and held at 45° C. The mixture was sealed in a pressure vessel and heated at 45° C. for 16-24 hours. The solution was diluted with 0.28% aqueous ammonia and passed through ion exchange resin to capture the crude methoxytritylated oligomer. The product was eluted with a salt gradient to recover the later-eluting, methoxytrityl or trityl containing product and the product containing fractions pooled. For preparation of 3'-unsubstituted (3'-H) oligomers requiring no further modification, the solution was treated with acid to pH=2.5 to demethoxytritylate the oligomer. The demethoxytritylation mixture was immediately neutralized with concentrated ammonia, and the solution passed through reversed phase resin. The product was recovered by elution with 45% acetonitrile/0.28% aqueous ammonia and isolated as a white powder after lyophilization. Further purification of the product may be performed on cation exchange resins as described in the methods section. Alternatively, it was advantageous to retain the 3'-methoxytrityl/trityl group in order to perform modification of the backbone amine moieties independent of the 3'-terminus of the oligomer, as described below. It this case, the above procedure was followed except that the aqueous acid treatment was omitted.

Amine groups introduced into a morpholino oligomer as part of cationic linkages may be further modified. This concept allows an oligomer to be constructed from a relatively simple modified subunit, but with functionality sufficient to allow the introduction of complex moieties in any location along the backbone of the morpholino oligomers.

Note that, for reasons of synthesis, the 5' terminal linkage of an oligomer does not typically comprise a linkage of type (b1) described herein. As shown, for example, in FIGS. 2P-2Q, the preferred stepwise resin-supported synthesis of the oligomers provides a piperazine ring on the phosphorus atom at the 5'terminus; the presence of a second piperazine ring on the phosphorus would be constrained for steric reasons.

An important modification is the incorporation of guanidinium groups into the oligomer. This may be done in two ways. In the first, the amine moiety on the backbone of the oligomer was directly converted into a guanidinium species by reaction with 1H-pyrazole-1-carboxamidine hydrochloride (M S Bernatowicz, Y Wu, G R Matsueda, *J. Org. Chem.*, 1992, 57(8), 2497-2502) in sodium carbonate buffered aqueous solution, as in FIG. 2L, which also shows the EG3 Tail at the 5'-terminus. In the second, a substance containing both carboxyl and guanidinium groups, e.g., 6-guanidinohexanoic acid was activated with 2-(1-H-benzotriazol-1-yl)-1,1,3,3-tetramethylaminium hexafluorophosphate (HBTU) and reacted with the amine containing oligomer (FIG. 2M). In a similar fashion, 4-guanidinobutanoic acid, 3-guanidinopropanoic acid, and guanidinoacetic acid may be introduced. In a hybrid of these approaches, the amine moiety was reacted with a protected FMOC amino acid, e.g., FMOC 6-aminohexanoic acid to introduce a protected primary amine containing side chain, which after treatment with ammonia to remove the FMOC group was guanylated as above. Fully guanylated species were separated from partially guanylated oligomers by cation chromatography at the appropriate pH.

The termini of the oligomer can also be substituted with guanidinium moieties by these methods, as illustrated in FIG. 2N, which also shows a representative oligomer created from resin 39, without addition of the PEG Tail.

Another modification of note is the incorporation of peptides along the backbone. Small peptides are readily available from commercial sources, for example, Bachem California, Inc. 3132 Kashiwa Street Torrance, Calif. 90505 USA, and AnaSpec, Inc. 2149 O'Toole Ave., San Jose, Calif. 95131. The incorporation of the peptide followed classic 2-(1-H-benzotriazol-1-yl)-1,1,3,3-tetramethylaminium hexafluorophosphate (HBTU) chemistry, as illustrated in FIG. 2O. Guanidinium groups on the oligomer or peptide do not interfere.

Oligomers may also be conjugated at the 3'-terminus to arginine rich peptides, useful to enhance delivery of the products into cells. In this case, protection of primary and secondary amine moieties along the backbone of 3'-methoxtritylated/tritylated oligomers was performed by trifluoroacetylation, as shown in FIG. 2P. The terminal methoxytrityl group was removed and the peptide conjugated using HBTU. The conjugation reaction was worked up by treatment with ammonia to remove the trifluoroacetyl groups. The conjugate was purified by cation exchange chromatography. When the backbone amine functions are fully guanylated, the peptide may be introduced without interference from these side chains, as shown in FIG. 2Q.

D. Antibacterial Antisense Oligonucleotides

In addition to the structural features described above, the antisense compound of the claimed subject matter contains no more than about 30, preferably no more than about 20 nucleotide bases, and has a targeting nucleic acid sequence (the sequence which is complementary to the target sequence) of no fewer than 10 contiguous bases. In one general embodiment, the targeting sequence is complementary to a target sequence containing or within 15 bases, in a downstream direction, of the translational start codon of a bacterial mRNA that encodes a bacterial protein essential for bacterial replication. In another general embodiment, the targeting sequence is a region of the 16S or 23S RNA of the 30S ribosome subunit.

The compound has a $T_m$, when hybridized with the target sequence, of at least about 45° C., typically between about 50° to 60° C., although the Tm may be higher, e.g., 65° C. The selection of bacterial targets, and bacterial mRNA target sequences and complementary targeting sequences are considered in below.

The antisense morpholino oligonucleotide has enhanced antibacterial activity by virtue of its being conjugated to an 8 to 14 residue arginine-rich peptide at either the 5'- or 3'-end of the oligonucleotide and/or by virtue of containing between positively charged groups in at least 10%-80%, preferably 20%-50% of its backbone linkages. As will be seen below, each of these two modifications may enhance antibacterial activity by 10-fold over the unmodified oligonucleotide, and the two modifications together may enhance activity by 100-1,000 fold or more over the unmodified oligonucleotide, allowing a reduction in the amount of compound needed for effective antibacterial activity by 100-1,000 fold or more.

C1. Bacterial Targets

*Escherichia coli* (*E. coli*) is a Gram-negative bacterium that is part of the normal flora of the gastrointestinal tract. There are hundreds of strains of *E. coli*, most of which are harmless and live in the gastrointestinal tract of healthy humans and animals. Currently, there are four recognized classes of enterovirulent *E. coli* (the "EEC group") that cause gastroenteritis in humans. Among these are the enteropathogenic (EPEC) strains and those whose virulence mechanism is related to the excretion of typical *E. coli* enterotoxins. Such strains of *E. coli* can cause various diseases including those associated with infection of the gastrointestinal tract and urinary tract, septicemia, pneumonia, and meningitis. Antibiotics are not effective against some strains and do not necessarily prevent recurrence of infection.

For example, *E. coli* strain 0157:H7 is estimated to cause 10,000 to 20,000 cases of infection in the United States annually (Federal Centers for Disease Control and Prevention). Hemorrhagic colitis is the name of the acute disease caused by *E. coli* O157:H7. Preschool children and the elderly are at the greatest risk of serious complications. *E. coli* strain 0157:H7 was recently reported as the cause the death of four children who ate under cooked hamburgers from a fast-food restaurant in the Pacific Northwest. (See, e.g., Jackson et al., *Epidemiol. Infect.* 120(1):17-20, 1998.)

Exemplary sequences for enterovirulent *E. coli* strains include GenBank Accession Numbers AB011549, X97542, AF074613, Y11275 and AJ007716.

*Salmonella thyphimurium*, are Gram-negative bacteria which cause various conditions that range clinically from localized gastrointestinal infections, gastroenterits (diarrhea, abdominal cramps, and fever) to enteric fevers (including typhoid fever) which are serious systemic illnesses. *Salmonella* infection also causes substantial losses of livestock.

Typical of Gram-negative bacilli, the cell wall of *Salmonella* spp. contains a complex lipopolysaccharide (LPS) structure that is liberated upon lysis of the cell and may function as an endotoxin, which contributes to the virulence of the organism.

Contaminated food is the major mode of transmission for non-typhoidal *salmonella* infection, due to the fact that *Salmonella* survive in meats and animal products that are not thoroughly cooked. The most common animal sources are chickens, turkeys, pigs, and cows; in addition to numerous other domestic and wild animals. The epidemiology of typhoid fever and other enteric fevers caused by *Salmonella* spp. is associated with water contaminated with human feces.

Vaccines are available for typhoid fever and are partially effective; however, no vaccines are available for non-typhoidal *Salmonella* infection. Non-typhoidal salmonellosis is controlled by hygienic slaughtering practices and thorough cooking and refrigeration of food. Antibiotics are indicated for systemic disease, and Ampicillin has been used with some success. However, in patients under treatment with excessive amounts of antibiotics, patients under treatment with immunosuppressive drugs, following gastric surgery, and in patients with hemolytic anemia, leukemia, lymphoma, or AIDS, *Salmonella* infection remains a medical problem.

*Pseudomonas* spp. are motile, Gram-negative rods which are clinically important because they are resistant to most antibiotics, and are a major cause of hospital acquired (nosocomial) infections. Infection is most common in: immunocompromised individuals, burn victims, individuals on respirators, individuals with indwelling catheters, IV narcotic users and individual with chronic pulmonary disease (e.g., cystic fibrosis). Although infection is rare in healthy individuals, it can occur at many sites and lead to urinary tract infections, sepsis, pneumonia, pharyngitis, and numerous other problems, and treatment often fails with greater significant mortality.

*Pseudomonas aeruginosa* is a Gram-negative, aerobic, rod-shaped bacterium with unipolar motility. An opportunistic human pathogen, *P. aeruginosa* is also an opportunistic pathogen of plants. Like other Pseudomonads, *P. aeruginosa* secretes a variety of pigments. Definitive clinical identification of *P. aeruginosa* can include identifying the production of both pyocyanin and fluorescein as well as the organism's ability to grow at 42° C. *P. aeruginosa* is also capable of growth in diesel and jet fuel, for which it is known as a hydrocarbon utilizing microorganism (or "HUM bug"), causing microbial corrosion.

*Vibrio cholera* is a Gram-negative rod which infects humans and causes cholera, a disease spread by poor sanitation, resulting in contaminated water supplies. *Vibrio cholerae* can colonize the human small intestine, where it produces a toxin that disrupts ion transport across the mucosa, causing diarrhea and water loss. Individuals infected with *Vibrio cholerae* require rehydration either intravenously or orally with a solution containing electrolytes. The illness is generally self-limiting; however, death can occur from dehydration and loss of essential electrolytes. Antibiotics such as tetracycline have been demonstrated to shorten the course of the illness, and oral vaccines are currently under development.

*Neisseria gonorrhoea* is a Gram-negative coccus, which is the causative agent of the common sexually transmitted disease, gonorrhea. *Neisseria gonorrhoea* can vary its surface antigens, preventing development of immunity to reinfection. Nearly 750,000 cases of gonorrhea are reported annually in the United States, with an estimated 750,000 additional unreported cases annually, mostly among teenagers and young adults. Ampicillin, amoxicillin, or some type of penicillin used to be recommended for the treatment of gonorrhea. However, the incidence of penicillin-resistant gonorrhea is increasing, and new antibiotics given by injection, e.g., ceftriaxone or spectinomycin, are now used to treat most gonococcal infections.

*Staphylococcus aureus* is a Gram-positive coccus which normally colonizes the human nose and is sometimes found on the skin. *Staphylococcus* can cause bloodstream infections, pneumonia, and surgical-site infections in the hospital setting (i.e., nosocomial infections). *Staph. aureus* can cause severe food poisoning, and many strains grow in food and produce exotoxins. *Staphylococcus* resistance to common antibiotics, e.g., vancomycin, has emerged in the United States and abroad as a major public health challenge both in community and hospital settings. Recently, a vancomycin-resistant *Staph. aureus* isolate has also been identified in Japan.

*Mycobacterium tuberculosis* is a Gram positive bacterium which is the causative agent of tuberculosis, a sometimes crippling and deadly disease. Tuberculosis is on the rise and globally and the leading cause of death from a single infectious disease (with a current death rate of three million people per year). It can affect several organs of the human body, including the brain, the kidneys and the bones, however, tuberculosis most commonly affects the lungs.

In the United States, approximately ten million individuals are infected with *Mycobacterium tuberculosis*, as indicated by positive skin tests, with approximately 26,000 new cases of active disease each year. The increase in tuberculosis (TB) cases has been associated with HIV/AIDS, homelessness, drug abuse and immigration of persons with active infections. Current treatment programs for drug-susceptible TB involve taking two or four drugs (e.g., isoniazid, rifampin, pyrazinamide, ethambutol or streptomycin), for a period of from six to nine months, because all of the TB germs cannot be destroyed by a single drug. In addition, the observation of drug-resistant and multiple drug resistant strains of *Mycobacterium tuberculosis* is on the rise.

*Helicobacter pylori* (*H. pylori*) is a micro-aerophilic, Gram-negative, slow-growing, flagellated organism with a spiral or S-shaped morphology which infects the lining of the stomach. *H. pylori* is a human gastric pathogen associated with chronic superficial gastritis, peptic ulcer disease, and chronic atrophic gastritis leading to gastric adenocarcinoma. *H. pylori* is one of the most common chronic bacterial infections in humans and is found in over 90% of patients with active gastritis. Current treatment includes triple drug therapy with bismuth, metronidazole, and either tetracycline or amoxicillin which eradicates *H. pylori* in most cases. Problems with triple therapy include patient compliance, side effects, and metronidazole resistance. Alternate regimens of dual therapy which show promise are amoxicillin plus metronidazole or omeprazole plus amoxicillin.

*Streptococcus pneumoniae* is a Gram-positive coccus and one of the most common causes of bacterial pneumonia as well as middle ear infections (otitis media) and meningitis. Each year in the United States, pneumococcal diseases account for approximately 50,000 cases of bacteremia; 3,000 cases of meningitis; 100,000-135,000 hospitalizations; and 7 million cases of otitis media. Pneumococcal infections cause an estimated 40,000 deaths annually in the United States. Children less than 2 years of age, adults over 65 years of age and persons of any age with underlying medical conditions, including, e.g., congestive heart disease, diabetes, emphysema, liver disease, sickle cell, HIV, and those living in special environments, e.g., nursing homes and long-term care facilities, at highest risk for infection.

Drug-resistant *S. pneumoniae* strains have become common in the United States, with many penicillin-resistant pneumococci also resistant to other antimicrobial drugs, such as erythromycin or trimethoprim-sulfamethoxazole.

*Treponema pallidum* is a spirochete which causes syphilis. *T. pallidum* is exclusively a pathogen which causes syphilis, yaws and non-venereal endemic syphilis or pinta. *Treponema pallidum* cannot be grown in vitro and does replicate in the absence of mammalian cells. The initial infection causes an ulcer at the site of infection; however, the bacteria move throughout the body, damaging many organs over time. In its late stages, untreated syphilis, although not contagious, can cause serious heart abnormalities, mental disorders, blindness, other neurologic problems, and death.

Syphilis is usually treated with penicillin, administered by injection. Other antibiotics are available for patients allergic to penicillin, or who do not respond to the usual doses of penicillin. In all stages of syphilis, proper treatment will cure the disease, but in late syphilis, damage already done to body organs cannot be reversed.

*Chlamydia trachomatis* is the most common bacterial sexually transmitted disease in the United States and it is estimated that 4 million new cases occur each year. The highest rates of infection are in 15 to 19 year olds. *Chlamydia* is a major cause of non-gonococcal urethritis (NGU), cervicitis, bacterial vaginitis, and pelvic inflammatory disease (PID). *Chlamydia* infections may have very mild symptoms or no symptoms at all; however, if left untreated *Chlamydia* infections can lead to serious damage to the reproductive organs, particularly in women. Antibiotics such as azithromycin, erythromycin, ofloxacin, amoxicillin or doxycycline are typically prescribed to treat *Chlamydia* infection.

*Bartonella henselae* Cat Scratch Fever (CSF) or cat scratch disease (CSD), is a disease of humans acquired through exposure to cats, caused by a Gram-negative rod originally named *Rochalimaea henselae*, and currently known as *Bartonella henselae*. Symptoms include fever and swollen lymph nodes and CSF is generally a relatively benign, self-limiting disease in people, however, infection with *Bartonella henselae* can produce distinct clinical symptoms in immunocompromised people, including, acute febrile illness with bacteremia, bacillary angiomatosis, peliosis hepatis, bacillary splenitis, and other chronic disease manifestations such as AIDS encephalopathy.

The disease is treated with antibiotics, such as doxycycline, erythromycin, rifampin, penicillin, gentamycin, ceftriaxone, ciprofloxacin, and azithromycin.

*Haemophilus influenzae* (*H. influenza*) is a family of Gram-negative bacteria; six types of which are known, with most *H. influenza-related* disease caused by type B, or "HIB". Until a vaccine for HIB was developed, HIB was a common causes of otitis media, sinus infections, bronchitis, the most common cause of meningitis, and a frequent culprit in cases of pneumonia, septic arthritis (joint infections), cellulitis (infections of soft tissues), and pericarditis (infections of the membrane surrounding the heart). The *H. influenza* type B bacterium is widespread in humans and usually lives in the throat and nose without causing illness. Unvaccinated children under age 5 are at risk for HIB disease. Meningitis and other serious infections caused by *H. influenza* infection can lead to brain damage or death.

*Shigella dysenteriae* (*Shigella dys.*) is a Gram-negative rod which causes dysentary. In the colon, the bacteria enter mucosal cells and divide within mucosal cells, resulting in an extensive inflammatory response. *Shigella* infection can cause severe diarrhea which may lead to dehydration and can be dangerous for the very young, very old or chronically ill. *Shigella dys.* forms a potent toxin (shiga toxin), which is cytotoxic, enterotoxic, neurotoxic and acts as a inhibitor of protein synthesis. Resistance to antibiotics such as ampicillin and TMP-SMX has developed, however, treatment with newer, more expensive antibiotics such as ciprofloxacin, norfloxacin and enoxacin, remains effective.

*Listeria* is a genus of Gram-positive, motile bacteria found in human and animal feces. *Listeria monocytogenes* causes such diseases as listeriosis, meningoencephalitis and meningitis. This organism is one of the leading causes of death from food-borne pathogens especially in pregnant women, newborns, the elderly, and immunocompromised individuals. It is found in environments such as decaying vegetable matter, sewage, water, and soil, and it can survive extremes of both temperatures and salt concentration making it an extremely dangerous food-born pathogen, especially on food that is not reheated. The bacterium can spread from the site of infection in the intestines to the central nervous system and the fetal-placental unit. Meningitis, gastroenteritis, and septicemia can result from infection. In cattle and sheep, *listeria* infection causes encephalitis and spontaneous abortion.

*Proteus mirabilis* is an enteric, Gram-negative commensal organism, distantly related to *E. coli*. It normally colonizes the human urethra, but is an opportunistic pathogen that is the leading cause of urinary tract infections in catheterized individuals. *P. mirabilis* has two exceptional characteristics: 1) it has very rapid motility, which manifests itself as a swarming phenomenon on culture plates; and 2) it produce urease, which gives it the ability to degrade urea and survive in the genitourinary tract.

*Yersinia pestis* is the causative agent of plague (bubonic and pulmonary) a devastating disease which has killed millions worldwide. The organism can be transmitted from rats to humans through the bite of an infected flea or from human-to-human through the air during widespread infection. *Yersinia pestis* is an extremely pathogenic organism that requires very few numbers in order to cause disease, and is often lethal if left untreated. The organism is enteroinvasive, and can survive and propagate in macrophages prior to spreading systemically throughout the host.

*Bacillus anthracis* is also known as anthrax. Humans become infected when they come into contact with a contaminated animal. Anthrax is not transmitted due to person-to-person contact. The three forms of the disease reflect the sites of infection which include cutaneous (skin), pulmonary (lung), and intestinal. Pulmonary and intestinal infections are often fatal if left untreated. Spores are taken up by macrophages and become internalized into phagolysozomes (membranous compartment) whereupon germination initiates. Bacteria are released into the bloodstream once the infected macrophage lyses whereupon they rapidly multiply, spreading throughout the circulatory and lymphatic systems, a process that results in septic shock, respiratory distress and organ failure. The spores of this pathogen have been used as a terror weapon.

*Burkholderia mallei* is a Gram-negative aerobic bacterium that causes Glanders, an infectious disease that occurs primarily in horses, mules, and donkeys. It is rarely associated with human infection and is more commonly seen in domesticated animals. This organism is similar to *B. pseudomallei* and is differentiated by being nonmotile. The pathogen is host-adapted and is not found in the environment outside of its host. Glanders is often fatal if not treated with antibiotics, and transmission can occur through the air, or more commonly when in contact with infected animals. Rapid-onset pneumonia, bacteremia (spread of the organism through the blood), pustules, and death are common outcomes during infection. The virulence mechanisms are not well understood, although a type III secretion system similar to the one from *Salmonella typhimurium* is necessary. No vaccine exists for this potentially dangerous organism which is thought to have potential as a biological terror agent. The genome of this organism carries a large number of insertion sequences as compared to the related *Bukholderia pseudomallei* (below), and a large number of simple sequence repeats that may function in antigenic variation of cell surface proteins.

*Burkholderia pseudomallei* is a Gram-negative bacterium that causes meliodosis in humans and animals. Meliodosis is a disease found in certain parts of Asia, Thailand, and Australia. *B. pseudomallei* is typically a soil organism and has been recovered from rice paddies and moist tropical soil, but as an opportunistic pathogen can cause disease in susceptible individuals such as those that suffer from diabetes mellitus. The organism can exist intracellularly, and causes pneumonia and bacteremia (spread of the bacterium through the bloodstream). The latency period can be extremely long, with infection preceding disease by decades, and treatment can take months of antibiotic use, with relapse a commonly observed phenomenon. Intercellular spread can occur via induction of actin polymerization at one pole of the cell, allowing movement through the cytoplasm and from cell-to-cell. This organism carries a number of small sequence repeats which may promoter antigenic variation, similar to what was found with the *B. mallei* genome.

*Burkholderia cepacia* is a Gram-negative bacterium composed of at least seven different sub-species, including *Burkholderia multivorans*, *Burkholderia vietnamiensis*, *Burkholderia stabilis*, *Burkholderia cenocepacia* and *Burkholderia ambifaria*. *B. cepacia* is an important human pathogen which most often causes pneumonia in people with underlying lung disease (such as cystic fibrosis or immune problems (such as (chronic granulomatous disease). *B. cepacia* is typically found in water and soil and can survive for prolonged periods in moist environments. Person-to-person spread has been documented; as a result, many hospitals, clinics, and camps for patients with cystic fibrosis have enacted strict isolation precautions *B. cepacia*. Individuals with the bacteria are often treated in a separate area than those without to limit spread. This is because infection with *B. cepacia* can lead to a rapid decline in lung function resulting in death. Diagnosis of *B. cepacia* involves isolation of the bacteria from sputum cultures. Treatment is difficult because *B. cepacia* is naturally resistant to many common antibiotics including aminoglycosides (such as tobramycin) and polymixin B. Treatment typically includes multiple antibiotics and may include ceftazidime, doxycycline, piperacillin, chloramphenicol, and co-trimoxazole.

*Francisella tularensis* was first noticed as the causative agent of a plague-like illness that affected squirrels in Tulare County in California in the early part of the 20th century by Edward Francis. The organism now bears his namesake. The disease is called tularemia and has been noted throughout recorded history. The organism can be transmitted from infected ticks or deerflies to a human, through infected meat, or via aerosol, and thus is a potential bioterrorism agent. It is an aquatic organism, and can be found living inside protozoans, similar to what is observed with *Legionella*. It has a high infectivity rate, and can invade phagocytic and nonphagocytic cells, multiplying rapidly. Once within a macrophage, the organism can escape the phagosome and live in the cytosol.

Veterinary applications A healthy microflora in the gastrointestinal tract of livestock is of vital importance for health and corresponding production of associated food products. As with humans, the gastrointestinal tract of a healthy animal contains numerous types of bacteria (i.e., *E. coli, Pseudomonas aeruginosa* and *Salmonella* spp.), which live in ecological balance with one another. This balance may be disturbed by a change in diet, stress, or in response to antibiotic or other therapeutic treatment, resulting in bacterial diseases in the animals generally caused by bacteria such as *Salmonella, Campylobacter, Enterococci, Tularemia* and *E. coli*. Bacterial infection in these animals often necessitates therapeutic intervention, which has treatment costs as well being frequently associated with a decrease in productivity.

As a result, livestock are routinely treated with antibiotics to maintain the balance of flora in the gastrointestinal tract. The disadvantages of this approach are the development of antibiotic resistant bacteria and the carry over of such antibiotics and the resistant bacteria into resulting food products for human consumption.

C2. Target Sequences for Cell-Division and Cell-Cycle Target Proteins

The antisense oligomers of the claimed subject matter are designed to hybridize to a region of a bacterial mRNA that encodes an essential bacterial gene. Exemplary genes are those required for cell division, cell cycle proteins, or genes required for lipid biosynthesis or nucleic acid replication. Any essential bacterial gene can be targeted once a gene's essentiality is determined. One approach to determining which genes in an organism are essential is to use genetic footprinting techniques as described (Gerdes, Scholle et al. 2003). In this report, 620 *E. coli* genes were identified as essential and 3,126 genes as dispensable for growth under culture conditions for robust aerobic growth. Evolutionary context analysis demonstrated that a significant number of essential *E. coli* genes are preserved throughout the bacterial kingdom, especially the subset of genes for key cellular processes such as DNA replication, cell division and protein synthesis.

In various aspects, the claimed subject matter provides an antisense oligomer which is a nucleic acid sequence effective to stably and specifically bind to a nucleic acid target sequence which encodes an essential bacterial protein including the following: (1) a sequence specific to a particular strain of a given species of bacteria, such as a strain of *E. coli* associated with food poisoning, e.g., O157:H7 (see Table 1 below); (2) a sequence common to two or more species of bacteria; (3) a sequence common to two related genera of bacteria (i.e., bacterial genera of similar phylogenetic origin); (4) a sequence generally conserved among Gram-negative bacteria; (5) generally conserved among Gram-positive bacteria; or (6) a consensus sequence for essential bacterial protein-encoding nucleic acid sequences in general.

In general, the target for modulation of gene expression using the antisense methods of the claimed subject matter comprises an mRNA expressed during active bacterial growth or replication, such as an mRNA sequence transcribed from a gene of the cell division and cell wall synthesis (dcw) gene cluster, including, but not limited to, zipA, sulA, secA, dicA, dicB, dicC, dicF, ftsA, ftsI, ftsN, ftsK, ftsL, ftsQ, ftsW, ftsZ, murC, murD, murE, murF, murg, minC, minD, minE, mraY, mraW, mraZ, seqA and ddlB. See (Bramhill 1997), and (Donachie 1993), both of which are expressly incorporated by reference herein, for general reviews of bacterial cell division and the cell cycle of *E. coli*, respectively. Additional targets include genes involved in lipid biosynthesis (e.g. acpP) and replication (e.g. gyrA).

Cell division in *E. coli* involves coordinated invagination of all 3 layers of the cell envelope (cytoplasmic membrane, rigid peptidoglycan layer and outer membrane). Constriction of the septum severs the cell into 2 compartments and segregates the replicated DNA. At least 9 essential gene products participate in this process: ftsZ, ftsA, ftsQ, ftsL, ftsI, ftsN, ftsK, ftsW and zipA (Hale and de Boer 1999). Preferred protein targets are the three discussed below, and in particular, the GyrA and AcpP targets described below.

FtsZ, one of the earliest essential cell division genes in *E. coli*, is a soluble, tubulin-like GTPase that forms a membrane-associated ring at the division site of bacterial cells. The ring is thought to drive cell constriction, and appears to affect cell wall invagination. FtsZ binds directly to a novel integral inner membrane protein in *E. coli* called zipA, an essential component of the septal ring structure that mediates cell division in *E. coli* (Lutkenhaus and Addinall 1997).

GyrA refers to subunit A of the bacterial gyrase enzyme, and the gene therefore. Bacterial gyrase is one of the bacterial DNA topoisomerases that control the level of supercoiling of DNA in cells and is required for DNA replication.

AcpP encodes acyl carrier protein, an essential cofactor in lipid biosynthesis. The fatty acid biosynthetic pathway requires that the heat stable cofactor acyl carrier protein binds intermediates in the pathway.

For each of these three proteins, Table 1 below provides exemplary bacterial sequences which contain a target sequence for each of a number of important pathogenic bacteria. The gene sequences are derived from the GenBank Reference full genome sequence for each bacterial strain (http://www.ncbi.nlm.nih.gov/genomes/lproks.cgi). The gene location on either the positive (+) or negative (−) strand of the genome is listed under "Strand", it being recognized that the strand indicated is the coding sequence for the protein, that is, the sequence corresponding to the mRNA target sequence for that gene. For example, the two *E. coli* genes (ftsZ and acpP) in which the coding sequence is on the positive strand, the sequence is read 5' to 3' in the left-to-right direction. Similarly for the *E. coli* gyrA gene having the coding region on the minus genomic strand, the coding sequence is read as the reverse complement in the right to left direction (5' to 3').

Based on these considerations, exemplary targeting sequences for use in practicing the claimed invention are those having between 10-25, preferably 10-20 bases, preferably complete but at least 10-base complementarity with the mRNA target sequence, and complementary to a region of the mRNA that includes the AUG start site or a region up to 20 bases downstream of the start site. Where the compound is used in inhibiting infection by one of the bacteria identified in the table below, by inhibiting one of the three identified bacterial proteins, the antisense oligomer compound has a sequence that is complementary to at least 10 contiguous bases of the corresponding target sequence indicated in the table, where these target sequences are identified in the sequence listing below by SEQ ID NOS:1-61.

TABLE 1

Exemplary bacterial target regions

| Organism (GenBank Ref.) | Target Gene | Nucleotide Region | SEQ ID NO. |
|---|---|---|---|
| *Escherichia coli* (NC 000913) | ftsZ | 105295-105325 | 1 |
| | acpP | 1150828-1150858 | 2 |
| | gyrA | 2337422-2337452 | 3 |
| *Escherichia coli* O157:H7 (NC 002655) | ftsZ | 109901-109931 | 4 |
| | acpP | 1595786-1595816 | 5 |
| | gyrA | 3136439-3136469 | 6 |
| *Salmonella thyphimurium* (NC 003197) | ftsZ | 155673-155703 | 7 |
| | acpP | 1280103-1280133 | 8 |
| | gyrA | 2376327-2376357 | 9 |
| *Pseudomonas aeruginosa* (NC 002516) | ftsZ | 4940463-4940493 | 10 |
| | acpP | 3325162-3325192 | 11 |
| | gyrA | 3559177-3559207 | 12 |
| *Vibrio cholera* (NC 002505) | ftsZ | 2566223-2566253 | 13 |
| | acpP | 254495-254525 | 14 |
| | gyrA | 1330197-1330227 | 15 |
| *Neisseria gonorrhoea* (NC 002946) | ftsZ | 1500031-1500060 | 16 |
| | acpP | 1724391-1724420 | 17 |
| | gyrA | 621170-621199 | 18 |
| *Staphylococcus aureus* (NC 002745) | ftsZ | 1165772-1165802 | 19 |
| | gyrA | 6995-7025 | 20 |
| | fmhB | 2322402-2322431 | 21 |
| *Mycobacterium tuberculosis* (NC 002755) | ftsZ | 2408265-2408295 | 22 |
| | acpP | 1510172-1510202 | 23 |
| | gyrA | 7292-7322 | 24 |
| | pimA | 2935126-2935126 | 25 |
| | cysS2 | 4015924-4015953 | 26 |
| *Helicobacter pylori* (NC 000915) | ftsZ | 1042227-1042257 | 27 |
| | acpP | 594253-594283 | 28 |
| | gyrA | 752502-752532 | 29 |
| *Streptococcus pneumoniae* (NC 003028) | ftsZ | 1566686-1566716 | 30 |
| | acpP | 396681-396711 | 31 |
| | gyrA | 1149835-1149865 | 32 |
| *Treponema palladium* (NC 000919) | ftsZ | 414741-414771 | 33 |
| | acpP | 877626-877656 | 34 |
| | gyrA | 4381-4411 | 35 |
| *Chlamydia trachomatis* (NC 000117) | acpP | 263915-263945 | 36 |
| | gyrA | 756474-756504 | 37 |
| *Bartonella henselae* (NC 005956) | ftsZ | 1232075-1232104 | 38 |
| | acpP | 623133-623162 | 39 |
| | gyrA | 1123338-1123367 | 40 |
| *Hemophilis influenza* | ftsZ | 1212011-1212041 | 41 |

TABLE 1-continued

Exemplary bacterial target regions

| Organism (GenBank Ref.) | Target Gene | Nucleotide Region | SEQ ID NO. |
|---|---|---|---|
| (NC 000907) | acpP | 171140-171170 | 42 |
|  | gyrA | 1344341-1344371 | 43 |
| Listeria monocytogenes | ftsZ | 2102288-2102307 | 44 |
| (NC 002973) | acpP | 1860519-1860548 | 45 |
|  | gyrA | 8055-8084 | 46 |
| Yersinia pestis | ftsZ | 605864-605893 | 47 |
| (NC 003143) | acpP | 1824110-1824139 | 48 |
|  | gyrA | 1370719-1370748 | 49 |
| Bacillus anthracis | ftsZ | 3725338-3725367 | 50 |
| (NC 005945) | acpP | 3666877-3666906 | 51 |
|  | gyrA | 6586-6615 | 52 |
| Burkholderia mallei | ftsZ | 2650793-2650822 | 53 |
| (NC 006348) | acpP | 559420-559449 | 54 |
|  | gyrA | 461883-461912 | 55 |
| Burkholderia pseudomallei | ftsZ | 3600339-3600368 | 56 |
| (NC 006350) | acpP | 2945187-2945216 | 57 |
|  | gyrA | 3039114-3039143 | 58 |
| Francisella tularensis | ftsZ | 203738-203767 | 59 |
| (NC 006570) | acpP | 1421890-1421919 | 60 |
|  | gyrA | 1639887-1639916 | 61 |

Any essential bacterial gene can be targeted using the methods of the claimed subject matter. As described above, an essential bacterial gene for any bacterial species can be determined using a variety of methods including those described by Gerdes for E. coli (Gerdes, Scholle et al. 2003). Many essential genes are conserved across the bacterial kingdom thereby providing additional guidance in target selection. Target regions can be obtained using readily available bioinformatics resources such as those maintained by the National Center for Biotechnology Information (NCBI). Complete reference genomic sequences for a large number of microbial species can be obtained (e.g., see http://www.ncbi.nlm.nih.gov/genomes/lproks.cgi) and sequences for essential bacterial genes identified. Bacterial strains can be obtained from the American Type Culture Collection (ATCC). Simple cell culture methods, such as those described in the Examples, using the appropriate culture medium and conditions for any given species, can be established to determine the antibacterial activity of antisense compounds. Once a suitable targeting antisense oligomer has been identified, the peptide moieties of the compounds can be altered to obtain optimal antibacterial activity. An optimal peptide moiety can then be fixed and alternative antisense moieties tested for improved antibacterial activity. One or more iterations of this process can lead to compounds with improved activity but, in general, no more than two iterations are needed to identify highly active antibacterial agents.

Thus, the first step in selecting a suitable antisense compound is to identify, by the methods above, a targeting sequence that includes the AUG start site and/or contains at least about 10-20 bases downstream of the start site. For purposes of illustration, assume that the antisense compound to be prepared is for use in inhibiting an E. coli bacterial infection in an individual infected with E. coli strain 0157:H7, and that the essential gene being targeted is the E. coli acpP gene. One suitable target sequence for this gene identified by the methods above is SEQ ID NO:2 having the sequence 5'-ATTTAAGAGTATGAGCACTATCGAAGMCGC-3' where the sequence gives the DNA thymine (T) bases rather than the RNA uracil (U) bases, and where the AUG start site (ATG) is shown in bold.

Again, for purposes of illustration, four model antisense targeting sequences, each of them 11 bases in length, are selected: (i) an antisense sequence that spans the AUG start site with four bases of each side and has the sequence identified by SEQ ID NO:94; (ii) an antisense sequence that overlaps the AUG starts at its 5' end and extends in a 3' direction an additional 8 bases into the coding region of the gene, identified as SEQ ID NO:95; (iii) an antisense sequence complementary to bases 5-15 of the gene's coding region, identified as SEQ ID NO:66, and (iv) an antisense sequence complementary to bases 11-21 of the gene's coding region, identified as SEQ ID NO:96.

Once antisense sequences have been selected and the antisense compound synthesized and conjugated to arginine and/or lysine-containing peptides, the compounds may be tested for the ability to inhibit bacterial growth, in this case growth of an E. coli strain in culture. Following the protocol in Example 1, for example, the four 11mer sequences described above are individually tested for optimal activity, e.g., maximum drop in CFU/ml at a given dose, e.g., 5-200M, against an E. coli culture. Compound(s) showing optimal activity are then tested in animal models, as described in Example 2, or veterinary animals, prior to use for treating human infection.

C2. Target Sequences for Bacterial 16S Ribosomal RNA

In one embodiment, the antisense oligomers of the invention are designed to hybridize to a region of a bacterial 16S rRNA nucleic acid sequence under physiological conditions, with a $T_m$ substantially greater than 37° C., e.g., at least 45° C. and preferably 60° C.-80° C. The oligomer is designed to have high binding affinity to the nucleic acid and may be 100% complementary to the 16S rRNA nucleic acid target sequence, or it may include mismatches, as further described above.

More particularly, the antisense oligonucleotide that is enhanced in activity, in accordance with the invention, has a targeting sequence that is effective to stably and specifically bind to a target 16S rRNA sequences which has one or more of the following characteristics: (1) a sequence found in a double stranded region of a 16s rRNA, e.g., the peptidyl transferase center, the alpha-sarcin loop and the mRNA binding region of the 16S rRNA sequence; (2) a sequence found in a single stranded region of a bacterial 16s rRNA; (3) a sequence specific to a particular strain of a given species of bacteria, i.e., a strain of E. coli associated with food poisoning; (4) a sequence specific to a particular species of bacteria; (5) a sequence common to two or more species of bacteria; (6) a sequence common to two related genera of bacteria (i.e., bacterial genera of similar phylogenetic origin); (7) a sequence generally conserved among Gram-negative bacterial 16S rRNA sequences; (6) a sequence generally conserved among Gram-positive bacterial 16S rRNA sequences; or (7) a consensus sequence for bacterial 16S rRNA sequences in general.

Exemplary bacteria and associated GenBank Accession Nos. for 16S rRNA sequences are provided in Table 1 of above-referenced U.S. Pat. No. 6,677,153.

It will be understood that one of skill in the art may readily determine appropriate targets for antisense oligomers, and design and synthesize antisense oligomers using techniques known in the art. Targets can be identified by obtaining the sequence of a target 16S or 23S nucleic acid of interest (e.g. from GenBank) and aligning it with other 16S or 23S nucleic acid sequences using, for example, the MacVector 6.0 program, a ClustalW algorithm, the BLOSUM 30 matrix, and default parameters, which include an open gap penalty of 10 and an extended gap penalty of 5.0 for nucleic acid alignments. An alignment may also be carried out using the Lasergene99 MegAlign Multiple Alignment program with a ClustalW algorithm run under default parameters.

For example, given the 16s rRNA sequences provided in Table 1 and other 16s rRNA sequences available in GenBank, one of skill in the art can readily align the 16s rRNA sequences of interest and determine which sequences are conserved among one or more different bacteria, and those which are specific to one or more particular bacteria. A similar alignment can be performed on 23S rRNA sequences.

As an illustration, the 16S rRNA sequences from the organisms shown in Table 1 were aligned using the Lasergene 99 MegAlign Multiple Alignment program, with a ClustalW algorithm and default parameters. Tables 2-5 of the above-referenced U.S. Pat. No. 6,677,153 show exemplary oligomers antisense to 16S rRNA of these bacterial species, including sequences targeting individual bacteria, multiple bacteria, and broad spectrum sequences. These oligomers were derived from the sequences in Table 1 and from the alignment performed as described above. As the Tables show, a number of sequences were conserved among different organisms.

III. Antibacterial Activity in Cell Culture

Figure 3A:
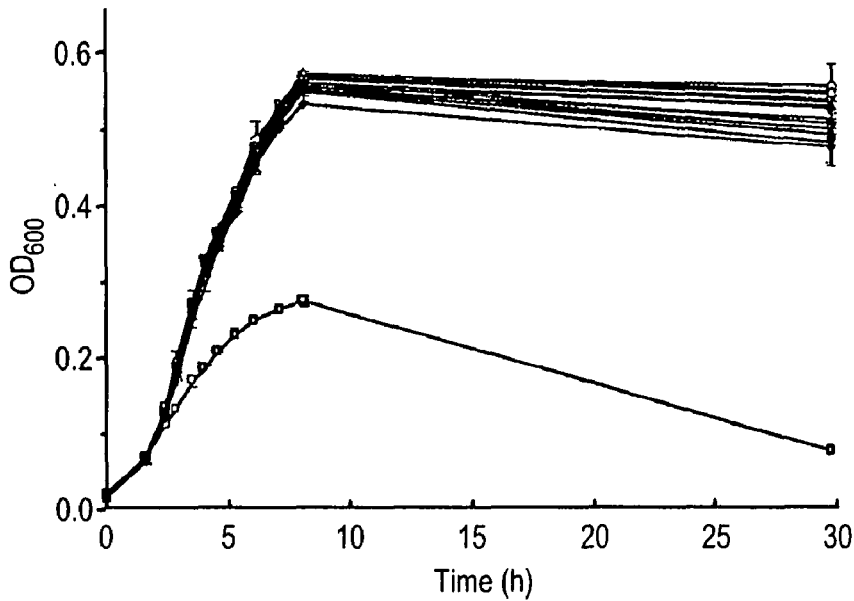
FIGS. 3A and 3B show the effect of AcpP antisense length on growth of *E. coli* AS19. Cultures of *E. coli* AS19 were grown (37° C.) with various lengths (6 to 20 bases) of overlapping PMO (20 μM) targeted to the region around the start codon of the *E. coli* acpP (Table 2, SEQ ID NO:2). Optical density (OD) was monitored over time (FIG. 3A) and open squares indicate culture with 11-base PMO 169 (SEQ ID NO:66) and viable cells (CFU/ml) measured after 8 hours (FIG. 3B).
Figure 3B:
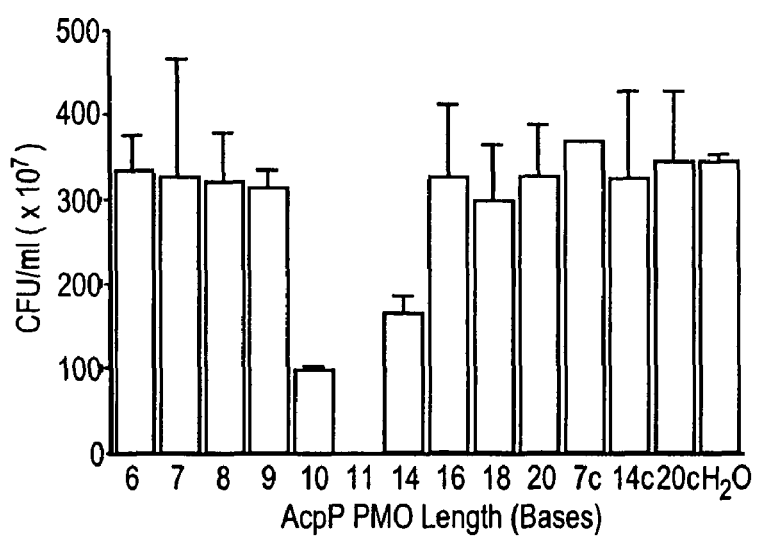
Figure 4:
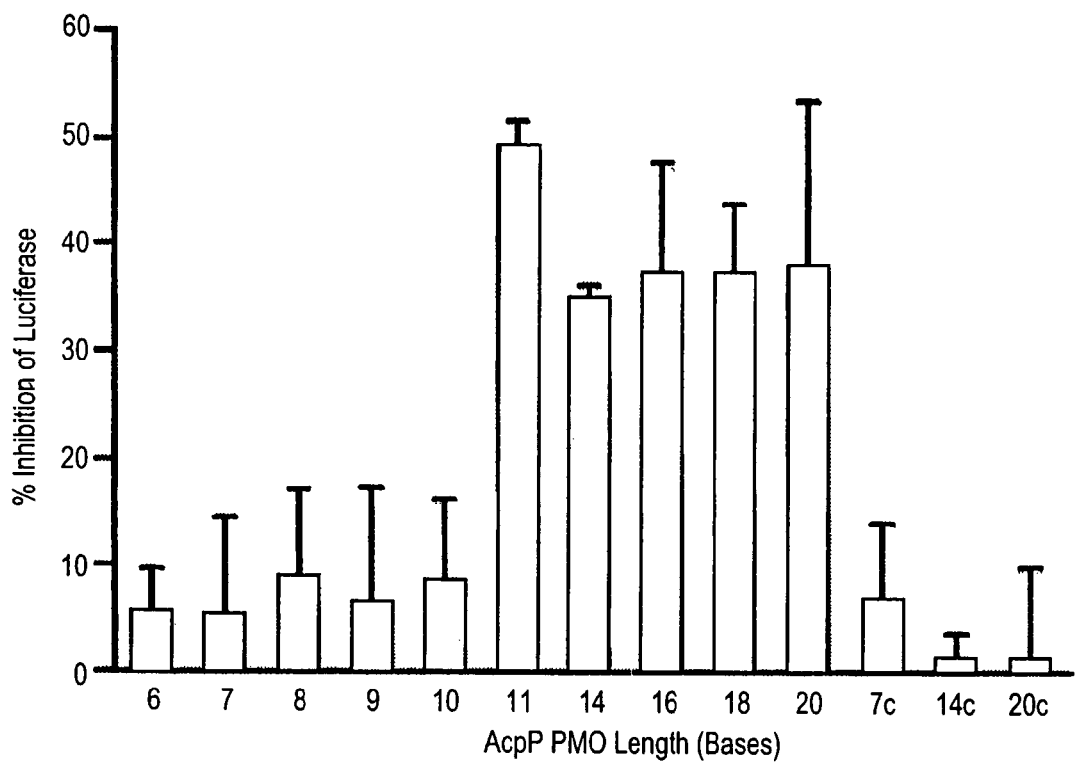
FIG. 4 shows the effect of antisense length on AcpP-luciferase expression in cell-free translation reactions. PMOs of various lengths and targeted around the start codon of acpP (Table 2) were added individually (100 nM) to bacterial cell-free translation reactions programmed to make AcpP-luc.

Antisense oligonucleotide compounds having enhanced activity by virtue of having an arginine-rich carrier peptide and/or a positively charged backbone, and directed against the AUG start site region of the bacterial AcpP gene were tested for their ability to inhibit bacterial growth in culture. These studies are reported in Example 21, with reference to FIGS. 3A and 3B. As seen in the latter figure, a striking inhibition was observed for antisense compounds having between 10 and 14 bases, with nearly complete inhibition being observed for the compound with an 11-base length. As with the expression studies involving marker genes described above, the results for inhibition of a bacterial gene in bacteria are unpredictable from the behavior of the same antisense compounds in a cell-free bacterial system. As seen in FIG. 4, strongest inhibition was observed for antisense compounds between 11 and 20 bases.

Figure 12:
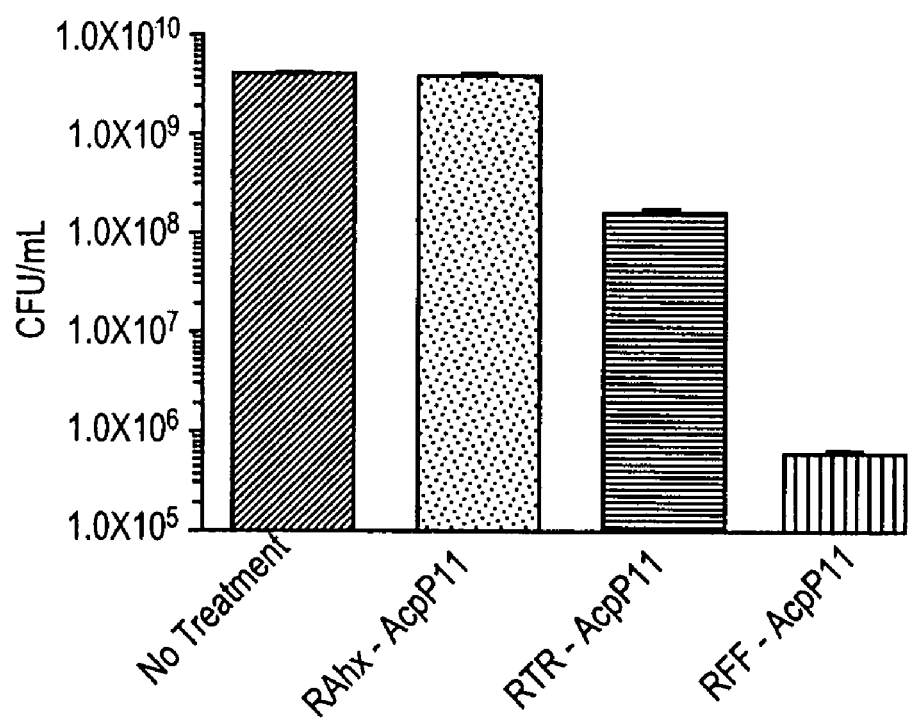
FIG. 12 shows the antibacterial activity of three P-PMOs as measured by CFU/ml after 8 hours of treatment.
Figure 13:
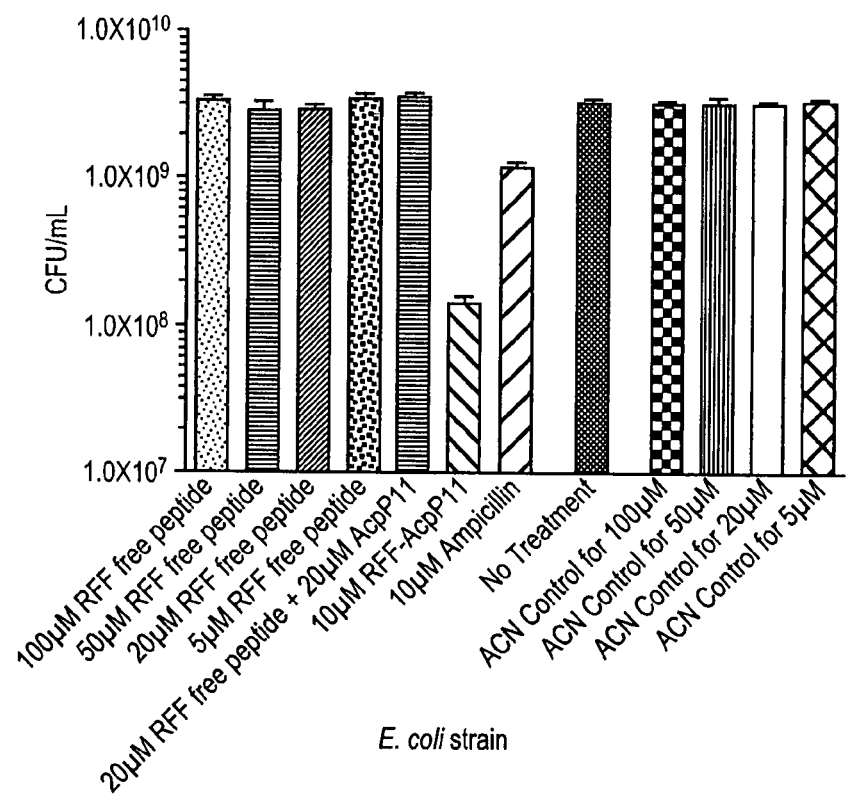
FIG. 13 shows the effect of treatment with a dilution series of RFF peptide, free RFF peptide mixed with AcpP11 PMO, RFF-AcpP11 P-PMO, ampicillin or no treatment.
Figure 14:
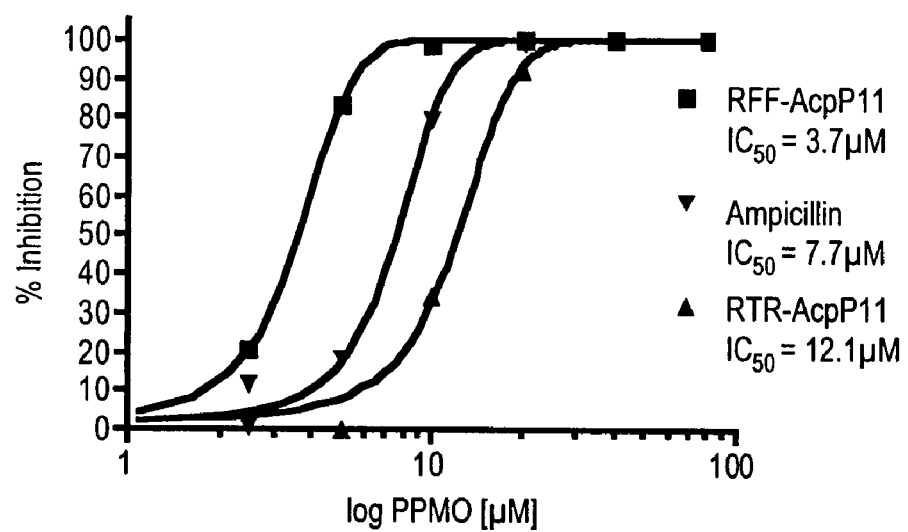
FIG. 14 shows the dose response curves for each of two P-PMOs compared to ampicillin and the associated $IC_{50}$ values for RFF-AcpP11, RTR-AcpP11 (SEQ ID NOS:88 and 89) and ampicillin.

As described in Example 23 and shown in FIGS. 7 to 16, conjugation of an arginine-rich peptide to the antisense oligonucleotides described above greatly enhance their antibacterial properties. Exemplary amino acid sequences and the peptides used in experiments in support of the claimed subject matter are listed in Table 4 below as SEQ ID NOS: 79-93. One exemplary peptide is named RFF (SEQ ID NO: 79) and consists of the sequence N-RFFRFFRFFAhxβAla-COON (using the standard one letter amino acid code and Ahx for 6-aminohexanoic acid and Ala for beta-alanine), and has three repeating Arg-Phe-Phe residues. This peptide is representative of one model peptide having at least two, preferably three repeating Arg-Phe-Phe units. One exemplary peptide-conjugated PMO (P-PMO) derived from the RFF peptide (RFF-AcpP11, SEQ ID NO:88) demonstrated the ability to reduce the CFU/ml of E. coli strains by as much as five orders of magnitude (FIG. 11) and an $IC_{50}$ of 3.7 µM that is lower than the 50% inhibitory concentration ($IC_{50}$) observed for ampicillin (7.7 µM) under the same culture conditions (FIG. 14).

Figure 20:
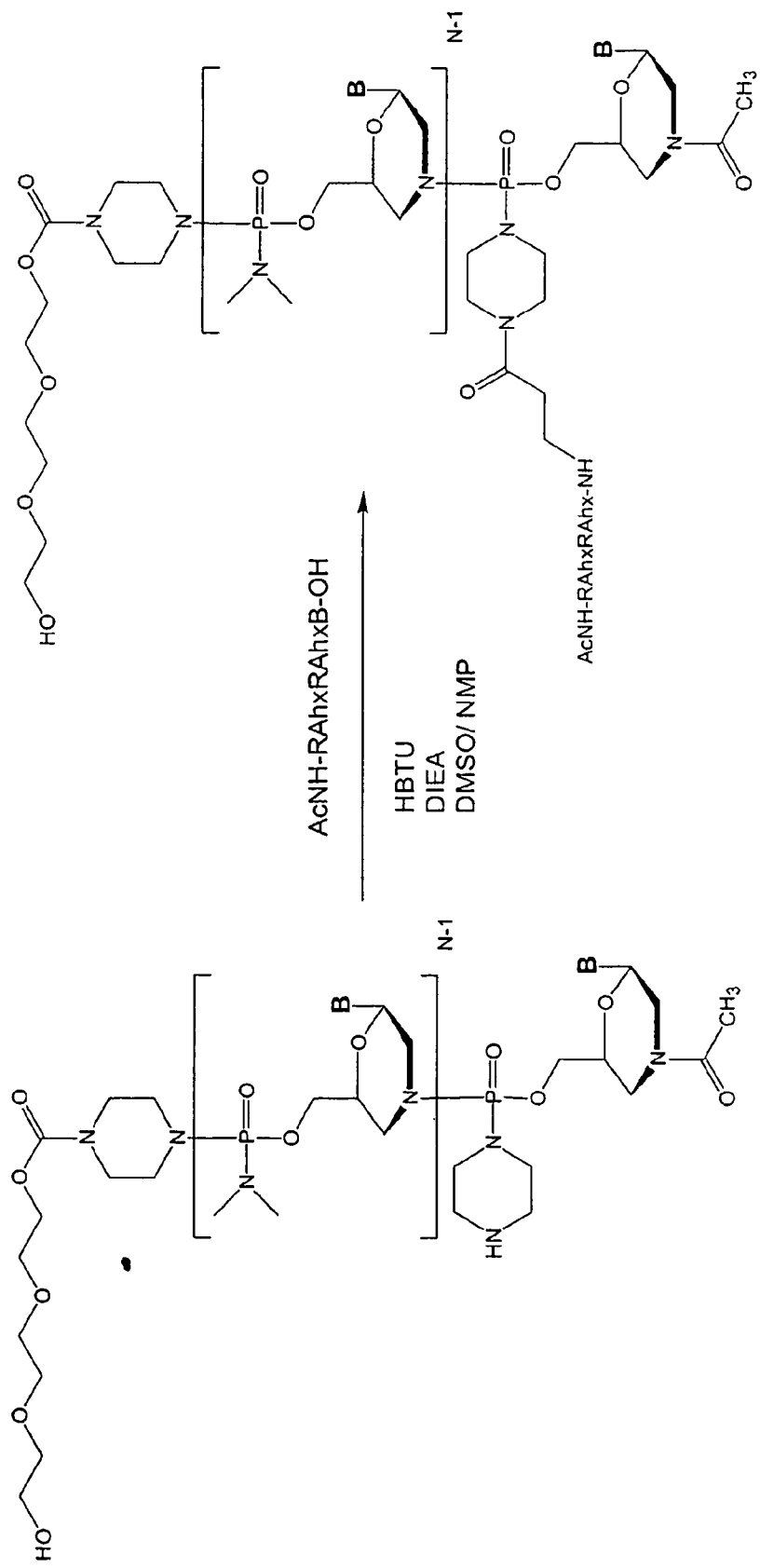
FIG. 20 shows the effect of $(RAhxR)_4$-AcpP11+P-PMO+ compared to ampicillin on wild type *E. coli* as measured by minimum inhibitory concentration (MIC).

Another exemplary peptide named $(RAhxR)_4$ consisting of the sequence RAhxRRAhxRRAhxRRAhxRAhxβAla-COOH (SEQ ID NO:97) contains 4 repeating Arg-Ahx-Arg sequences. An exemplary conjugate derived from the $(RAhxR)_4$ peptide ($[RAhR]_4$-AcpP+, SEQ ID NO: 98) demonstrated a minimum inhibitory concentration (MIC) of 0.313 µM, a 32-fold reduction in the MIC versus ampicillin (10.0 µM), as measured against E. coli W3110 in the broth microdilution method of the Clinical and Laboratory Standards Institute (FIG. 20).

The carrier peptides have the ability, when conjugated to the 5'- or 3'-end of the anti-bacterial antisense PMO compound having SEQ ID NO:66, to enhance the anti-bacterial activity of the PMO compound by a factor of at least 10 and typically at least $10^2$, as measured by the reduction in bacterial colony-forming units/ml (CFU/ml) when the peptide-conjugated PMO (P-PMO) compound is added at a concentration of 20 µM in a culture to E. coli, strain W3110 at $5\times10^7$ CFU/ml for a period of 8 hours at 37° C. with aeration, relative to the activity of the PMO compound alone. The insertion of cationic linkages, as shown in FIG. 2H, into the P-PMO backbone to form a P-PMO+ enhances the antibacterial activity of the conjugate by a factor of 3-fold, as measured in vivo by the increase in survival and the reduction in bacterial CFU/mL, relative to the activity of the uncharged P-PMO compound alone.

Thus, the carrier peptides and/or charged backbone linkages described above are capable of enhancing the activity of a morpholino antisense oligonucleotide up to 100-1,000 times or more. It will be appreciated that selection of additional carrier peptide sequences within the general description of the carrier peptide above, and for optimizing the number and distribution of charged groups along the oligonucleotide backbone can be carried out with the above cell-culture test methods. For example, the oligonucleotide conjugate with charged backbone groups is added, at a concentration of 20 µM in a culture to E. coli, strain W3110 for a period of 8 hours, with the oligonucleotide alone (control) being added at a similar concentration to a culture of the same bacteria. After an eight-hour incubation time, the number of colony forming units per ml (CFU/ml) are measured in both the "conjugate" or "conjugate-charged-backbone" or "charged-backbone" and control cultures. If the CFU/ml count for the enhanced oligonucleotide culture is more than 100-fold less, and preferably a 1000-fold less than that of the control culture, the peptide can be identified as one suitable for use as a high-activity antibacterial agent.

IV. Method for Inhibiting Bacteria

The enhanced-activity oligonucleotide of the invention is useful in a method of inhibiting bacterial infection, by exposing the infecting bacteria to the enhanced-activity compound, as illustrated by the study reported in Example 21 and described above with respect to FIGS. 3A and 3B. The activities reporter here were determined with a representative "PMO," "P-PMO," or "P-PMO+" oligonucleotide as representative of an oligonucleotide with phosphorus-containing backbone linkages.

Figure 5:
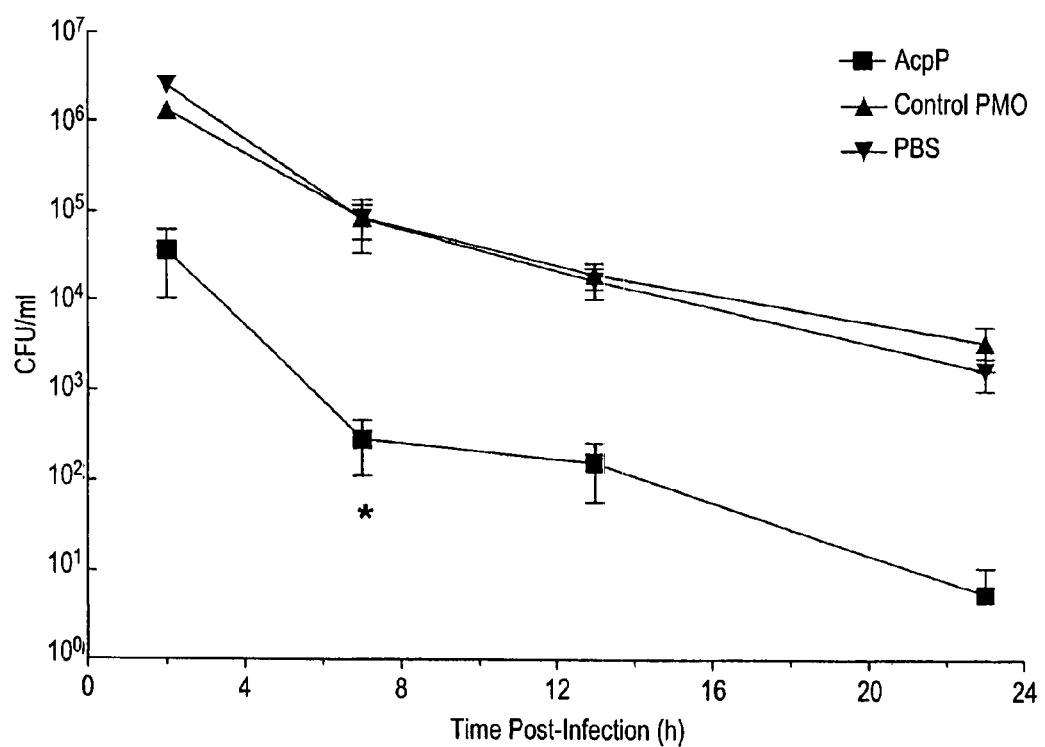
FIG. 5 shows CFU/ml in peritoneal lavages from mice infected with permeable *E. coli* strain AS19 and treated with acpP PMO (■; SEQ ID NO:66), nonsense PMO (▲), or PBS (▼) at 0 hours. At each time indicated, peritoneal lavage was collected and analyzed for bacteria (CFU/ml) from 3 mice in each treatment group.

In one aspect, the method is applied to inhibiting a bacterial infection in a mammalian subject, including a human subject, by administering the antisense compound to the subject in a therapeutic amount. To demonstrate the method, groups of 12 mice were injected IP with E. coli AS19, which has a genetic defect that makes it abnormally permeable to high MW solutes. Immediately following infection, each mouse was injected IP with 300 µg of an 11-base PMO complementary to acpP (SEQ ID NO:66), an 11-base nonsense sequence PMO, or PBS, as detailed in Example 22. As seen in FIG. 5, mice treated with the target antisense showed a reduction in bacterial CFUs of about 600 at 23 hours, compared with control treatment.

Figure 6:
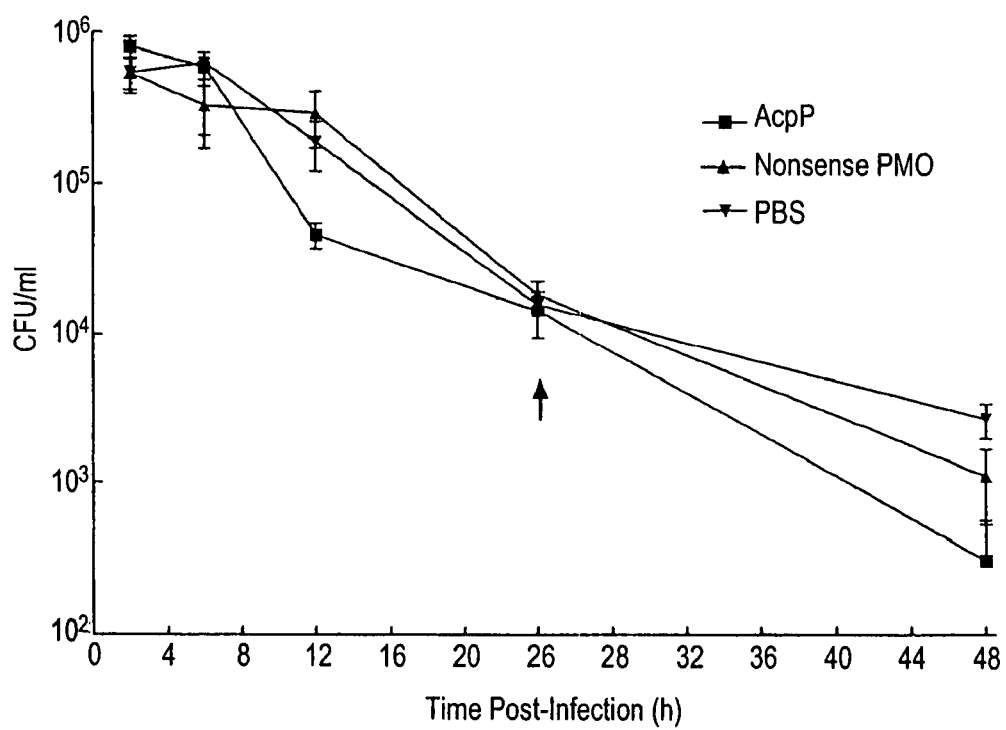
FIG. 6 shows CFU/ml in peritoneal lavages from mice infected *E. coli* strain SM105 and treated with PMO as described in FIG. 13.
Figure 7:
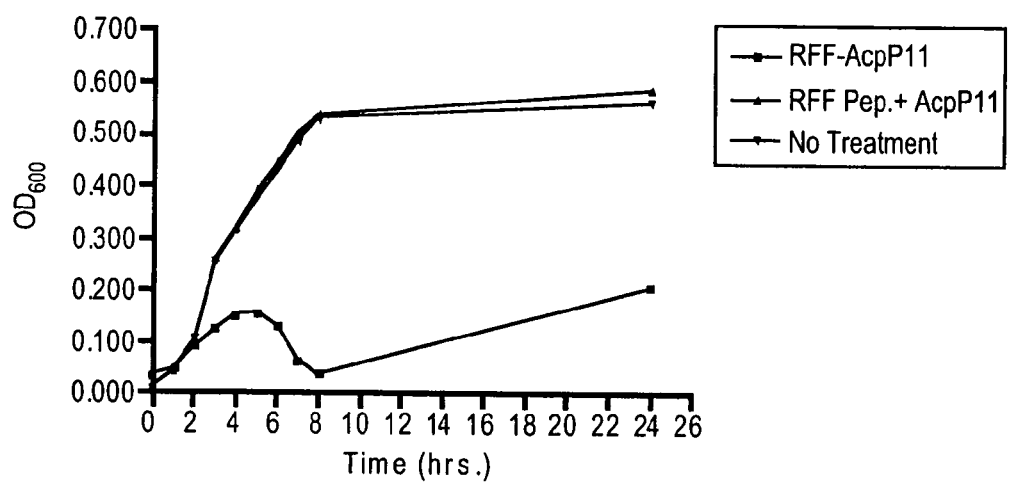
FIGS. 7 to 10 show the growth as measured by optical density ($OD_{600}$) of four strains of *E. coli* grown for 24 hours in the presence of the peptide-conjugated PMO (P-PMO) RFF-AcpP11 (SEQ ID NO:79) compared to no treatment and treatment with a mixture of the AcpP11 PMO and the RFF peptide (SEQ ID NOS:66 and 79, respectively).
Figure 8:
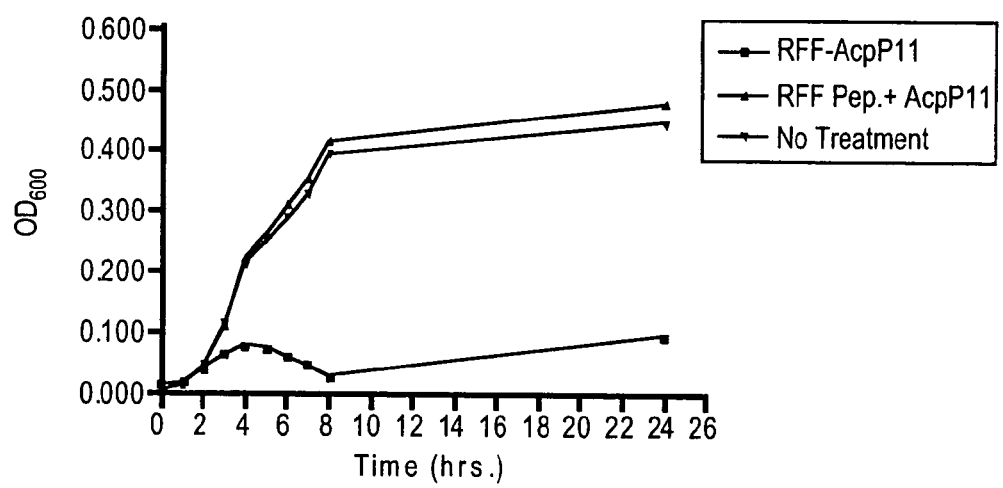
Figure 9:
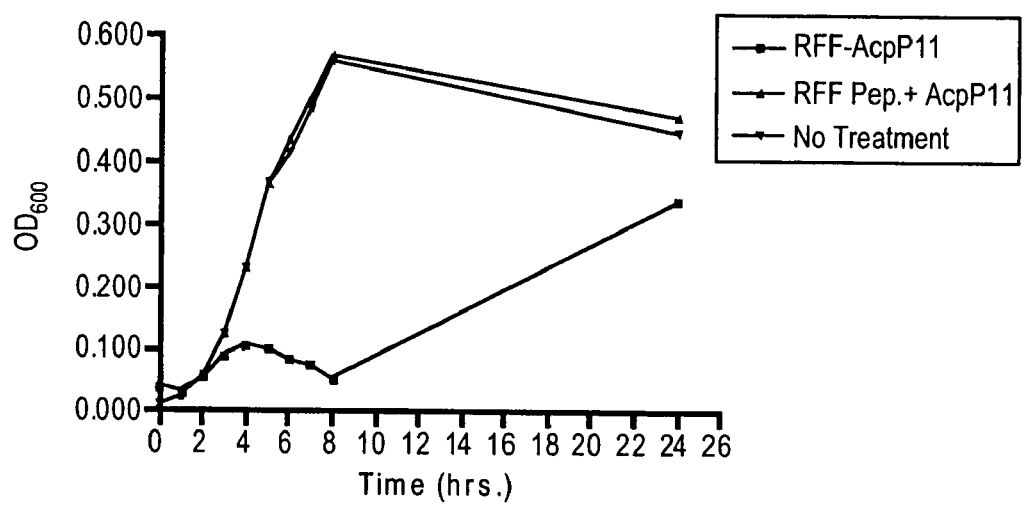
Figure 10:
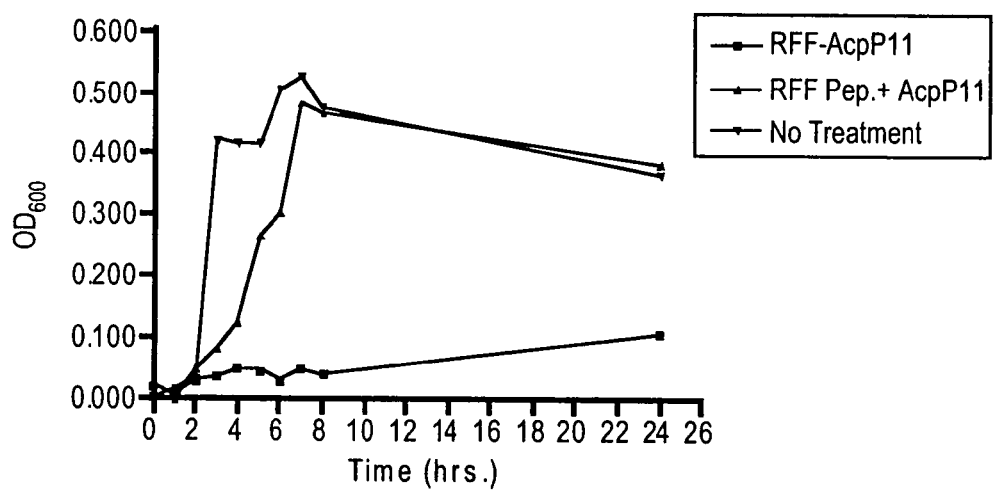

The same PMOs were again tested, except with E. coli SM105, which has a normal outer membrane. In this method, acpP PMO reduced CFU by 84% compared to nonsense PMO at 12 hours post-infection. There was no reduction of CFU at 2, 6, or 24 hours (FIG. 6). Mice were injected with a second dose at 24 hours post-infection. By 48 hours post-infection the CFU of acpP PMO-treated mice were 70% lower than the CFU of nonsense PMO-treated mice (FIG. 6).

To demonstrate that the effect on bacterial infection was sequence specific, a luciferase reporter gene whose expression would not affect growth was used, and luciferase expression was measured directly by two independent criteria, luciferase activity and luciferase protein abundance. As detailed in Example 2, the study demonstrated that an antisense compound complementary to the luciferase mRNA inhibited luciferase expression at two different times after administration of the PMO. Moreover, inhibition was quantitatively similar with both methods of measurement. These results show directly that PMO inhibit bacterial target gene expression in vivo in a sequence-specific manner.

An improved antibacterial PMO can be obtained by conjugating a short 6-14 amino acid peptide that enhances either intracellular delivery or antisense activity or both. Exemplary peptides and peptide-conjugated PMO (P-PMO) are listed in Table 4 as SEQ ID NOS:88-93. As described in Example 23, enhanced antibacterial activity was observed in pure culture experiments using a variety of *E. coli* and *S. typhimurium* strains including the clinically isolated enterpathogenic *E. coli* (EPEC) strain O127:H6. Example 24 describes the antibacterial activity of peptide-conjugated PMO targeted to *B. cenocepacia* and *P. aeruginosa*.

Figure 19A:
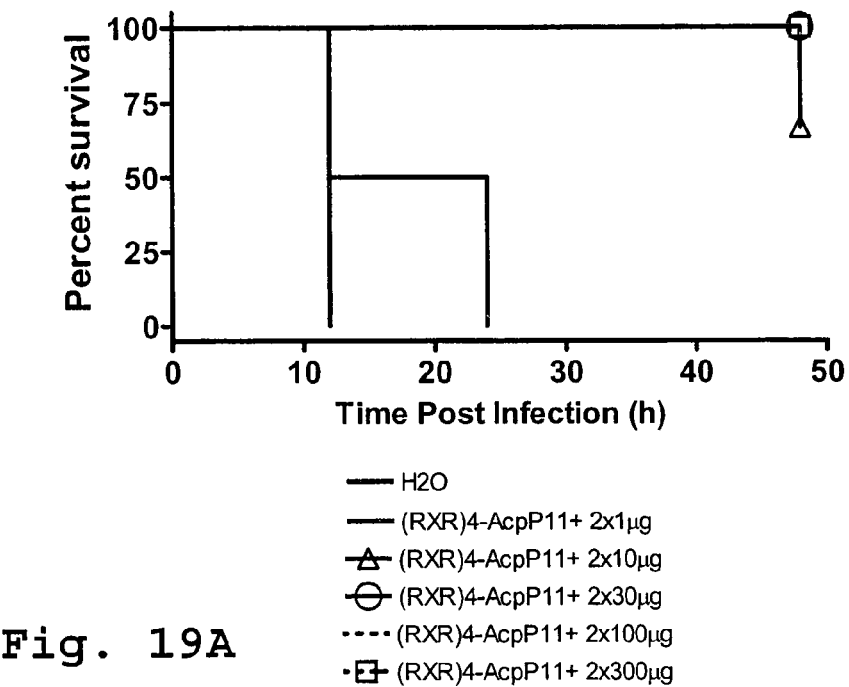
FIGS. 19 A-C show the dose response antibacterial effect of the $(RAhxR)_4$-AcpP11+P-PMO+ on *E. coli* infected mice up to 48 hours post infection as measured by percent survival of mice (FIG. 19A), CFU/mL in mouse blood samples (19B), and change in body temperature (FIG. 19C)
Figure 19B:
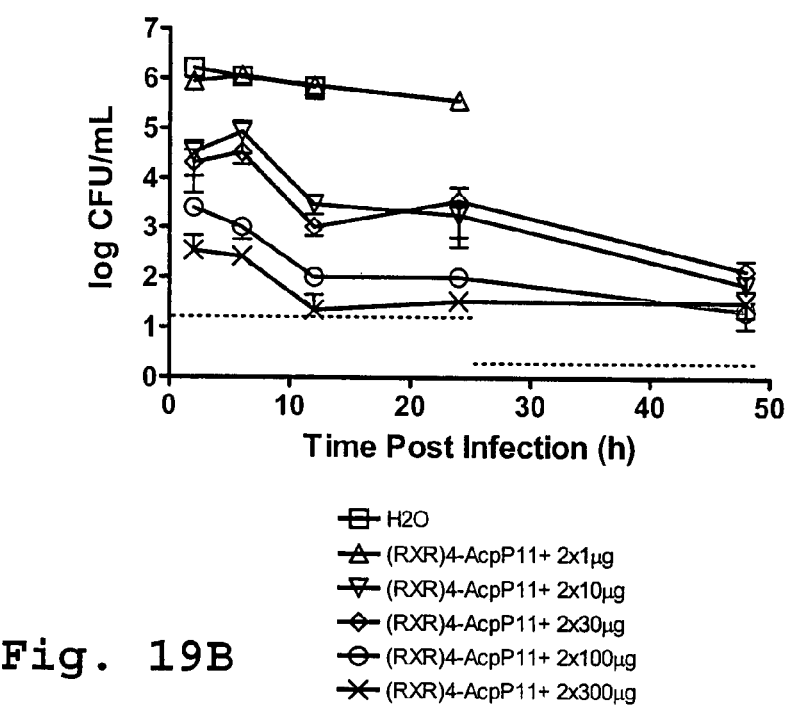
Figure 19C:
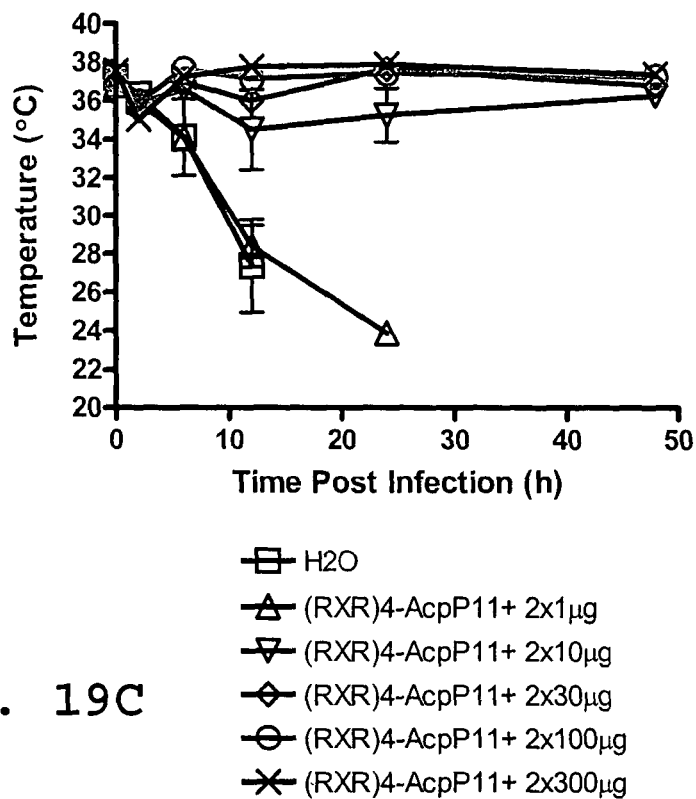
Figure 20:
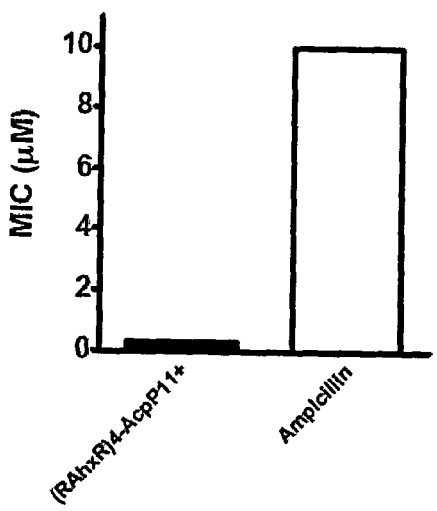

In one application of the enhanced-activity compounds, the method is applied to inhibiting a bacterial infection in a mammalian subject, including a human subject, by administering the antisense compound to the subject in a therapeutic amount. To demonstrate the method, groups of 2 to 4 mice were injected IP with *E. coli W*3110. Immediately following infection and again 12 hours later, each mouse was injected IP with water control or 1, 10, 30, 100, or 300 µg of an 11-base P-PMO+ complementary to acpP (SEQ ID NO:98), as detailed in Example 5. As seen in FIGS. 19A-C, mice treated with 10 µg and above of the P-PMO+ (oligonucleotide with conjugate carrier peptide and charged backbone linkages) showed full protection up to termination of the study at 48 hours after infection, and a dose-dependent reduction in bacterial CFUs ranging from 0.5 to 4 magnitudes, compared with control treatment.

It will be understood that the in vivo efficacy of such a P-PMO+ in a subject using the methods of the claimed invention is dependent upon numerous factors including, but not limited to, (1) the target sequence; (2) the duration, dose and frequency of antisense administration; and (3) the general condition of the subject.

In other cases, the antisense oligonucleotides of the claimed subject matter find utility in the preparation of antibacterial vaccines. In this aspect of the claimed subject matter, a culture of a particular type of bacteria is incubated in the presence of a P-PMO+ of the type described above, in an amount effective to produce replication-crippled and/or morphologically abnormal bacterial cells. Such replication-crippled and/or morphologically abnormal bacterial cells are administered to a subject and act as a vaccine.

The efficacy of an in vivo administered antisense oligomer of the claimed subject matter in inhibiting or eliminating the growth of one or more types of bacteria may be determined by in vitro culture or microscopic examination of a biological sample (tissue, blood, etc.) taken from a subject prior to, during and subsequent to administration of the P-PMO+. (See, for example, (Pari, Field et al. 1995); and (Anderson, Fox et al. 1996). The efficacy of an in vivo administered vaccine of P-PMO+-treated bacteria may be determined by standard immunological techniques for detection of an immune response, e.g., ELISA, Western blot, radioimmunoassay (RIA), mixed lymphocyte reaction (MLR), assay for bacteria-specific cytotoxic T lymphocytes (CTL), etc.

A. Administration Methods

Effective delivery of the P-PMO+ to the target nucleic acid is an important aspect of treatment. In accordance with the claimed invention, such routes of delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of a P-PMO+ in the treatment of a bacterial infection of the skin is topical delivery; while delivery of a P-PMO+ in the treatment of a bacterial respiratory infection is by inhalation. Methods effective to deliver the oligomer to the site of bacterial infection or to introduce the compound into the bloodstream are also contemplated.

Transdermal delivery of P-PMO+ may be accomplished by use of a pharmaceutically acceptable carrier adapted for e.g., topical administration. One example of morpholino oligomer delivery is described in PCT patent application WO 97/40854, incorporated herein by reference.

In one preferred embodiment, the compound is a P-PMO+, contained in a pharmaceutically acceptable carrier, and is delivered orally.

The P-PMO+ may be administered in any convenient vehicle which is physiologically acceptable. Such a composition may include any of a variety of standard pharmaceutically accepted carriers employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

In some instances liposomes may be employed to facilitate uptake of the antisense oligonucleotide into cells. (See, e.g., Williams, S. A., *Leukemia* 10(12):1980-1989, 1996; Lappalainen et al., *Antiviral Res.* 23:119, 1994; Uhlmann et al., ANTISENSE OLIGONUCLEOTIDES: A NEW THERAPEUTIC PRINCIPLES, *Chemical Reviews*, Volume 90, No. 4, pages 544-584, 1990; Gregoriadis, G., Chapter 14, Liposomes, *Drug Carriers in Biology and Medicine*, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., *J. Biol. Chem.* 262:4429-4432, 1987.)

Sustained release compositions are also contemplated within the scope of this application. These may include semipermeable polymeric matrices in the form of shaped articles such as films or microcapsules.

Typically, one or more doses of P-PMO+ are administered, generally at regular intervals for a period of about one to two weeks. Preferred doses for oral administration are from about 10 mg oligomer/patient to about 250 mg oligomer/patient (based on a weight of 70 kg). In some cases, doses of greater than 250 mg oligomer/patient may be necessary. For IV administration, the preferred doses are from about 1.0 mg oligomer/patient to about 100 mg oligomer/patient (based on an adult weight of 70 kg). The P-PMO+ is generally administered in an amount and manner effective to result in a peak blood concentration of at least 200-400 nM oligomer.

In a further aspect of this embodiment, a P-PMO+ is administered at regular intervals for a short time period, e.g., daily for two weeks or less. However, in some cases the P-PMO+ is administered intermittently over a longer period of time. Administration of a P-PMO+ to a subject may also be followed by, or concurrent with, administration of an antibiotic or other therapeutic treatment.

In one aspect of the method, the subject is a human subject, e.g., a patient diagnosed as having a localized or systemic bacterial infection. The condition of a patient may also dictate prophylactic administration of a P-PMO+ of the claimed subject matter or a P-PMO+-treated bacterial vaccine, e.g. in the case of a patient who (1) is immunocompromised; (2) is a burn victim; (3) has an indwelling catheter; or (4) is about to undergo or has recently undergone surgery.

In another application of the method, the subject is a livestock animal, e.g., a chicken, turkey, pig, cow or goat, etc, and the treatment is either prophylactic or therapeutic. The invention also includes a livestock and poultry food composition containing a food grain supplemented with a subtherapeutic amount of an antibacterial antisense compound of the type described above. Also contemplated is in a method of feeding livestock and poultry with a food grain supplemented with subtherapeutic levels of an antibiotic, an improvement in which the food grain is supplemented with a subtherapeutic amount of an antibacterial oligonucleotide composition as described above.

The methods of the invention are applicable, in general, to treatment of any condition wherein inhibiting or eliminating the growth of bacteria would be effective to result in an improved therapeutic outcome for the subject under treatment.

One aspect of the invention is a method for treatment of a bacterial infection which includes the administration of a morpholino antisense oligomer to a subject, followed by or concurrent with administration of an antibiotic or other therapeutic treatment to the subject.

B. Treatment Monitoring Methods

It will be understood that an effective in vivo treatment regimen using the P-PMO+ compounds of the invention will vary according to the frequency and route of administration, as well as the condition of the subject under treatment (i.e., prophylactic administration versus administration in response to localized or systemic infection). Accordingly, such in vivo therapy will generally require monitoring by tests appropriate to the particular type of bacterial infection under treatment and a corresponding adjustment in the dose or treatment regimen in order to achieve an optimal therapeutic outcome.

The efficacy of a given therapeutic regimen involving the methods described herein may be monitored, e.g., by general indicators of infection, such as complete blood count (CBC), nucleic acid detection methods, immunodiagnostic tests, or bacterial culture.

Identification and monitoring of bacterial infection generally involves one or more of (1) nucleic acid detection methods, (2) serological detection methods, i.e., conventional immunoassay, (3) culture methods, and (4) biochemical methods. Such methods may be qualitative or quantitative.

Nucleic acid probes may be designed based on publicly available bacterial nucleic acid sequences, and used to detect target genes or metabolites (i.e., toxins) indicative of bacterial infection, which may be specific to a particular bacterial type, e.g., a particular species or strain, or common to more than one species or type of bacteria (i.e., Gram positive or Gram negative bacteria). Nucleic amplification tests (e.g., PCR) may also be used in such detection methods.

Serological identification may be accomplished using a bacterial sample or culture isolated from a biological specimen, e.g., stool, urine, cerebrospinal fluid, blood, etc. Immunoassay for the detection of bacteria is generally carried out by methods routinely employed by those of skill in the art, e.g., ELISA or Western blot. In addition, monoclonal antibodies specific to particular bacterial strains or species are often commercially available.

Culture methods may be used to isolate and identify particular types of bacteria, by employing techniques including, but not limited to, aerobic versus anaerobic culture, growth and morphology under various culture conditions. Exemplary biochemical tests include Gram stain (Gram, 1884; Gram positive bacteria stain dark blue, and Gram negative stain red), enzymatic analyses (i.e., oxidase, catalase positive for *Pseudomonas aeruginosa*), and phage typing.

It will be understood that the exact nature of such diagnostic, and quantitative tests as well as other physiological factors indicative of bacterial infection will vary dependent upon the bacterial target, the condition being treated and whether the treatment is prophylactic or therapeutic.

In cases where the subject has been diagnosed as having a particular type of bacterial infection, the status of the bacterial infection is also monitored using diagnostic techniques typically used by those of skill in the art to monitor the particular type of bacterial infection under treatment.

The P-PMO+ treatment regimen may be adjusted (dose, frequency, route, as indicated, based on the results of immunoassays, other biochemical tests and physiological examination of the subject under treatment.

From the foregoing, it will be appreciated how various objects and features of the invention are met. The method provides an improvement in therapy against bacterial infection, using P-PMO+ sequences to achieve enhanced cell uptake and anti-bacterial action. As a result, drug therapy is more effective and less expensive, both in terms of cost and amount of compound required.

An important advantage of the invention is that compounds effective against virtually any pathogenic bacterium can be readily designed and tested, e.g., for rapid response against new drug-resistant bacteria, or in cases of bioterrorism. Once a target bacterium is identified, the sequence selection methods described allow one to readily identify one or more likely gene targets, among a number of essential genes, and prepare antisense compounds directed against the identified target. Because clinical testing on the safety and efficacy, once established for a small group of compounds, can be extrapolated to virtually any new target, relatively little time is needed in addressing new bacterial-infection challenges as they arise.

The following examples are intended to illustrate but not to limit the invention.

Materials and Methods

Unless otherwise noted, all chemicals were obtained from Sigma-Aldrich-Fluka. Benzoyl adenosine, benzoyl cytidine, and phenylacetyl guanosine were obtained from Carbosynth Limited, UK Example 1

Morpholino Subunits

See FIG. 2B

General Preparation of morpholino salts 3a-d,f: To a cooled mixture of methanol (5-10 mL/g ribonucleosides 2) was added a warm aqueous solution of sodium meta-periodate (1.05 eq). At this stage, the composition of the reaction mixture will be from 1540% water/methanol (v:v). To this mixture was added, in portions, solid 1a-d,f. Upon reaction completion (1-2 hr), the by-product sodium iodate cake was removed by filtration and reslurried with water/methanol to recover any product intermediate. To the pooled filtrates were added ammonium biborate (14-2.0 eq). After stirring at 20° C. for 45-120 min, the mixture was cooled, and borane-triethylamine (1.5-2.0 eq) was added. This mixture was adjusted to pH 3.5-4.0 with a methanolic solution of either p-toluenesulfonic acid [3b, c, d, f] or hydrochloric acid [3a] (4-5 eq). The mixture was held at pH 3.5-4.0 for 7-14 hr at <10° C. The p-toluenesulfonic acid salts of 3b, c, d, f were isolated by filtration and purified by recrystallization/reslurry.

The mixture containing 3a was neutralized to pH 7. The solution was concentrated by distillation to remove methanol, and the product was extracted into 1-butanol. This solution was adjusted to pH 4 with a methanolic solution of oxalic acid (0.5 eq). The oxalic acid salt of 3a was isolated by filtration and purified by reslurry. Yields for 3a-d,f=30-75%.

General Preparation of 1a-d,f: Compound 3a-d,f was dissolved/suspended in N,N-dimethylformamide (4-6 mL/g 3). To this mixture was added triethylamine (2.7-3.5 eq) and triphenylmethyl(trityl)chloride (1.1-1.5 eq). Upon reaction completion, the excess trityl chloride was quenched with diethylamine (0.5 eq). The crude products were isolated by either direct precipitation from ethyl acetate and water or through an extractive workup (water then ethyl acetate or dichloromethane) and precipitation. The products were purified by crystallization from toluene. Yields=75-90%

Preparation of 1e: Compound 1f was suspended in dichloromethane (8 mL/g 1f). To this suspension were added imidazole (1.3 eq) and t-butyldimethylchlorosilane (1.2 eq). Upon reaction completion (1-2 hr), the solution was washed successively with pH 3 citrate buffer and water. The resulting solution was concentrated to give a foam, which was dissolved in tetrahydrofuran (8 mL/g 1f). To this solution were added potassium carbonate (2.0 eq) and chloromethyl pivalate (1.5 eq) and the mixture was heated to reflux. Upon reaction completion (16 hr), the mixture was cooled and diluted with dichloromethane. The mixture was washed successively with $KH_2PO_4$ solution (pH 4.5) and water. The resulting solution was concentrated to give a foam. The foam was dissolved in tetrahydrofuran (4 mL/g 1f) and triethylamine trihydrofluoride (2.0 eq) was added. Upon reaction completion (16 hr), the solution was washed successively with saturated aqueous $NaHCO_3$ and water. The product was isolated by solvent exchange into toluene and precipitation into heptane. Yield=80% of 1e.

Example 2

Morpholino Subunits with Linkage Type (a)

See FIG. 2C

General Preparation of 5a-e: Compound 1a-e was dissolved in dichloromethane (6 mL/g 1) and cooled to <5 C. To this solution were added 2,6-lutidine (1.6 eq), N-methylimidazole (0.3 eq), and N,N-dimethylphosphoramidodichloridate 4 (1.6 eq). Upon reaction completion (6-12 hr), this mixture was washed with a pH 3 citrate buffer. The crude product was isolated by precipitation into heptane. The final product was purified by silica gel chromatography (gradient of ethyl acetate/heptane). The pooled fractions containing product were combined, evaporated to a smaller volume, and isolated by precipitation from heptane. Yields=40-60%. During the chromatography of subunit 5e, as well as other subunits derived from this heterocyclic base, following ethyl acetate/heptane elution of the non-polar impurities, a gradient of (5% isopropanol/ethyl acetate) in dichloromethane was used to elute the product.

Example 3

Morpholino Subunits with Pro-Cationic Linkages Type (b1)

See FIG. 2D

Preparation of N-trityl piperazine, succinate salt (11): To a cooled solution of piperazine (10 eq) in toluene/methanol (5:1 toluene/methanol (v:v); 5 mL/g piperazine) was added slowly a solution of trityl chloride 10 (1.0 eq) in toluene (5 mL/g trityl chloride). Upon reaction completion (1-2 hr), this solution was washed four times with water. To the resulting organic solution was added an aqueous solution of succinic acid (1.1 eq; 13 mL water/g succinic acid). This mixture was stirred for 90 min, and the solid product was collected by filtration. The crude solid was purified by two reslurries in acetone. Yield=70%.

Preparation of 1-trifluoroacetyl-4-trityl piperazine (14): To a slurry of 3.0 kg 11 in 18 L methanol (6 mL/g 11) was added 3.51 L diisopropylethylamine (3.0 eq) and 1.038 L ethyl trifluoroacetate 13a (1.3 eq). After overnight stirring, the organic mixture was distilled to dryness. The resulting oil was dissolved in 15 L dichloromethane (5 mL/g 11) and washed twice with 15 L 1M $KH_2PO_4$ and twice with 15 L de-ionized water. This solution was run through a 3.0 kg silica plug (1:1 silica: 11), and washed with 9 L dichloromethane (3 ml/g 11, then concentrated to give a white foam. For 14a: Yield=2.9964 kg, 105%. $^{19}F$ NMR (CDCl$_3$) □-68.7 (s).

For the preparation of 2,2-difluoropropionyl and hexafluoroisobutyryl amides, trityl piperazine succinate 11 in dichloromethane was reacted with an aqueous solution of potassium carbonate to remove succinic acid. The dichloromethane was evaporated and the tritylpiperazine free base 12 was treated with 2 eq of the ester 13c or 13d (both obtained from Synquest, Alachua, Fla., USA) without solvent in the presence of diisopropylethylamine (1.0 eq). The mixture was heated at 40° C. until complete. The mixture was dissolved in dichloromethane and passed through a plug of silica gel, eluting with ethyl acetate and heptane mixtures to provide the pure trityl piperazine amides.

Preparation of N-trifluoroacetyl piperazine, HCl salt (15): To a solution of 1.431 kg 14 in 7.16 L dichloromethane (5 mL/g 14) was added dropwise a solution of 3.37 L 2.0 M HCl/Et$_2$O (2.0 eq). The reaction mixture was stirred for 1 hr, and the product was collected by filtration. The filter cake was washed with 2.0 L dichloromethane. The solids were dried at 40° C. in a vacuum oven for 24 hr. For 15a: Yield=724.2 g, 98.3%. $^{19}F$ NMR (CDCl$_3$) □-68.2 (s); melting point=140° C. Recrystallization of a small sample from ethanol raised the melting point to 154-156° C.

Preparation of Activating Agent (6): To a cooled suspension of 15 (1.0 eq) in Toluene (10 mL/g 15) was added diisopropylethylamine (4.0 eq). The mixture was stirred in an ice bath for 1 hr and the salts were removed by filtration. The filter cake was washed twice with toluene (1.5 mL/g). The toluene solution of 15 free base (13 mL/g) was added slowly to a ice cooled solution of POCl$_3$ (1.2 eq) in toluene. The reaction mixture was stirred in an ice bath for 1 hr, then washed twice with 1 M KH$_2$PO$_4$ (13 mL/g) and once with and de-ionized water (13 mL/g). This solution was dried over Na$_2$SO$_4$ and distilled to dryness. The resulting amorphous solid was dissolved in dichloromethane (2 mL/g 15) and again distilled to dryness. For a 200 g batch of 15a the yield was of 6a was 226.9 g, 75%. $^{19}$F NMR (CDCl$_3$) □ −68.85 (S); $^{31}$P NMR (CDCl$_3$) □ 15.4 (s).

Preparation of Activated Subunits (7) (See FIG. 2C): To a cooled solution/slurry of morpholino subunit 1a-e (1.0 eq) in dichloromethane (5 mL/g subunit) were added successively 2,6-lutidine (1.6 eq), N-methylimidazole (0.3 eq), and 6a-d (1.6 eq) in dichloromethane (2 ml/g 6). The solution was allowed to warm to room temperature. After 3 hr, the solution was washed with 1M citric acid (pH 3). The organic layer was dried over Na$_2$SO$_4$, the solvents removed by distillation and toluene (5 mL/g) added. The product was precipitated by dropwise addition of the solution into heptanes (20 ml/g subunit) then collected by filtration. The crude product was purified by silica gel chromatography (gradient of ethyl acetate/heptane). The solvents were concentrated and replaced with toluene or ethyl benzene (5 ml/g subunit). The amorphous product was precipitated into heptane (20 ml/g subunit) then collected by filtration. Yield=50-70%. $^{19}$F NMR CDCl$_3$ shows one or two peaks with chemical shifts at about □-68.8; 31p NMR (CDCl$_3$) typically shows two singlet peaks with chemical shifts at 13.0 to 13.4.

Example 4

Morpholino Subunits with Pro-Cationic Linkages Type (b2)

See FIG. 2C

Primary Amine Containing Side Chain:

Hexamethylenediamine (100 g, 1 eq) was dissolved in methanol (1 L) and treated dropwise with a solution of ethyl trifluoroacetate (103 mL, 1 eq) in 150 mL methanol. Very slight warming of the solution occurs. The reaction was stirred for 30 min at room temperature after addition. TLC using chloroform/methanol/conc ammonia (8:3:1) shows the presence of amine. The solvents were removed by rotary evaporation, and the residue dissolved in toluene/ethyl acetate (1:3, 1 L) then washed four times with 10% saturated aqueous sodium chloride solution to effect complete removal of excess diamine. Evaporation yields 117 g crude amine which was used in the activation reaction as for the piperazine example above. Crude 8a was reacted with 1a using the conditions above to give 9a. The corresponding reaction with the other subunits produces 9b-e. The alternate amide protected amines were prepared and used in the same manner as previous examples, with amides from esters 13c,d formed by reaction of the amine with neat ester.

Secondary Amine Containing Side Chain:

N,N'-Dimethylethylenediamine (36.3 mL, 3 eq.) was mixed with trityl chloride (31.8 g, 1 eq.) in dichloromethane (300 mL). After 30 min the solvent was removed by evaporation and 300 mL toluene was added. The solution was washed three times with 300 mL water and finally with an equal volume of saturated aqueous sodium chloride. The foam formed on evaporation was used without purification.

The foam was dissolved in 400 mL methanol and 100 mL dichloromethane. Ethyl trifluoroacetate (17.5 mL) was added. After 30 min, the mixture was evaporated to dryness, 300 mL dichloromethane added, and the solution washed three times with an equal volume of water, and then once with saturated aqueous sodium chloride. After drying over sodium sulfate, the organic layer was evaporated to dryness. The product was purified by silica chromatography using 10% ethyl acetate heptane containing 1% lutidine to afford 24.8 g pure trityl amide.

The trityl amide was dissolved in dichloromethane (180 mL) and treated dropwise with 2 M HCl in ether (85 mL) and stirred at room temperature for 3 hr. The precipitated solid was filtered and dried overnight under high vacuum. The recovered product (10.06 g) was suspended in 100 mL dichloromethane and treated with diisopropylethylamine (25.0 mL) at which time a solution formed. This mixture was added to phosphorus oxychloride (4.6 mL) in toluene (100 mL) with stirring at 0° C. in an ice bath. The reaction was continued 12 hr at room temperature. At that time, the reaction was washed twice with 1 M KH$_2$PO$_4$ (100 mL), and dried over sodium sulfate. After filtration and evaporation a brown solid was obtained that was used directly.

The brown solid was dissolved in 20 mL dichloromethane and added to a solution of 1d (13.6 g) in dichloromethane (40 mL) containing 2,6-lutidine (5.24 mL) and N-methylimidazole (0.672 mL). After four hr at room temperature, the reaction was washed twice with 1 M citric acid buffer at pH=3. The solution was evaporated to dryness and the product purified by chromatography on silica using an ethyl acetate/heptane gradient. Similar reactions afford the corresponding protected N-methyl-N-methylaminoethyl substituted activated subunits.

Example 5

Morpholino Subunits with Pro-Cationic Linkages Type (b3)

See FIG. 2E

Oxidation of 1: All glassware was oven dried overnight and cooled under vacuum or with a stream of N$_2$. All solutions were prepared and transferred under N$_2$. The starting alcohol (1) was dried under vacuum at 50° C. for 24 hr prior to use.

A solution of 1 (1 eq; 25 mmol) in DMSO/dichloromethane (1:2 DMSO/dichloromethane (v:v); 5 mL/g 1) was added dropwise over 15 min to the Swern reagent (prepared by adding DMSO (2.2 eq) to a solution of oxalyl chloride (1.1 eq) in dichloromethane (21 mL/g) at −60° C. and stirring for 10 min). After stirring at −60° C. for 25 min, triethylamine (5 eq) was added over 10 min during which time a white precipitate formed. Additional dichloromethane (5 mL/g 1) was added and the reaction mixture stirred in a water bath for 25 min.

The reaction mixture was diluted with isopropanol/dichloromethane (1:15 isopropanol/dichloromethane (v:v); 15 mL/g 1) and washed twice with 1:1 (v:v) water/brine (20 ml/g 1). The solution was dried over Na$_2$SO$_4$ and concentrated to give the aldehydes 16a-e as pale yellow foams which were used without further purification. Yield=>100%.

Reductive Amination of 16:

A solution of methylamine acetate (10 eq; 1.16 M solution in methanol) was added to a solution of 16a-e (1 eq; 25 mmol) in methanol (8 mL/mmol 16). After adjustment to pH 8 with glacial acetic acid, the reaction mixture was stirred at room temperature for 1 hr and BH$_3$ pyridine (2 eq) was added. After stirring for a further 1 hr, the reaction mixture was concentrated to a viscous oil. To the crude product dissolved in dichloromethane (10 mL/mmol 16) was added 9-fluorenylmethyl chloroformate (FMOC chloride) (1.5 eq) followed by diisopropylethylamine (2.5 eq) and the solution stirred at room temperature for 30 min. The reaction mixture was diluted with dichloromethane (8 mL/mmol) and washed twice with 1:1 (v:v) water/brine (20 ml/mmol 16). The solution was dried over Na$_2$SO$_4$, the solvent removed and the crude product was purified by silica gel chromatography (gradient of acetone/chloroform). Yield=40-60% of 18a-e.

A solution of 18 (1 eq; 2.8 mmol) in 1% 1,8-diazabicyclo [5.4.0]undec-7-ene (DBU)/N,N-dimethylformamide (5 mL/g 18) was stirred at room temperature for 30 min. The reaction mixture was diluted with chloroform (15 mL/g 18) and washed with 1:1 (v:v) water/brine (10 mL/g 18). The aqueous phase was re-extracted once with chloroform (10 mL/g 18), the combined organic solutions dried over Na$_2$SO$_4$ and the solvent removed. The residue was dissolved in N,N-dimethylformamide (15 mL/g 18), washed six times with hexanes (15 mL/g 18) to remove/reduce the dibenzofulvene by-product and the solvent removed to give the product 17a-e as an off-white solid. Yield=85%

Freshly distilled ethyl phosphorodichloridate (3 eq) was added dropwise over 3 min to a solution of 17 (1 eq; 2.3 mmol) and diisopropylethylamine (3 eq) in dry dichloromethane (40 mL/g 17) under N$_2$ at 0° C. The cooling bath was removed and the reaction mixture was stirred at room temperature until complete by TLC (30 min). After removal of the solvent, the crude product was purified directly by silica gel chromatography (ethyl acetate/hexane gradient). Yield=50-60%. This subunit is useful for introduction of uncharged linkages of type (a). This general method was applied below for the introduction of charges linkages of type (b3).

Reductive amination with a long chain ethereal diamine with the T subunit: 4-Methoxytriphenylmethyl chloride (15.4 g, 50 mmol) was dissolved in toluene and added dropwise to a stirred solution of 4,7,10-trioxa-1,13-tridecaneamine (150 mmol) in dichloromethane containing 50 mmol triethylamine. Reaction completion was conveniently followed by TLC eluting with ethanol/conc ammonia (4:1, v/v) and visualizing with ninhydrin or UV. When the reaction was done, the solution was washed with water to remove the free amine. The solvent was removed by evaporation and the crude product used without purification in the next step. Ethyl trifluoroacetate (1.5 eq) was added to a solution of methoxytritylated amine (1 eq; 25 mmol) and triethylamine (1.5 eq) in dichloromethane (12 mL/g amine) at 0° C., the cooling bath was removed and the reaction mixture stirred at room temperature for 4 hr. On reaction completion (TLC), the reaction mixture was diluted with dichloromethane (12 ml/g amine) washed twice with 1:1 (v:v) water/brine (20 ml/g 1), dried over Na$_2$SO$_4$ and concentrated to a viscous pale yellow oil. The crude methoxytritylated amide product was purified by silica gel chromatography (gradient of ethyl acetate/chloroform). Yield=60-70%.

p-Toluenesulfonic acid (1.5 eq) was added to solution of methoxytritylated amide (3 eq; 7.5 mmol) in methanol/trifluoroethanol/dichloromethane (1:10:89 (v:v:v); 5 ml/g 2) and the yellow-orange solution stirred at room temperature for 30 min when reaction was complete (TLC). The reaction mixture was neutralized to pH 7 with triethylamine and evaporated. The crude product was redissolved in methanol (5 mL/g methoxytritylated amide), the pH adjusted to pH 7 if necessary and re-evaporated. The methanol addition and evaporation was repeated once more and the crude amine used without further purification.

The aldehyde 16d (1 eq; 2.5 mmol) was added to a solution of the crude amine in methanol (5 mL/g crude amine; 12.5 mL/g 16d) and the pH adjusted to pH 8 with acetic acid. The reaction mixture was stirred at room temperature for 1 hr and borane-pyridine (2 eq) added. The pH was adjusted, if necessary, to maintain the starting pH and the reaction mixture stirred for 1 hr or until complete by TLC. The reaction mixture was evaporated, the residue dissolved in dichloromethane (12.5 mL/g 16d) and 9-fluorenylmethyl chloroformate (2 eq) and diisopropylethylamine (3 eq) added and the reaction mixture stirred at room temperature for 45 min. The reaction mixture was partitioned between dichloromethane and 1:1 (v:v) water/brine (12.5 mL/g 16d of each) and the aqueous phase re-extracted with dichloromethane (12.5 mL/g 16d). The combined organics were washed with saturated aqueous sodium chloride (25 mL/g 16d), dried over Na$_2$SO$_4$ and the solvent removed. The crude product was purified by silica gel chromatography (gradient of methanol/chloroform) to give product 21d as a white foam. Yield=40%.

Deprotection:

A solution of crude 21d (1 eq; 0.9 mmol) in 20% triethylamine/N,N-dimethylformamide (15 mL/mmol 21d) was heated at 50° C. for 30 min when no 21d remained by TLC. The cooled reaction mixture was extracted four times with hexanes (30 mL/mmol 21d) to remove the dibenzofulvene by-product and the solvent removed. The residue was dissolved in isopropanol (15 mL/mmol 21d), evaporated to a foam then dissolved in a minimum volume of dichloromethane and precipitated from hexanes (150 mL/g 21d) to give the product 20d as an off white solid. Yield=90%.

Activation:

A solution of 20d (1 eq; 0.78 mmol) and diisopropylethylamine (3 eq) was prepared in dry dichloromethane (20 mL/g 20d) under nitrogen and added dropwise over ~3 min to a solution of ethyl phosphorodichloridate (3 eq) in dry dichloromethane (20 mL/g 20d) under N$_2$ at 0° C. The cooling bath was removed and the reaction mixture was stirred at room temperature until complete by TLC (20 min). The solution was concentrated to approximately ½ volume and purified directly by silica gel chromatography (acetone/chloroform gradient). Yield=40-50% of 22d.

Reductive Amination with a Long Chain Ethereal Diamine with the C Subunit:

Subunit 1b was oxidized by an alternative method. The subunit (5 g, 1 eq) was added to a solution formed by adding pyridine (9.15 eq) then trifluoroacetic acid (4.58 eq). The solution placed in room temperature water bath and stirred. When the solution was clear, diisopropylcarbodiimide (7.23 eq) was added slowly. After two hr, the solution was added to 800 mL of saturated aqueous sodium chloride solution. After stirring for 20 min, the mixture was filtered. The product was dissolved in acetone and precipitated into de-ionized water. The filtered product was dried under vacuum. The yield was 70-80%. The oxidized subunit may be used as is, but may be purified by chromatography on silica using ethyl acetate/dichloromethane mixtures.

The diamine 4,7,10-trioxa-1,13-tridecaneamine (33 g, 1 eq) was dissolved in 150 mL diethyl ether, cooled to 0° C., and the solution treated slowly with a solution of ethyl trifluoroacetate (32 g, 1.5 eq) in 50 mL ether. TLC indicates reaction completion with only traces of diamine remaining.

A portion of this solution (45 mL, 3 eq amine relative to aldehyde) was added to a stirred solution of 3.42 g 16b in 20 mL methanol. After five min was added p-nitrophenol (2.52 g), and after 20 min was added sodium cyanoborohydride (3.2 g, 8 eq). After 160 min at room temperature additional sodium cyanoborohydride (1.2 g) and nitrophenol (0.8 g) were added. The solution was poured into 800 mL of room temperature water, giving a suspension of solids and viscous oil. The water was removed by decantation and the product dried in vacuo. The entire product was dissolved in ethyl acetate and applied to 250 mL silica gel packed in the same solvent. The column was washed with 2% triethylamine/ethyl acetate and the product eluted with a 1% solution of triethylamine in 6:1 to 10:1 ethyl acetate:ethanol mixture. The fractions containing product were evaporated dried in vacuo to yield 1.95 g, 37% of the amine 20b.

The activated 5'-amino C subunit with the long chain ethereal side chain amine was prepared as described above for the T compound.

Example 6

Morpholino Subunits with Type (b3) Pro-Cationic Linkages by Alkylation

See FIG. 2F

Hexamethylenediamine (100 g) was dissolved in methanol (1 L) and treated dropwise with a solution of ethyl trifluoroacetate (103 mL) in 150 mL methanol. Very slight warming of the solution occurs. The reaction was stirred for 30 min at room temperature after addition. TLC using chloroform/methanol/conc ammonia (8:3:1) shows the presence of amine. The solvents were removed by rotary evaporation, the residue dissolved in toluene/ethyl acetate (1:3, 1 L) then washed four times with 10% saturated aqueous sodium chloride solution to effect complete removal of excess diamine. Evaporation yields 117 g crude amine which was used directly with the tosylated subunit formed below.

Subunit 1b (20 g) dissolved in dichloromethane (200 mL) was treated with N-methylimidazole (11 mL) and the mixture cooled in an ice bath. p-Toluenesulfonyl chloride (8 g) was added in one step, the solution stirred for 10 min, and the flask placed at 4° C. for 16 hr. TLC (2% methanol in dichloromethane) indicates reaction completion. The reaction was worked up by adding 300 mL dichloromethane and washing with three times 300 mL of 10% saturated aqueous sodium chloride, and evaporating to yield 23b as a foam.

The tosylate 23b (17 g) and the monoprotected amine (46.5 g, containing some bis acylated diamine) were mixed in acetonitrile (200 mL) along with triethylamine (15 mL). Following 16 hr at 45° C., the mixture was evaporated and the residue resuspended in N,N-dimethylformamide (200 mL). The mixture became homogenous at 45° C. The solution was heated for 5 days, at which time it was cooled to ambient temperature, and mixed with 1 L of 10% saturated aqueous sodium chloride and 800 mL ethyl acetate. The organic layer was washed with 1 L 20% saturated aqueous sodium chloride, stirred with sodium sulfate, filtered and evaporated to 48 g of alkylation product, which contains a mixture of benzoylated and debenzoylated heterocyclic base.

A portion of the crude product above (9 g) was suspended in dichloromethane, cooled to 0° C., and treated with a solution of N-(9-fluorenylmethoxycarbonyloxy)succinimide (FMOC-OSu) (Chemical Abstracts number 82911-69-1) in 40 mL dichloromethane. The reaction was complete after 20 minute. To the solution was added 3.3 mL N-methylimidazole then 1.9 mL of benzoyl chloride to re-protect debenzoylated species. After 10 more min at 0° C., the reaction was allowed to warm to room temperature. The reaction was diluted with 150 mL dichloromethane, washed with 250 mL pH=7 phosphate buffer, washed twice with 250 mL 10% saturated aqueous sodium chloride, dried over sodium sulfate, and evaporated. The residue was loaded onto 500 mL silica using dichloromethane (3 L), and eluted with mixtures of ethyl acetate in dichloromethane (1 L each of 5%, 10%, 15%, 2 L of 20%, 2 L of 40%) The last eluent provided 2.9 g of pure benzoylated FMOC protected 5'-amino subunit 24b.

Washing the column with 2 L of 5% methanol/dichloromethane allowed the recovery of 5.4 g of the debenzoylated FMOC protected 5'-amino subunit.

The FMOC group was removed from the product above (7.1 g) by treatment with piperidine (28 mL) in DMF (140 mL). After 5 min at room temperature, the reaction was partitioned between dichloromethane (400 mL) and water (30 mL). The organic layer was washed three times with 400 mL 10% saturated aqueous sodium chloride. Evaporation provided 8.8 g crude free amine, purified by chromatography on silica (360 mL), using dichloromethane (1 L), 30% ethyl acetate/dichloromethane (2 L), and 5% methanol/dichloromethane (3 L) to provide 2.5 g of amine product.

One gram of this amine was dissolved in dichloromethane (10 mL) at 0° C. and treated successively with N-ethylmorpholine (500 mL), then ethyl phosphorodichloridate (230 mL). Triethylamine (227 mL) was added and the mixture became homogeneous. The reaction was complete after 4 hr. After the usual aqueous workup the product was purified by silica chromatography (60 mL) using 10-50% ethyl acetate/heptane mixtures to give 800 mg of the activated subunit 25b.

The same process was used to make the activated T subunit with protected hexamethylene diamine side chain at the 5'-position. Subunit 1d (50 g) was reacted with p-toluenesulfonyl chloride (23.7 g) in dichloromethane (500 mL) and N-methylimidazole (16.5 mL). After one hr at 0° C. and 4 hr at room temperature, the reaction was diluted with 400 mL dichloromethane and washed with three times with 1 L of 10% saturated aqueous sodium chloride. After drying over sodium sulfate and evaporation the residue weighed 57 g. The residue (15 g) and 40 g of the crude mono(trifluoroacetylated) hexamethylene diamine were reacted at reflux overnight in 100 mL acetonitrile. The residue after evaporation was dissolved in 2% methanol/dichloromethane and applied to silica. The column was eluted with dichloromethane, 50% ethyl acetate/dichloromethane, ethyl acetate, 80% ethyl acetate/dichloromethane, and finally 5% methanol/dichloromethane to elute the product in >98% purity. One gram of this product was activated and purified as above to yield 300 mg (25%) of the activated subunit 25d.

In a similar fashion, 1a-e were reacted with 3,3'-diamino-N-methyldipropylamine, 26 which affords a side chain with two cationic sites as in 27a-e.

Example 7

Morpholino Subunits with Pro-Cationic Sulfamide Linkages

See FIG. 2G

The 5'-methylamino subunit 17a-e (1 eq) in dimethylformamide (10 mL/g) was treated with sulfur trioxide/pyridine (4 eq), pyridine (8 eq) followed by triethylamine (6 eq). After 16 hr, the reaction was added to excess saturated aqueous sodium chloride and the dried precipitate chromatographed on silica using 5% methanol/chloroform and containing 2% triethylamine. The triethylammonium salt of the sulfamic acid 28a-e so isolated was dissolved in dichloromethane (20 mL/g). Pyridine (3.2 eq) was added and the mixture cooled under nitrogen in a dry-ice acetone batch. The solution was treated dropwise with 1.1 eq phosgene in toluene solution. After 25 min, the solution was allowed to warm to room temperature over 20 min. The solution was rotary evaporated to an oil that was dissolved in chloroform and directly chromatographed on silica using 40% ethyl acetate and hexane.

The product 29a-e obtained in 50% yield, was used for the introduction of sulfamide linkages of type (a). The 5'-amino subunit from hexamethylene diamine (24a-e) was deprotected, sulfated and activated in a similar fashion to provide 30a-e.

Example 8

Preparation of Disulfide Anchor

See FIG. 2H

Preparation of symmetrical disulfide 32: 1,1'-Carbonyldiimidazole (CDI) (12.402 g; 2.2 eq.) was suspended in dichloromethane (5.25 mL/g) and cooled on an ice bath. Hydroxyethyl disulfide 31 (5.36 g; 1 eq.) was dissolved in dichloromethane (10 mL/g) and tetrahydrofuran (1 mL/g). The diol solution was added to the CDI slowly such that the temperature of the mixture stayed below 4° C. for the duration of the reaction. Upon reaction completion (once addition was complete), de-ionized water (93.8 µL, 0.15 eq.) was added to quench the reaction. Independently, 11 (32.59 g; 2.1 eq.) was dissolved in toluene (8 mL/g 11), dichloromethane (2 mL/g 11), and methanol (2 mL/g 11). $K_2CO_3$ (22.09 g; 4.6 eq.) was dissolved in de-ionized water (10 mL/g). The $K_2CO_3$ solution added to the solution of 11; the mixture was stirred and then separated into two layers. The cloudy organic layer was distilled to remove 90 grams; the resulting water droplets were separated and acetone (8 mL/g 11) was added to the organic layer. The solution of CDI activated disulfide diol was added to the solution of free base 12 and concentrated to 225 mL. Acetone (10 mL/g 11) was added and the mixture was concentrated to 225 mL. The mixture was heated to reflux and solid began crystallizing out of solution. Upon completion, the reaction mixture was cooled and the solid (32) was isolated by filtration. Yield: 27.92 g; 93.1% (based on weight-based assay).

Preparation of disulfide alcohol 33: 32 (36.00 g; 32.1 mmol; 1 eq.) was suspended in acetone (2.8 mL/g 32). Hydroxyethyl disulfide (78.51 mL; 20 eq.) was added followed by acetone (1.7 mL/g 32). 5% NaOH/methanol (2.85 mL; 0.1 eq.) was added; the pH of the mixture was 10 by pH paper. Triphenylphosphine (8.42 g; 1 eq.) was added followed by acetone (1.1 mL/g 32). All solids went into solution and then product began to crystallize out. After sixteen hr, the reaction mixture was neutralized with acetic acid (2.4 g; 0.2 eq.). The crude product was isolated by filtration. The crude solid 33 was subjected to two refluxing acetone reslurries (5 mL/g).

After filtration the crude product was suspended in dichloromethane (7.25 mL/g 32). The mixture was heated until a clear solution formed (35° C.). The solution was extracted five times with an equal volume of de-ionized water and the final organic layer was concentrated to 155 mL. Dichloromethane was added (4.3 mL/g 32), and the solution was again concentrated to 155 mL. CDI (9.17 g; 1.1 eq.) was added and the mixture was stirred at room temperature. Upon reaction completion (~20 min) the reaction mixture was washed twice with an equal volume of de-ionized water, then ethylbenzene (2.1 mL/g 32) was added. The solution was concentrated to 65.2 g, reducing the dichloromethane in the solution to 0.17%, and stirred on an ice bath to crystallize the product. The product 34 was isolated by filtration. Yield: 44%.

Example 9

Triethylene Glycol Tail

See FIG. 2I

Preparation of trityl piperazine phenyl carbamate 35: To a cooled suspension of compound 11 in dichloromethane (6 mL/g 11) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 35 was isolated by crystallization from acetonitrile. Yield=80%

Preparation of carbamate alcohol 36: Sodium hydride (1.2 eq) was suspended in 1-methyl-2-pyrrolidinone (32 mL/g sodium hydride). To this suspension were added triethylene glycol (10.0 eq) and compound 35 (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 36 was isolated by crystallization from dichloromethane/methyl tert-butyl ether/heptane. Yield=90%.

Preparation of Tail acid 37: To a solution of compound 36 in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous $NaHCO_3$. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 37 was used without isolation in the preparation of compound 38.

Preparation of 38: To the solution of compound 37 was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts. Yield=70% of 38 from compound 36. Introduction of the activated "Tail" onto the disulfide anchor-resin was performed in NMP by the procedure used for incorporation of the subunits during solid phase synthesis.

Example 10

Preparation of the Solid Support for Synthesis of Morpholino Oligomers

FIG. 2J

Example 10a

Preparation of Aminomethylpolystyrene-disulfide resin

This procedure was performed in a silanized, jacketed peptide vessel (custom made by ChemGlass, NJ, USA) with a coarse porosity (40-60 µm) glass frit, overhead stirrer, and 3-way Teflon stopcock to allow $N_2$ to bubble up through the frit or a vacuum extraction. Temperature control was achieved in the reaction vessel by a circulating water bath.

The resin treatment/wash steps in the following procedure consist of two basic operations: resin fluidization and solvent/solution extraction. For resin fluidization, the stopcock was positioned to allow $N_2$ flow up through the frit and the specified resin treatment/wash was added to the reactor and allowed to permeate and completely wet the resin. Mixing was then started and the resin slurry mixed for the specified time. For solvent/solution extraction, mixing and $N_2$ flow were stopped and the vacuum pump was started and then the stopcock was positioned to allow evacuation of resin treatment/wash to waste. All resin treatment/wash volumes were 15 mL/g of resin unless noted otherwise.

To aminomethylpolystyrene resin (100-200 mesh; ~1.0 mmol/g $N_2$ substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was fluidized with a solution of disulfide anchor 34 in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 39 was dried under a $N_2$ stream for 1-3 hr and then under vacuum to constant weight (±2%). Yield: 110-150% of the original resin weight.

Example 10b

Determination of the Loading of Aminomethylpolystyrene-Disulfide Resin

The loading of the resin (number of potentially available reactive sites) is determined by a spectrometric assay for the number of triphenylmethyl (trityl) groups per gram of resin. A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 µL) is transferred to a 10 mL volumetric flask and the volume brought up to 10 mL with methanesulfonic acid.

The trityl cation content in the final solution is measured by UV absorbance at 431.7 nm and the resin loading calculated in trityl groups per gram resin (µmol/g) using the appropriate volumes, dilutions, extinction coefficient ($\epsilon$: 41 µmol$^{-1}$cm$^{-1}$) and resin weight. The assay is performed in triplicate and an average loading calculated.

The resin loading procedure in this example will provide resin with a loading of approximately 500 µmol/g. A loading of 300-400 in µmol/g was obtained if the disulfide anchor incorporation step is performed for 24 hr at room temperature.

Example 10c

Tail Loading

Using the same setup and volumes as for the preparation of aminomethylpolystyrene-disulfide resin, the Tail can be introduced into the molecule. For the coupling step, a solution of 38 (0.2 M) in NMP containing 4-ethylmorpholine (NEM, 0.4 M) was used instead of the disulfide anchor solution. After 2 hr at 45° C., the resin 39 was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 40 was filtered and dried under high vacuum. The loading for resin 40 is defined to be the loading of the original aminomethylpolystyrene-disulfide resin 39 used in the Tail loading.

Example 11

Preparation of Morpholino Oligomers on an Automated Synthesizer

Example 11a

Solid Phase Synthesis

Morpholino Oligomers were prepared on a Gilson AMS-422 Automated Peptide Synthesizer in 2 mL Gilson polypropylene reaction columns (Part # 3980270). An aluminum block with channels for water flow was placed around the columns as they sat on the synthesizer. The AMS-422 will alternatively add reagent/wash solutions, hold for a specified time, and evacuate the columns using vacuum.

For oligomers in the range up to about 25 subunits in length, aminomethylpolystyrene-disulfide resin with loading near 500 µmol/g of resin is preferred. For larger oligomers, aminomethylpolystyrene-disulfide resin with loading of 300-400 µmol/g of resin is preferred. If a molecule with 5'-Tail is desired, resin that has been loaded with Tail is chosen with the same loading guidelines.

The following reagent solutions were prepared:
Detritylation Solution: 10% Cyanoacetic Acid (w/v) in 4:1 dichloromethane/acetonitrile; Neutralization Solution: 5% Diisopropylethylamine in 3:1 dichloromethane/isopropanol; Coupling Solution: 0.18 M (or 0.24 M for oligomers having grown longer than 20 subunits) activated Morpholino Subunit of the desired base and linkage type and 0.4 M N-ethylmorpholine, in 1,3-dimethylimidazolidinone. Dichloromethane (DCM) was used as a transitional wash separating the different reagent solution washes.

On the synthesizer, with the block set to 42° C., to each column containing 30 mg of aminomethylpolystyrene-disulfide resin (or Tail resin) was added 2 mL of 1-methyl-2-pyrrolidinone and allowed to sit at room temperature for 30 min. After washing with 2 times 2 mL of dichloromethane, the following synthesis cycle was employed:

| Step | Volume | Delivery | Hold time |
|---|---|---|---|
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| DCM | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| Coupling | 350 uL-500 uL | Syringe | 40 minutes |
| DCM | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| DCM | 1.5 mL | Manifold | 30 seconds |
| DCM | 1.5 mL | Manifold | 30 seconds |

The sequences of the individual oligomers were programmed into the synthesizer so that each column receives the proper coupling solution (A, C, G, T, I) in the proper sequence. When the oligomer in a column had completed incorporation of its final subunit, the column was removed from the block and a final cycle performed manually with a coupling solution comprised of 4-methoxytriphenylmethyl chloride (0.32 M in DMI) containing 0.89 M 4-ethylmorpholine.

Example 11b

Cleavage from the Resin and Removal of Bases and Backbone Protecting Groups

After methoxytritylation, the resin was washed 8 times with 2 mL 1-methyl-2-pyrrolidinone. One mL of a cleavage solution consisting of 0.1 M 1,4-dithiothreitol (DTT) and 0.73 M triethylamine in 1-methyl-2-pyrrolidinone was added, the column capped, and allowed to sit at room temperature for 30 min. After that time, the solution was drained into a 12 mL Wheaton vial. The greatly shrunken resin was washed twice with 300 μL of cleavage solution. To the solution was added 4.0 mL conc aqueous ammonia (stored at −20° C.), the vial capped tightly (with Teflon lined screw cap), and the mixture swirled to mix the solution. The vial was placed in a 45° C. oven for 16-24 hr to effect cleavage of base and backbone protecting groups.

Example 11c

Initial Oligomer Isolation

The vialed ammonolysis solution was removed from the oven and allowed to cool to room temperature. The solution was diluted with 20 mL of 0.28% aqueous ammonia and passed through a 2.5×10 cm column containing Macroprep HQ resin (BioRad). A salt gradient (A: 0.28% ammonia with B: 1 M sodium chloride in 0.28% ammonia; 0-100% B in 60 min) was used to elute the methoxytrityl containing peak. The combined fractions were pooled and further processed depending on the desired product.

Example 11d

Demethoxytritylation of Morpholino Oligomers

Methoxytrityl Off Oligomers

The pooled fractions from the Macroprep purification were treated with 1 M $H_3PO_4$ to lower the pH to 2.5. After initial mixing, the samples sat at room temperature for 4 min, at which time they are neutralized to pH 10-11 with 2.8% ammonia/water. The products were purified by solid phase extraction (SPE).

Amberchrome CG-300M (Rohm and Haas; Philadelphia, Pa.) (3 mL) is packed into 20 mL fritted columns (BioRad Econo-Pac Chromatography Columns (732-1011)) and the resin rinsed with 3 mL of the following: 0.28% $NH_4OH$/80% acetonitrile; 0.5M NaOH/20% ethanol; water; 50 mM $H_3PO_4$/80% acetonitrile; water; 0.5 NaOH/20% ethanol; water; 0.28% $NH_4OH$.

The solution from the demethoxytritylation was loaded onto the column and the resin rinsed three times with 3-6 mL 0.28% aqueous ammonia. A Wheaton vial (12 mL) was placed under the column and the product eluted by two washes with 2 mL of 45% acetonitrile in 0.28% aqueous ammonia. The solutions were frozen in dry ice and the vials placed in a freeze dryer to produce a fluffy white powder. The samples were dissolved in water, filtered through a 0.22 micron filter (Pall Life Sciences, Acrodisc 25 mm syringe filter, with a 0.2 micron HT Tuffryn membrane) using a syringe and the Optical Density (OD) was measured on a UV spectrophotometer to determine the OD units of oligomer present, as well as dispense sample for analysis. The solutions were then placed back in Wheaton vials for lyophilization.

Example 11e

Analysis of Morpholino Oligomers

MALDI-TOF mass spectrometry was used to determine the composition of fractions in purifications as well as provide evidence for identity (molecular weight) of the oligomers. Samples were run following dilution with solution of 3,5-dimethoxy-4-hydroxycinnamic acid (sinapinic acid), 3,4,5-trihydroxyacetophenone (THAP) or alpha-cyano-4-hydroxycinnamic acid (HCCA) as matrices.

Cation exchange (SCX) HPLC was performed using a Dionex ProPac SCX-10, 4×250 mm column (Dionex Corporation; Sunnyvale, Calif.) using 25 mM pH=5 sodium acetate 25% acetonitrile (Buffer A) and 25 mM pH=5 sodium acetate 25% acetonitrile 1.5 M potassium chloride (buffer B) (Gradient 10-100% B in 15 min) or 25 mM $KH_2PO_4$ 25% acetonitrile at pH=3.5 (buffer A) and 25 mM $KH_2PO_4$ 25% acetonitrile at pH=3.5 with 1.5 M potassium chloride (buffer B) (Gradient 0-35% B in 15 min). The former system was used for positively charged oligomers that do not have a peptide attached, while the latter was used for peptide conjugates.

Example 11f

Purification of Morpholino Oligomers by Cation Exchange Chromatography

The sample is dissolved in 20 mM sodium acetate, pH=4.5 (buffer A) and applied to a column of Source 30 cation exchange resin (GE Healthcare) and eluted with a gradient of 0.5 M sodium chloride in 20 mM sodium acetate and 40% acetonitrile, pH=4.5 (buffer B). The pooled fractions containing product are neutralized with conc aqueous ammonia and applied to an Amberchrome SPE column. The product is eluted, frozen, and lyophilized as above.

The following oligomers exemplify this method:

5'-(EG3)-G+TGC+TCA+TGG+TGCACGG+TC-3'-(H) (SEQ ID NO.:107), calculated $[M+H]^+$=6860.9 daltons, found $[M+H]^+$=6861.7 daltons, useful for HCV 5'-(EG3)-GCC+ATGGT+TTT+TTC+TC+AGG-3'-(H) (SEQ ID NO.:108), calculated $[M+H]^+$=6825.9 daltons, found $[M+H]^+$=6827.1 daltons, useful for Ebola 5'-(EG3)-+TGGGT+ATG+TTGT+AGCC+AT-3'-(H) (SEQ ID NO.:109), calculated $[M+H]^+$=7245.2 daltons, found $[M+H]^+$=7246.8 daltons, useful for Ebola 5'-(EG3)-CC+TGCCC+TTTGT+TCT+AGT+TG-3'-(H) (SEQ ID NO.:110), calculated $[M+H]^+$=7092.2 daltons, found $[M+H]^+$=7093.8 daltons, useful for Ebola.

Example 11g

3-'-Methoxytrityl and 3'-Trityl Morpholino Oligomers

The Macroprep purified oligomers were directly applied to the solid phase extraction columns, and the 3'-methoxytritylated oligomers were isolated and quantified in the same manner as the demethoxytritylated species.

Example 12

Synthesis of N2,06-Protected Morpholino G (DPG) for Large Scale Oligomer Synthesis

FIG. 2K

Preparation of 41: To a cooled solution of 1c and imidazole (1.3 eq) in dichloromethane (8 mL/g 1) was added a solution of tert-butyldimethylchlorosilane (1.2 eq) in dichloromethane. After addition, the solution was warmed to 20° C. Upon reaction completion (1-3 hours), this solution was washed successively with 1 M citrate buffer (adjusted to pH 3 with NaOH) and water. The resulting organic solution was distilled to azeotropically remove water and used directly in the next step.

Preparation of 42: To a 0° C. cooled solution of 41 in dichloromethane were added successively triethylamine (1.2 eq), 4-dimethylaminopyridine (0.1 eq), and triisopropylbenzenesulfonyl chloride (1.1 eq). The solution was warmed to 20° C. Upon reaction completion (3-9 hours), the solution was washed successively with 1 M $KH_2PO_4$ and water. The resulting organic solution was distilled to azeotropically remove water and used directly in the preparation of compound 44.

Preparation of 43: To a solution of 4-hydroxybenzaldehyde (1.0 eq) and N-methylimidazole (0.2 eq) in toluene was added a solution of $KHCO_3$ (2.0 eq) in water. To the resulting two-phase mixture was added trimethylacetyl chloride (1.4 eq). Upon reaction completion (1-2 hours), methanol (1.0 eq) was added, and the mixture was stirred for 1 hour. After separation of layers, the organic layer was washed successively with 1 M $KH_2PO_4$ and water. The resulting organic solution was distilled to azeotropically remove water and diluted with THF. To this solution was added 5% Pd/C catalyst (0.004 eq, Johnson Matthey, West Deptford, N.J., USA), and the mixture was hydrogenated under 5-30 psi $H_2$. Upon reaction completion (4-8 hours), the mixture was filtered through a pad of Celite and washed with pH 6.5 phosphate buffer. The product was crystallized from toluene/heptane. Yield=80%.

Preparation of 44: To a cooled solution of 3 in dichloromethane was added N-methylpyrrolidine (2.0 eq). After 10 minutes, 3a (1.2 eq) was added, followed by DBU (1.2 eq). After reagent addition, the solution was warmed to 20° C. Upon reaction completion (1-9 hours), the solution was washed successively with 1 M $KH_2PO_4$ and water. The resulting organic solution was distilled to azeotropically remove water and used directly in the next step.

Preparation of 45: To the solution of 44 in dichloromethane was added triethylamine trihydrofluoride (2.0 eq). Upon reaction completion (4-20 hours), the solution was washed successively with sodium bicarbonate solution, pH 6.5 phosphate buffer, and water. The resulting solution was distilled to remove dichloromethane, and the product was crystallized from THF/water. Yield=70% from 1c.

Preparation of 46: Compound 45 was dissolved in dichloromethane (6 mL/g 45) and cooled to <5° C. To this solution were added 2,6-lutidine (1.6 eq), N-methylimidazole (0.3 eq), and N,N-dimethylphosphoramidodichloridate (1.6 eq). The solution was warmed to 20° C. Upon reaction completion (6-12 hours), this mixture was washed with a pH 3 citrate buffer. The crude product was isolated by precipitation/reslurry. The doubly protected (DPG) product 46 was purified by silica gel chromatography (gradient of ethyl acetate/heptane) and isolated by precipitation into heptane. Yield=40-60%.

Example 13

Large Scale Synthesis of Morpholino Oligomers

The reactor design for the loading of anchor and Tail on aminomethylpolystyrene resin is used for larger scale synthesis of Morpholino Oligomers. Resin loading guidelines are the same as for the smaller scale synthesis.

Example 13a

Solid Phase Synthesis

Protected oligomers were prepared manually by solid phase oligomer synthesis on aminomethylpolystyrene-disulfide resin (~500 µmol/g loading) at 10 g scale (starting resin weight). Solutions used were as follows: detritylation solution: 2% 4-cyanopyridinium trifluoroacetate (CYTFA) (w/v) in 20% trifluoroethanol/dichloromethane with 1% ethanol; neutralization solution: 5% diisopropylethylamine in 25% isopropanol/dichloromethane; coupling solution: 0.165 M (for 46 (DPG) and 5d or other T subunits) or 0.18 M (for 5a and 5b or other A/C subunits) activated Morpholino Subunit and 0.4 M N-ethylmorpholine in 1,3-dimethylimidazolidinone (DMI).

After transfer of the resin to the synthesis reactor and prior to initiating synthesis cycles, 1-methyl-2-pyrrolidinone (NMP, 20 mL/g resin) was added and allowed to sit for 1-2 hrs. After washing 2 times with dichloromethane (10 mL/g resin), the following synthesis cycle was used with addition of the appropriate coupling solution of activated Morpholino Subunit of the desired base and desired linkage type at each cycle to give the proper sequence.

| Step | Volume (mL/g of starting resin)* | Time (min) |
|---|---|---|
| DCM | 10-30 | 1-2 |
| DCM | 10-30 | 1-2 |
| Detritylation A | 10-30 | 2-3 |
| Detritylation A | 10-30 | 2-3 |
| Detritylation A | 10-30 | 2-3 |
| Detritylation A | 10-30 | 2-3 |
| Detritylation A | 10-30 | 2-3 |
| Neutralization A | 10-30 | 3-4 |
| Neutralization A | 10-30 | 3-4 |
| Neutralization A | 10-30 | 3-4 |
| Neutralization A | 10-30 | 3-4 |
| DCM | 10-30 | 1-2 |
| DCM | 10-30 | 1-2 |
| Coupling | 7-12** | 90 |
| Neutralization A | 10-30 | 1-2 |
| Neutralization A | 10-30 | 1-2 |
| Neutralization A | 10-30 | 1-2 |
| Neutralization A | 10-30 | 1-2 |
| DCM | 10-30 | 1-2 |

*Wash volumes are incremented to account for resin swelling; volume is 10 mL/g of actual resin volume at each cycle
**Coupling volumes are sufficient to maintain good mixing and are incremented to account for resin swelling After incorporation of the final subunit, a final cycle (methoxytritylation) was performed with 0.32 M 4-methoxytriphenylmethyl chloride and 0.4 M N-ethylmorpholine in DMI. After methoxytritylation, the resin was washed 8 times with NMP and then treated with cleavage solution consisting of 0.1 M 1,4-dithiothreitol (DTT) and 0.73 M triethylamine in NMP (27 mL/g starting resin) for 30 min. After collection of the protected oligomer solution, the resin (significantly reduced in volume) was washed with two additional portions of cleavage solution (13 mL/g starting resin for 15 min each) and the washes were combined with the bulk solution. To the protected oligomer solution in an appropriately sized pressure bottle with Teflon plug (Ace Glass, NJ, USA) was added concentrated aqueous ammonia (106 mL/g starting resin, previously cooled to −20° C.), the bottle sealed, and the contents mixed by swirling. The bottle was placed in a 45° C. oven for 16-20 hr to remove base and backbone protecting groups.

Following ammonolysis, the crude oligomer solution is cooled to room temperature and then diafiltered against 0.28% aqueous ammonia using a PLBC 3 kd Regenerated Cellulose membrane (Millipore) to remove solvents and small molecules prior to ion exchange chromatography.

Example 13b

Purification of Morpholino Oligomers by Anion Exchange Chromatography

The crude oligomer solution obtained from diafiltration is adjusted to pH 11-11.5 and loaded onto a column of ToyoPearl Super-Q 650S anion exchange resin (Tosoh Bioscience. The methoxytritylated oligomer was eluted with a gradient of 5-35% B over 17 column volume (Buffer A: 10 mM sodium hydroxide; Buffer B: 1 M sodium chloride in 10 mM sodium hydroxide) and fractions of acceptable purity (anion exchange HPLC and mass spec) pooled.

Example 13c

Demethoxytritylation of Morpholino Oligomers

To the pooled fractions from anion exchange chromatography was added acetonitrile (10% by volume) followed by 2 M $H_3PO_4$ to adjust the pH to 3. The solution was mixed for 45 min and then neutralized with concentrated aqueous ammonia to pH 7. The oligomer solution was diafiltered against 20 mM sodium acetate using a PLBC 3 kd Regenerated Cellulose membrane (Millipore) to exchange buffers prior to cation exchange chromatography.

Example 13d

Purification of Morpholino Oligomers by Cation Exchange Chromatography

The oligomer solution was adjusted to pH 4.5 with acetic acid and loaded onto a column of Source 30S cation exchange resin (GE Healthcare). The oligomer was eluted with a gradient of 0-35% B over 17 column volumes (Buffer A: 20 mM sodium acetate, 25% acetonitrile, pH 4.5; Buffer B: 0.5 M sodium chloride, 20 mM sodium acetate, 25% acetonitrile, pH 4.5) and fractions of acceptable purity (cation exchange HPLC and mass spec) pooled.

Example 13e

Isolation of Morpholino Oligomers

The purified oligomer solution was diafiltered against 0.028% aqueous ammonia using a PLBC 3 kd Regenerated Cellulose membrane (Millipore) to remove salt and generate the oligomer free base. The desalted oligomer solution was then frozen and lyophilized to give the oligomer as a white fluffy powder (~12% water content). By this method compounds useful in Ebola treatment were prepared:

5'-(EG3)-GCC+ATGGT+TTT+TTC+TC+AGG-3'-(H) (SEQ ID NO.:108), 8.4 g
5'-(EG3)-CC+TGCCC+TTTGT+TCT+AGT+TG-3'-(H) (SEQ ID NO.:110), 10.0 g

Identical to the compounds made by small scale.

Example 13f

Analysis of Morpholino Oligomers by Anion Exchange HPLC

Anion exchange (SAX) HPLC was performed using a Dionex DNAPac, 4×250 mm column (Dionex Corporation; Sunnyvale, Calif.) using 20 mM sodium chloride, 10 mmol sodium hydroxide (Buffer A) and 1 M sodium chloride, 10 mmol sodium hydroxide (buffer B), (Gradient 10-53% B in 20 min).

Example 14

Introduction of a Guanidinium group into a Morpholino Oligomer

Example 14a

By Direct Guanylation of Amines

10 μmol of a Morpholino Oligomer, the backbone of which contained three piperazine secondary amines, were dissolved in 0.5 M Na$_2$CO$_3$ at 75 mg/mL. 700 µmol of 1-H-pyrazole-1-carboxamidine HCl were added to the Morpholino Oligomer solution and the reaction stirred at room temperature. After three hours had elapsed, the reaction was diluted with water and purified by solid phase extraction (SPE) using an Amberchrom CG300M (Rohm and Haas; Philadelphia, Pa.) column. The SPE purification entailed loading the sample onto the column at 20 mg/mL, washing the column with 4 column volumes of 1 M NaCl and then 3 column volumes of water. The product was eluted by washing the column with 3 column volumes of acetonitrile/water (1:1 v/v). The product, as the HCl salt, was then lyophilized.

Strong cation exchange (SCX) purification at pH=9 of morpholino oligomers containing guanidine backbone moieties may be achieved when the oligomer contains at least three guanidine groups on the backbone and/or termini. Prior to lyophilization, the desalted solution from above was purified by SCX at pH 9 to separate the guanidine-modified product from any remaining underivatized piperazine precursor. The liquid chromatography column had dimensions of 10×62 mm (Bio-Chem Valve/Omnifit, Cambridge, United Kingdom) and contained Source 15S strong cation exchange media (GE Healthcare Bio-Sciences Corp., Piscataway, N.J.). The mobile phase compositions were A) 25 mM Tris HCl, 25% acetonitrile (v/v); pH 9.0 and B) 1.0 M sodium chloride, 25 mM Tris HCl, 25% acetonitrile (v/v); pH 9.0. A linear velocity of 342 cm/hr was used. After equilibration of the column with four column volumes of mobile phase A, the oligomer sample was loaded in mobile phase A at a concentration of approximately 5 mg/mL. The column was then washed for two minutes with mobile phase A, after which fraction collection was initiated concurrently with a linear gradient of 0-20% mobile phase B over twenty-two minutes. Fractions were analyzed individually by MALDI-TOF MS. Selected fractions were pooled and desalted by solid phase extraction. The fraction pool was diluted 5-fold with water and loaded onto an Amberchrom CG300M column. The SPE desalt entailed loading the sample onto the column at 20 mg/mL and washing the column with 3 column volumes of water. The product was then eluted by washing the column with 3 column volumes of acetonitrile/water (1:1 v/v). The product was lyophilized and analyzed by MALDI-TOF MS and SCX HPLC.

The following oligomers exemplify this method:
5'-(EG3)-CTGGG+ATG+AG+ATCC+ATC+ACT-3'-(H) (SEQ ID NO.:111) was prepared using resin with Tail. A sample (1000 OD) was converted by the methods above into: 5'-(EG3) CTGGG(Gupip)ATG(Gupip)AG (Gupip) ATCC(Gupip)ATC(Gupip)ACT-3'-(Gu) (SEQ ID NO.:111) calculated [M+H]$^+$=7421.5 daltons. The crude product (907 OD) recovered after SPE, found [M+H]$^+$=7422.6 daltons, was purified on SCX ion exchange at pH=9 to provide 378 OD product, found [M+H]$^+$=7420.9.

Example 14b

Introduction of Guanidinium Groups by Reaction with Guanidino Amino Acid Trifluoroacetate Salts Preparation of Guanidino Acid Trifluoroacetate Salts.

The guanidino acid was dissolved in trifluoroacetic acid at a concentration of 330 mg/mL with gentle heating and stirring. Once fully dissolved, the solution was added dropwise to a tenfold volumetric excess of diethyl ether to precipitate the trifluoroacetate salt of the guanidino acid. The suspension was centrifuged, the supernatant decanted, and the solid triturated in a fresh portion of diethyl ether. The suspension was again centrifuged, the supernatant decanted, and the solid dried under vacuum.

Conjugation of Guanidino Acids (General) to Amines of a Morpholino Oligomer.

The morpholino oligomer, containing free amino groups on the backbone and/or termini, was dissolved in DMSO at 75 mg/mL. Separately, an activated guanidino acid solution was prepared by dissolving the trifluoroacetate or hydrochloride salt of the guanidino acid (2 equivalents with respect to Morpholino Oligomer amines) and HBTU (1.95 equivalents with respect amines) in NMP at 100 mg/mL (with respect to guanidino acid). DIEA (3 equivalents with respect to guanidino acid) was then added to the guanidino acid solution. The activated guanidino acid solution was mixed briefly and immediately added to the Morpholino Oligomer solution. After three hours of stirring at room temperature, the reaction was diluted 2.33-fold with cold concentrated ammonium hydroxide. As required, TFE was added slowly with gentle heating and mixing to redissolve the precipitated solid. The reaction was then heated at 45° C. in a sealed vessel for 18 hours, after which it was diluted 15-fold with water and purified by SPE using an Amberchrom CG300M (Rohm and Haas; Philadelphia, Pa.) column. The SPE purification entailed loading the sample onto the column at 20 mg/mL, washing the column with 4 column volumes of 1 M NaCl and then 3 column volumes of water. The product was eluted by washing the column with 3 column volumes of acetonitrile/water (1:1 v/v). The conjugate was lyophilized and analyzed by MALDI-TOF MS and SCX HPLC.

The following oligomers exemplify this method:
5'-(H)-C+TTCGA+TAG+TG-3'-(H) (SEQ ID NO.:66) was prepared from using resin with no Tail. A sample (970 OD) was converted with 4-guanidinobutanoic acid by the methods above into: 5'-(GuBu)-C(GuBupip)TTCGA(GuBupip)TAG(GuBupip)TG-3'-(GuBu), calculated [M+H]'= 4541.2 daltons. The crude product (820 OD) recovered after SPE, found [M+H]'=4541.9 daltons, was purified on SCX ion exchange at pH=9 to provide 356 OD product, found [M+H]'= 4542.1.

Conjugation of 6-Guanidinohexanoic acid to Secondary Amines of a Morpholino Oligomer.

6-Guanidinohexanoic acid was obtained from AlzChem; Trostberg, Germany. The Morpholino Oligomer (20 µmol), an 18-mer with eight secondary amines incorporated into the backbone (160 µmol of amine groups), was dissolved in dimethylsulfoxide (DMSO) at 75 mg/mL. Separately, an activated 6-guanidinohexanoic acid solution was prepared by dissolving 320 µmol (2 molar equivalents with respect to amines) of the trifluoroacetate salt of 6-Guanidinohexanoic acid and 312 µmol of 2-(1-H-benzotriazol-1-yl)-1,1,3,3-tetramethylaminium hexafluorophosphate (HBTU) in 920 µL of 1-methyl-2-pyrrolidinone (NMP) and adding 960 µmol of N,N-diisopropylethylamine (DIEA). Immediately after addition of DIEA, the activated guanidino-acid solution was added to the Morpholino Oligomer solution. After stirring under nitrogen at room temperature for three hours, 4 mL of concentrated ammonium hydroxide were added to the reaction. 7 mL of 2,2,2-trifluoroethanol (TFE) were added with gently heating and mixing to redissolve the precipitated solid and the solution heated at 45° C. for 18 hours. The solution was then diluted to 200 mL with water and purified by solid phase extraction (SPE) using an Amberchrom CG300M column as detailed above. The conjugate was lyophilized and analyzed by MALDI-TOF MS and SCX HPLC.

The following oligomers exemplify this method:

5'-(H)-C+TTCGA+TAG+TG-3'-(H) (SEQ ID NO.:66) was prepared using resin with no Tail. A sample (635 OD) was converted by the methods above into: 5'-(GuAhx)-C(GuX) TTCGA(GuX)TAG(GuX)TG-3'-(GuAhx) (SEQ ID NO.:66), calculated [M+H]$^+$=4681.4 daltons. The crude product (563 OD) recovered after SPE, found [M+H]$^+$=4681.2 daltons, was purified on SCX ion exchange at pH=6.5 to provide 427 OD product of 93.3% purity by SCX HPLC, found [M+H]$^+$=4682.4.

5'-(EG3)-CTGGG+ATG+AG+ATCC+ATC+ACT-3'-(H) (SEQ ID NO.:111) was prepared using resin with Tail. A sample (1500 OD) was converted by the methods above into: 5'-(EG3)-CTGGG(GuX)ATG(GuX)AG(GuX)ATCC (GuX) ATC(GuX)ACT-3'-(GuAhx) (SEQ ID NO.:111), calculated [M+H]$^+$=8100.5 daltons. The crude product (1486 OD) recovered after SPE, found [M+H]$^+$=8100.4 daltons, was purified on SCX ion exchange at pH=9 to provide 700 OD product, found [M+H]$^+$=8100.6.

This method was also used to add peptide acids such as AcRAhxRAhxB (written more expansively as AcNH-RAhxRAhxB-OH in FIG. 2O) to the backbone amines.

Example 14c

By Conjugation of Aminoalkanoic Acids to Amines of a Morpholino Oligomer Followed by Guanylation The Morpholino Oligomer, containing free amino groups on the backbone and/or termini, was dissolved in DMSO at 75 mg/mL. Separately, an activated Fmoc-aminoalkanoic acid solution was prepared by dissolving the Fmoc-protected amino acid (2 equivalents with respect to Morpholino Oligomer amines) and HBTU (1.95 equivalents with respect amines) in NMP at 100 mg/mL (with respect to amino acid). DIEA (3 equivalents with respect to amino acid) was then added to the amino acid solution. The activated amino acid solution was mixed briefly and immediately added to the Morpholino Oligomer solution. After three hours of stirring at room temperature, the reaction was diluted 2.33-fold with cold concentrated ammonium hydroxide. The reaction was then heated at 45° C. in a sealed vessel for 18 hours, after which it was diluted 15-fold with water and purified by SPE using an Amberchrom CG300M (Rohm and Haas; Philadelphia, Pa.) column. The SPE purification entailed loading the sample onto the column at 20 mg/mL, washing the column with 4 column volumes of 1 M NaCl and then 3 column volumes of water. The product was eluted by washing the column with 3 column volumes of acetonitrile/water (1:1 v/v). The conjugate was lyophilized and analyzed by MALDI-TOF MS and SCX HPLC. The product may be guanylated and purified as per the previous examples.

The following oligomers exemplify this method:

5'-(EG3)-CTGGG+ATG+AG+ATCC+ATC+ACT-3'-(H) (SEQ ID NO.:111) was prepared using resin with Tail. A sample (2000 OD) was converted by the methods above into: 5'-(EG3)-CTGGG(Ahxpip)ATG(Ahxpip)AG(Ahxpip) ATCC (G)ATC(Ahxpip)ACT-3'-(Ahx) (SEQ ID NO.:111), calculated [M+H]$^+$=7848.3 daltons. The crude product (1672 OD) recovered after SPE, found [M+H]$^+$=7847.7 daltons. A portion of this material (800 OD) was further converted by guanylation into 5'-(EG3)-CTGGG(GuX) ATG(GuX)AG (GuX)ATCC(GuX) ATC(GuX)ACT-3'-(GuAhx) (SEQ ID NO.:111), calculated [M+H]$^+$=8100.5 daltons. The crude product recovered after SPE, found [M+H]$^+$=8101.4 daltons, as purified by SCX chromatography to give 320 OD of final product.

Example 15

Introduction of Arginine Rich Peptides into a Morpholino Oligomer

The morpholino oligomer, containing free amino groups on the backbone and/or termini, was dissolved in DMSO at 75 mg/mL. Separately, an activated peptide solution was prepared, the peptide being 1-25 amino acid residues in length, containing an N-terminal blocking group, preferably acetyl, and comprised of amino acids with guanidinium, hydrocarbon, or other non-nucleophilic side chains. The peptide (2 equivalents with respect to morpholino oligomer amines) and HBTU (1.95 equivalents with respect to amine groups) were dissolved in NMP at 100 mg/mL (with respect to peptide). DIEA (2 equivalents with respect to peptide) was then added to the peptide solution. The activated peptide solution was mixed briefly and immediately added to the morpholino oligomer solution. After three hours of stirring at room temperature, the reaction was diluted 2.33-fold with cold concentrated ammonium hydroxide. As required, TFE was added slowly with gentle heating and mixing to redissolve the precipitated solid. The reaction was then heated at 45° C. in a sealed vessel for 18 hours, after which it was diluted 15-fold with water and purified by SPE using an Amberchrom CG300M (Rohm and Haas; Philadelphia, Pa.) column. The SPE purification entailed loading the sample onto the column at 20 mg/mL, washing the column with 4 column volumes of 1 M NaCl and then 3 column volumes of water. The product was eluted by washing the column with 3 column volumes of acetonitrile/water (1:1 v/v). The conjugate was lyophilized and analyzed by MALDI-TOF MS and SCX HPLC. The product may be purified as per the pervious examples.

Example 16

Preparation of Morpholino Oligomers Having an Arginine Rich Peptide and Backbone Guanidinium Groups Morpholino oligomers with backbone guanidinium groups, as prepared in Example 14, were reacted with arginine rich peptides as in Example 15. The products were purified on Source 15S SCX cation exchange resin as described in Example 13.

Example 17

Preparation of Morpholino Oligomers Having an Arginine Rich Peptide and Backbone Amine Groups Example 17a Protection of Morpholino Oligomer Secondary Amines as Trifluoroacetamides 41 mg of the Morpholino oligomer, an 11-mer with three backbone secondary amines and 3'-trityl or methoxytrityl, were dissolved in 0.500 mL of dimethylsulfoxide (DMSO). To the oligomer solution were added 8.2 µL (5 eq) N,N-diisopropylethylamine (DIEA) followed by 44 µL (5 eq.) of a 250 mg/mL solution of 4-nitrophenyl trifluoroacetate in N-methylpyrrolidinone (NMP). The additions of DIEA and 4-nitrophenyl trifluoroacetate were repeated four more times at 90 min intervals and the reaction then stirred for 15 hr at room temperature. The 3'-trityl or methoxytrityl group was then removed by adding 3.76 mL (20 eq.) of a 50 mM solution of 4-cyanopyridinium trifluoroacetate in 2,2,2-trifluoroethanol (TFE) and stirring for 40 min. The reaction was then diluted to 40 mL with water and the pH adjusted to 7.5 by adding 0.5 M sodium phosphate buffer, pH 7.5, dropwise. The product was isolated by solid phase extraction using a 2 mL Amberchrom CG300M column. After loading the crude reaction mixture onto the column, the column was rinsed with two column volumes of water, four column volumes of 15% acetonitrile/water (v/v), and four column volumes of 20% acetonitrile/water (v/v). The backbone-protected product with free 3'-morpholine amine was then eluted with three column volumes of 1:1 acetonitrile/water (v/v) and lyophilized.

Example 17b

Conjugation of Arginine Rich Peptides to Morpholino Oligomer Followed by Unmasking of Oligomer Backbone Amines An activated peptide solution was prepared by dissolving the peptide-acid (22.6 µmol) and HBTU (22.3 µmol) in 300 µl NMP and adding DIEA (40.8 µmol). Immediately after addition of DIEA, the peptide solution was added to a solution of the backbone-protected Morpholino oligomer with free 3'-morpholino amine in 0.550 mL DMSO. After 180 minutes at room temperature, 2 mL of concentrated ammonium hydroxide were added to the reaction. The resulting precipitate was redissolved with the addition of 4 mL TFE and gentle heating and mixing. The reaction was placed in a 45° C. oven for 15 hours. Water was then added, diluting the reaction to 40 mL. Then the solution was neutralized by adding 2 M phosphoric acid dropwise with stirring. The product was isolated by solid phase extraction using a 2 mL Amberchrom CG300M column. After loading the crude reaction mixture onto the column, the column was rinsed with four column volumes of water. The product was then eluted with three column volumes of 1:1 acetonitrile/water (v/v) and lyophilized.

The following oligomers exemplify this method:

5'-(EG3)-G+TGC+TCA+TGG+TGCACGG+TC-3'-(SEQ ID NO.:107)-(Ac(RAhxR)$_4$AhxB-) (SEQ ID NO: 97), calculated [M+H]$^+$=8789.3 daltons, found [M+H]$^+$=8789.9 daltons, useful for Ebola 5'-(EG3)-C+TTCGA+TAG+TG-3'-(trityl) (SEQ ID NO.: 66) was prepared using resin with Tail. A sample (994 OD) was converted by the methods above into: 5'-(EG3)-C (TFApip)TTCGA(TFApip)TAG(TFApip)TG-3'-(H) (SEQ ID NO.:66), calculated [M+H]$^+$=4368.6 daltons. The crude product recovered after SPE, found [M+H]$^+$=4371.1 daltons. This sample was further converted by acylation with Ac(RAhxR)$_4$AhxB (SEQ ID NO.: 97) to give 5'-(EG3)-C+ TTCGA+TAG+TG-3'-(SEQ ID NO.:66) (Ac(RAhxR)$_4$ AhxB-) (SEQ ID NO.: 97), calculated [M+H]$^+$=6010.0 daltons. The crude product (770 OD) recovered after SPE, found [M+H]$^+$=6011.6 daltons. This was purified on SCX ion exchange at pH=6.5 to provide 478 OD product, found [M+H]$^+$=6010.7 daltons, with SCX HPLC purity of 84.7%.

Example 18

Reductive Methylation of Morpholino Oligomer Amines

A formaldehyde solution was prepared by dissolving 0.52 g paraformaldehyde in 17 mL of 200 mM pH 8.5 sodium borate buffer with heating and stirring. The solution was heated to a gentle boil, with a reflux condenser attached, for 1 hour. Heating was then ceased, the reaction mixture cooled to room temperature, and the solution continued to stir for the duration of the methylation reaction.

A 1 M solution of sodium borohydride was prepared by cooling 10 mL of 200 mM pH 8.5 sodium borate buffer on an ice bath and then dissolving 0.378 g of sodium borohydride in it. The solution was kept cold on ice for the duration of the methylation reaction.

33 mg (4.6 µmol) of a 20-mer Morpholino oligomer with five secondary amines incorporated into the backbone and a free morpholine secondary amine at the 3'-terminus was weighed into a glass vial. The oligomer was then dissolved in 1 mL of 200 mM pH 8.5 sodium borate buffer and cooled to 0° C. on an ice bath with stirring. 200 µL of the formaldehyde solution (~43 eq.) prepared above were added to the stirring Morpholino oligomer solution. Immediately after the formaldehyde addition, 40 µL of the 1 M sodium borohydride solution (8.7 eq.) were added. The formaldehyde and sodium borohydride additions were repeated five times at 30 min. intervals. After the final additions, the reaction was stirred for 30 min. and then 4 mg of sodium borohydride added. The reaction was then stirred for another 2 hours. Water was added to dilute the reaction to 5 mL and the pH adjusted to 6.5 by adding 1 M phosphoric acid dropwise.

The product was isolated by solid phase extraction using a 2 mL Amberchrom CG300M column. After loading the crude reaction mixture onto the column, the column was rinsed with four column volumes of water. The product was then eluted with three column volumes of 1:1 acetonitrile/water (v/v) and lyophilized.

The following oligomers exemplify this method:

5'-(EG3)-CTGGG+ATG+AG+ATCC+ATC+ACT-3'-(H) (SEQ ID NO.:111) was prepared using resin with Tail. A sample (885 OD) was converted by the methods above into:

5'-(EG3)-CTGGG(Mepip)ATG(Mepip)AG(Mepip) ATCC(Mepip)ATC(Mepip)ACT-3'-(Methyl) (SEQ ID NO.: 111) calculated [M+H]$^+$=7253.5 daltons. The crude product (625 OD) recovered after SPE, found [M+H]$^+$=7250.5 daltons.

Example 19

Peptide Synthesis and Conjugation to PMO

Peptide synthesis of RFF (CP04073, (RFF)$_3$AhxβAla), SEQ ID NO:79 and RTR (CP04074, RTRTRFLRRTAhx-βAla, SEQ ID NO:80) and conjugation to PMO were performed using the following techniques. All the peptides of the present invention can be synthesized and conjugated to PMO using these synthetic techniques.

Peptides were synthesized by Fmoc Solid Phase Peptide Synthesis, referred to herein as SPPS. A p-benzyloxybenzyl alcohol resin was used for synthesis of peptides (Novabiochem, San Diego, Calif.). A typical synthesis cycle began with N-terminal deprotection via 20% piperidine. Then, N-a-Fmoc-protected amino acids were coupled to the growing peptide chain by activation with 2-(1H-Benzotriazole-1-yl)-1,1,3,3-tetramethyluronium hexafluorophosphate (HBTU) in the presence of N,N-diisopropylethylamine (DIEA). Arginine side chains were protected with the 2,2,4,6,7-pentamethyldihydrobenzofuran-5-sulfonyl (Pbf) protecting group and the t-Butyl (tBu) group for tyrosine side chains. The cycle was repeated until all of the amino acids were added, in a carboxy-to-amino direction, in the desired sequence. Cleavage from the synthesis resin and side chain deprotection of the CP04073 peptide were carried out simultaneously by treating the peptidyl-resin with a solution of 5% $H_2O$ and 95% trifluoroacetic acid (TFA). For the CP04074 peptide residue, a cleavage cocktail of 81.5% TFA, 5% Thioanisole, 5% Phenol, 5% $H_2O$, 2.5% 1,2-ethanedithiol (EDT) and 1% triisopropyl silane (TIS) was used for simultaneous cleavage and side chain deprotection. Crude peptides were isolated by precipitation using a tenfold excess of diethyl ether. Strong cation exchange HPLC utilizing Source 15S resin (Amersham Biosciences, Piscataway, N.J.) was used for purification, followed by a reversed phase desalt employing Amberchrom 300M resin (Tosoh Bioscience, Montgomeryville, Pa.). Desalted peptides were lyophilized and analyzed for identity and purity by matrix assisted laser desorption ionization time of flight mass spectroscopy (MALDI-TOF'MS) and strong cation exchange high performance liquid chromatograph (SCX HPLC).

Attachment of the peptides at the 5' termini of the PMO was performed via an amide bond as follows. A C-terminally reactive peptide-benzotriazolyl ester was prepared by dissolving the peptide-acid (15 μmol), HBTU (14.25 μmol), and HOBt (15 μmol) in 200 μL NMP and adding DIEA (22.5 μmol). Immediately after addition of DIEA, the peptide solution was added to 1 mL of a 12 mM solution of 5'-piperazine-functionalized, 3'-acetyl-PMO in DMSO. After 180 minutes at 30° C., the reaction was diluted with a four-fold excess of water. The crude CP04074 conjugate was purified first through a CM-Sepharose weak cation exchange column (Sigma, St. Louis, Mo.) to remove unconjugated PMO, and then through a reversed phase column (Amberchrom 300M resin (Tosoh Bioscience, Montgomeryville, Pa.). The crude CP04073 conjugate was purified by resolving chromatography using strong cation exchange resin (Source 30S, Amersham Biosciences, Piscataway, N.J.) to remove unconjgated PMO and excess peptide. The SCX chromatography was followed by a reverse phase column (Amberchrom 300M resin (Tosoh Bioscience, Montgomeryville, Pa.). The conjugates were lyophilized and analyzed by MALDI-TOF MS and SCX HPLC.

Example 20

Materials and Methods for Testing Antibacterial Activity

Bacterial strains were obtained from the American Type Culture Collection (ATCC) or the *E. coli* Genetic Stock Center at Yale University. *E. coli* strain AS19 was obtained from Dr. Pete Nielsen (University of Copenhagen, Denmark). All pure culture experiments were done in 96-well plates. OD600 readings and plating of cells for CFU/ml determinations were done in triplicate. *E. coli* AS19 and SM101, which have defects in lipopolysaccharide synthesis that result in outer membrane permeability to high MW solutes, were grown aerobically in LB broth at 37° C., and 30° C., respectively. *E. coli* strain W3110 was grown aerobically in LB broth at 37° C.

*E. coli* AS19 and SM105 were grown in LB broth (supplemented with 100 μg/ml ampicillin for transformants that expressed luciferase) to $OD_{600}$=0.12, centrifuged (4,000×g, 10 min, 20° C.), and resuspended in 5% mucin (type II, Sigma Chemical Co., St. Louis)/PBS to final concentrations as follows: AS19, $1.5×10^8$ CFU/ml; SM105, $5.7×10^7$ CFU/ml; AS19 (pT7myc-luc), $7.2×10^9$ CFU/ml. *E. coli* W3110 to be used for mouse infection studies was grown in LB broth at 37° C. to $OD_{600}$=0.15, concentrated by centrifuging (4,000×g, 10 min, 20° C.) to $7×10^9$ CFU/mL, and resuspended in 5% mucin/PBS to a final concentration of $1.5×10^8$ CFU/mL.

Reporter gene. Standard molecular biology procedures were used for all constructions. All constructs were sequenced. The acpP-luc reporter (pCNacpP-luc) was made by ligating a SalI-NotI restriction fragment of luc with the SalI-NotI fragment of pCiNeo (Promega Corp., Madison, Wis.), removing the adenosine from the start codon by site-directed mutagenesis, then directionally cloning a synthetic fragment of *E. coli* acpP (bp −17 to +23, inclusive, where +1 is adenosine of the start codon) between the NheI-SalI sites. Luciferase enzyme activity was measured in bacteria as described (Geller, Deere et al. 2003).

Cell-free protein synthesis. Bacterial, cell-free protein synthesis reactions were performed by mixing reactants on ice according to the manufacturer's instruction (Promega Corp.). Reactions were programmed with mRNA synthesized in a cell-free RNA synthesis reaction (Ambion, Inc., Austin, Tex., MEGAscript T7 High Yield Transcription Kit) programmed with pCNacpP-luc. Where indicated, cell-free reactions were composed with rabbit reticulocyte lysate as described by the manufacturer (Promega Corp.). PMO was added to a final concentration of either 100 nM or 200 nM as indicated. After 1 hour at 37° C., the reactions were cooled on ice and luciferase was measured as described (Geller, Deere et al. 2003).

Animals. Female, 6 to 8 week old Swiss Webster or Balb/C mice (Simonsen Labs, Inc., Gilroy, Calif.) were used in all but one experiment, but identical results were obtained with males. Infection was established as described in (Frimodt-Moller, Knudsen et al. 1999). Each mouse was injected IP with 0.1 ml of bacteria resuspended in 5% mucin/PBS, then immediately injected IP with 0.1 ml of PMO (3.0 mg/ml) or PBS. At various times after infection (as indicated in the figures), groups (n=3 to 5) of mice were injected IP with 2.0 ml PBS, and their abdomens gently massaged for 2 min. Peritoneal lavage was removed and stored on ice for ~1 hour. The lavages were diluted in PBS and plated in triplicate on LB to determine CFU. In one experiment, blood samples (30 to 50 μL) were collected from mice via the saphenous vein, diluted in PBS, and plated in triplicate on LB to determine CFU.

Luciferase and western blot. Peritoneal lavages (1.00 ml) from mice infected with AS19 (pT7myc-luc) were centrifuged (10,000×g, 2 min, 4° C.) and the supernatants discarded. The pellets were resuspended in 50 μl PBS. An aliquot of resuspended cells was mixed with an equal volume of 2× cell culture lysis reagent (Promega, Inc., Madison, Wis.) and frozen at −85° C. Frozen lysates were thawed and luciferase light production was measured in duplicate in a luminometer as described (Geller, Deere et al. 2003). A second aliquot of the cell suspension was mixed with 2×SDS sample buffer and analyzed by western blot using 4-20% gradient Gene Mate Express Gels (ISC BioExpress, Inc., Kaysville, Utah). Blots were prepared with primary antibody to luciferase (Cortex Biochmical, San Leandro, Calif.) or antisera to OmpA (Geller and Green 1989), secondary goat anti-rabbit IgG-horse radish peroxidase conjugate (Santa Cruz Biotechnology, Inc., Santa, Cruz, Calif.), and ECL Western Blotting Reagent (Amersham Biosciences, Buckinghamshire, England). Film negatives were scanned and digitized on an Kodak Image Station 440 CF. The net intensity of each band was calculated by subtracting the mean background intensity. Luciferase protein was normalized to OmpA by dividing the net intensity of the luciferase band by the net intensity of the OmpA band in the same sample. The % inhibition was calculated by subtracting the mean luciferase/OmpA of luc PMO-treated mice from mean luciferase/OmpA of nonsense PMO-treated mice, dividing the difference by mean luciferase/OmpA of nonsense PMO-treated mice, then multiplying by 100%.

Statistical Analysis. Spearman's rank-order correlation was used to analyze correlations between the inhibitory effects of PMO and either G+C content or secondary structure score of each PMO. Individual mouse CFU/ml values were transformed logarithmically for statistical analysis using InStat statistical software (GraphPad Software, San Diego, Calif.). Differences in treatment group means were analysed with unpaired t test, not assuming equal variances, with Welch correction. Treatment group values were analysed for Gaussian distributions using the method of Kolmogorov and Smirnov, which confirmed in all analyses the normality test of the data. A one-tailed t test was applied to differences in means between AcpP PMO and either PBS or scrambled PMO treatment groups, whereas two-sided t test was applied in all other analyses.

Oligomer Sequences. Exemplary targeting oligomers used in describing the present invention are listed below in Table 3. The listed oligomers all target *E. coli*, the experimental bacterial strain used in experiments in support of the invention. Table 4 lists the peptides of the invention and the peptide-PMO conjugates used in experiments in support of the invention. The cationic (1-piperazino) phosphinylideneoxy linkage at each position is indicated with a "+" in Tables 3 and 4.

TABLE 3

PMO Sequences

| PMO # | Sequence (5' to 3') | Target | SEQ ID NO |
|---|---|---|---|
| 62-1 | TTC TTC GAT AGT GCT CAT AC | acpP-20 mer | 62 |
| 62-2 | TC TTC GAT AGT GCT CAT A | acpP-18 mer | 63 |
| 62-3 | C TTC GAT AGT GCT CAT | acpP-16 mer | 64 |
| 62-4 | TC GAT AGT GCT CAT | acpP-14 mer | 65 |
| 169 | C TTC GAT AGT G | acpP-11 mer | 66 |
|  | C+TTCGA+TAGT+G | acpP-11 mer | 66 |
| 379 | TTC GAT AGT G | acpP-10 mer | 67 |
| 380 | TTC GAT AGT | acpP-9 mer | 68 |
| 381 | TC GAT AGT | acpP-8 mer | 69 |
| 382 | TC GAT AG | acpP-7 mer | 70 |
| 383 | C GAT AG | acpP-6 mer | 71 |
| 62-5 | TTG TCC TGA ATA TCA CTT CG | Nonsense control-acpP | 72 |
| 62-7 | G TCC TGA ATA TCA CTT | Nonsense control-acpP | 73 |
| 62-8 | TCG TGA GTA TCA CT | Nonsense control-acpP | 74 |
| 170 | TCT CAG ATG GT | Nonsense control-acpP | 75 |

TABLE 3-continued

PMO Sequences

| PMO # | Sequence (5' to 3') | Target | SEQ ID NO |
|---|---|---|---|
| 384 | AAT CGG A | Nonsense control-acpP | 76 |
|  | ACG TTG AGG C | Luc | 77 |
|  | TCC ACT TGC C | luc nonsense | 78 |

TABLE 4

Peptide and Peptide-PMO Sequences

| Name | Sequence (Amino to Carboxy Terminus, 5' to 3') | SEQ ID NO |
|---|---|---|
| RFF | N-RFFRFFRFFAhxβ3Ala-COOH | 79 |
| RTR | N-RTRTRFLRRTAhxrβAla-COOH | 80 |
| RFFR | N-RFFRFFRFFRAhxβAla-COOH | 81 |
| KTR | N-KTRTKFLKKTAhxβAla-COOH | 82 |
| KFF | N-KFFKFFKFFAhxβAla-COOH | 83 |
| KFFK | N-KFFKFFKFFKAhxβAla-COOH | 84 |
| (RFF)₂ | N-RFFRFFAhxβAla-COOH | 85 |
| (RFF)₂R | N-RFFRFFRAhxβAla-COOH | 86 |
| RAhx | N-RAhxAhxRAhxAhxRAhxAhxβAla-COOH | 87 |
| RFF-AcpP11 | N-RFFRFFRFFAhxβAla-CTTCGATAGTG-3' | 88 |
| RTR-AcpP11 | N-RTRTRFLRRTAhxβAla-CTTCGATAGTG-3' | 89 |
| RFFR-AcpP11 | N-RFFRFFRFFRAhxβAla-CTTCGATAGTG-3' | 90 |
| (RFF)₂-AcpP11 | N-RFFRFFAhxβAla-CTTCGATAGTG | 91 |
| (RFF)₂R-AcpP11 | N-RFFRFFRAhxβAla-CTTCGATAGTG | 92 |
| RAhx-AcpP11 | N-RAhxAhxRAhxAhxRAhxAhxβAla- | 93 |
| (RAhxR)₄ | N-RAhxRRAhxRRAhxRRAhxRAhxβAla-COOH | 97 |
| (RAhxR)₄-AcpP11+ | N-RAhxRRAhxRRAhxRRAhxRAhxβAla-C+TTCGA+TAGT+G | 98 |

Example 21

Acyl Carrier Protein as an Endogenous Bacterial Gene Target

The effect of PMO was tested on an endogenous bacterial gene that encodes acyl carrier protein, acpP, which is essential for viability (Zhang and Cronan 1996) and has been used previously to inhibit bacterial growth (Good, Awasthi et al. 2001; Geller, Deere et al. 2003). PMO from 6 to 20 bases in length and complementary to the region around the start codon in mRNA for acpP (Table 3, SEQ ID NOS:62-71, respectively) were added to growing cultures of AS19 and growth at 37° C. was monitored by optical density and viable cell counts. Growth curves were normal for all cultures except for that with the 11 base PMO, which caused significant inhibition (FIG. 3A). Slight and reproducible, but statistically insignificant inhibitions of OD occurred in cultures with the 10 and 14 base PMO. Viable cells were significantly reduced in 8 hour cultures that contained PMO of 10, 11 or 14 bases (FIG. 3B). No reduction in CFU was apparent in cultures treated with PMO of less than 10 or more than 14 bases in length. Cultures without PMO, or with nonsense base sequences (7c, 14c and 20c; SEQ ID NOS:76, 74 and 72, respectively) did not demonstrate growth inhibition.

PMO of various lengths (from 6 to 20 bases; SEQ ID NOS:62-71, respectively) and targeted to acpP were added to bacterial, cell-free protein synthesis reactions programmed to express an acpP-luc fusion reporter. The results (FIG. 4) show that PMO 11 to 20 bases in length inhibited reporter expression to about the same extent. PMO shorter than 11 bases in length, or nonsense sequence controls (16c and 20c; SEQ ID NOS:73 and 72, respectively) did not inhibit luciferase expression significantly.

at 24 hours post-infection. By 4 hours post-infection the CFU of acpP PMO-treated mice were 70% lower than the CFU of nonsense PMO-treated mice (FIG. 6).

The above results with acpP and nonsense PMOs suggest that inhibition was sequence specific. To demonstrate directly a sequence-specific effect, mice were infected with an *E. coli* AS19 that expresses firefly luciferase, then treated at 0 and 13 hours post-infection with a PMO (luc; SEQ ID NO:77) complementary to the region around the start codon of the luciferase transcript, or a nonsense PMO (luc nonsense; SEQ ID NO:78). Peritoneal lavages were collected at 13 and 22 hours post-infection and analyzed for CFU, luciferase activity, and luciferase and OmpA protein by western immunoblot analysis. As expected, the results show no inhibition of growth with the luc PMO treatment compared to nonsense PMO treatment (Table 5). Luciferase activity in samples from luc PMO-treated mice was inhibited 53% and 46% at 13 and 22 hours, respectively, compared to samples from nonsense PMO-treated mice (Table 5).

Western blot analysis agreed closely with the results of luciferase activity. In samples from luc PMO-treated mice, there was a 68% and 47% reduction in the amount of luciferase protein at 13 and 22 hours, respectively, compared to samples from nonsense PMO-treated mice (Table 5).

TABLE 5

Gene Specific Inhibition

| | | | Luciferase Activity | | | Western Blot | | |
|---|---|---|---|---|---|---|---|---|
| PMO Treatment | Time after treatment (h) | CFU/ml (×10$^6$) | Mean (SEM) n = 8 | P | % Inhibition | Luc/OmpA Mean (SEM) n = 7-8 | P | % Inhibition |
| Luc | 13 | 6.3 | 2.90 (0.629) | .0035 | 53 | 0.122 (.0312) | .0002 | 68 |
| Nonsense | 13 | 4.3 | 6.19 (0.773) | | 0 | 0.382 (.0296) | | 0 |
| Luc | 22 | 0.96 | 3.20 (0.582) | .0093 | 46 | 0.147 (.0363) | .0145 | 57 |
| Nonsense | 22 | 0.39 | 8.12* (1.94) | | 0 | 0.339 (.0668) | | 0 |

Example 22

In Vivo Antisense Antibacterial Activity

Groups of 12 mice in each of three treatment groups were injected IP with *E. coli* strain AS19, which has a genetic defect that makes it abnormally permeable to high MW solutes. Immediately following infection, each mouse was injected IP with 300 □g of an 11-base PMO complementary to acpP (PMO 169; SEQ ID NO:66), an 11-base nonsense sequence control PMO (PMO 170; SEQ ID NO:75), or PBS. Peritoneal ravages were collected at 2, 7, 13, and 23 hours post-infection, and plated for bacteria. The results show that at all times analyzed, the acpP PMO-treated mice had significantly (P<0.05) lower CFU than the mice treated with either nonsense PMO or PBS (FIG. 5). The differences between the acpP PMO-treated group and the nonsense PMO control ranges from 39-fold at 2 hours to 600-fold at 23 hours.

The same PMOs were again tested, except with *E. coli* strain SM105, which has a normal outer membrane. AcpP PMO reduced CFU by 84% compared to nonsense PMO at 12 hours post-infection. There was no reduction of CFU at 2, 6, or 24 hours (FIG. 6). Mice were injected with a second dose Example 23

Enhanced Anti-Bacterial Properties of Peptide-Conjugated PMO

PMO conjugated at the 5' terminus with a series of three different peptides were evaluated for their antibacterial properties. The 11 mer PMO that targets the *E. coli* acpP gene (SEQ ID NO:66) was used as the antisense oligomer moiety and conjugated to either the RFF, RTR or RAhx peptides (SEQ ID NOS:79-80 and SEQ ID NO:87, respectively) to produce peptide-conjugated PMOs (P-PMOs) RFF-AcpP11, RTR-AcpP11 and RAhx-AcpP11 (SEQ ID NOS:88-89 and SEQ ID NO:93, respectively).

Figure 11:
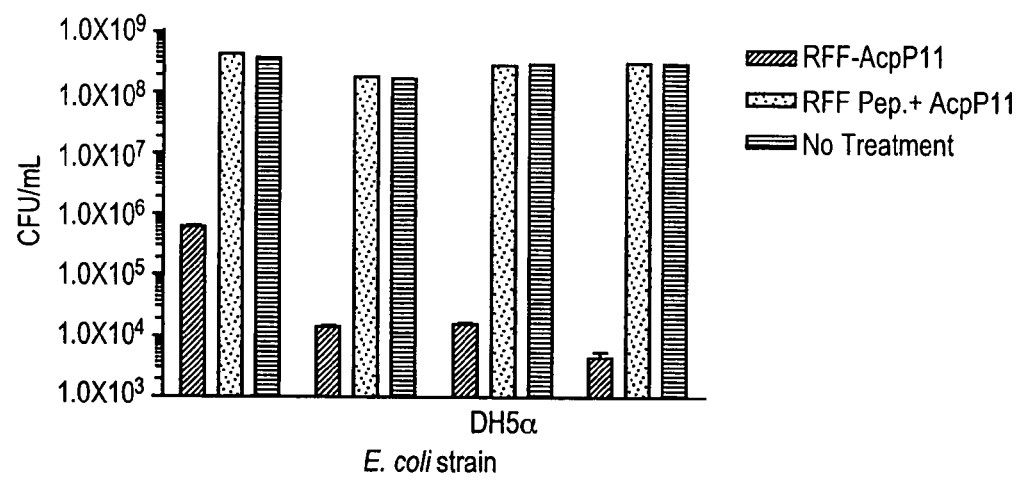
FIG. 11 shows the colony-forming units per milliliter (CFU/ml) of four strains of *E. coli* after eight hours incubation in the presence of the RFF-AcpP11 P-PMO compared to no treatment and treatment with a mixture of the AcpP11 PMO and the RFF peptide.

Four laboratory strains of *E. coli* (W3110, MIC2067, DH5α, SM105) were treated with 20 μM RFF-AcpP11 PPMO (SEQ ID NO:88), 20 μM free RFF peptide (SEQ ID NO:79) with unconjugated AcpP11 PMO (SEQ ID NO:66), or received no treatment (control) in LB broth, then were incubated at 37° C. for 24 hours. Every hour for 8 hours then at 24 hours the OD600 values (turbidity measurement) of the cultures were measured using a spectrophotometer. After 8 hours, aliquots of the cultures were diluted then plated onto LB agar plates and incubated for 24 hours at 37° C. After incubation, the colonies were counted by hand and the colony formation units/mL (CFU/mL) for each treatment were calculated. FIGS. 7 to 10 show the 24 hour growth curves for strains W3110, MIC2067, DH5α and SM105, respectively, in the presence of the RFF-AcpP11 P-PMO. FIG. 11 shows the CFU/ml after 8 hours treatment for the four strains of *E. coli*.

Using identical conditions as described above, *E. coli* W3110 was treated with three different P-PMOs (RAhx-AcpP11, RTR-AcpP11 and RFF-AcpP11) or received no treatment. FIG. 12 shows the CFU/ml after 8 hours of treatment with the three different P-PMOs compared to no treatment.

*E. coli* W3110 was treated with a short dilution series of RFF peptide at 5 µM, 20 µM, 50 µM and 100 µM, 20 µM RFF free peptide mixed with AcpP11 PMO, 20 µM RFF-AcpP11 P-PMO, 10 µM ampicillin or no treatment. FIG. 13 shows the CFU/ml after 8 hours for each treatment. This data strongly supports the conclusion that only the P-PMO and ampicillin showed antibacterial activity and that the delivery peptide must be conjugated to the PMO for this effect. Furthermore, the RFF-AcpP11 P-PMO demonstrates an approximately 10 fold improved antibacterial activity at 10 µM compared to ampicillin at the same concentration.

A series of dose-response experiments were performed where *E. coli* W3110 was exposed to RFF-AcpP11, RTR-AcpP11, and ampicillin in pure culture. *E. coli* W3110 was treated with a dilution series of RFF-AcpP11, RTR-AcpP11 or ampicillin (80 µM, 40 µM, 20 µM, 10 µM, 5 µM, 2.5 µM) or received no treatment. Determination of 50% inhibitory concentration values ($IC_{50}$) for RFF-AcpP11, RTR-AcpP11, and ampicillin were made using standard methods. FIG. 14 shows the dose response curves for each of the two PPMOs compared to ampicillin and the associated $IC_{50}$ values of 3.7, 12.1 and 7.7 mM for RFF-AcpP11, RTR-AcpP11 and ampicillin, respectively.

Figure 15:
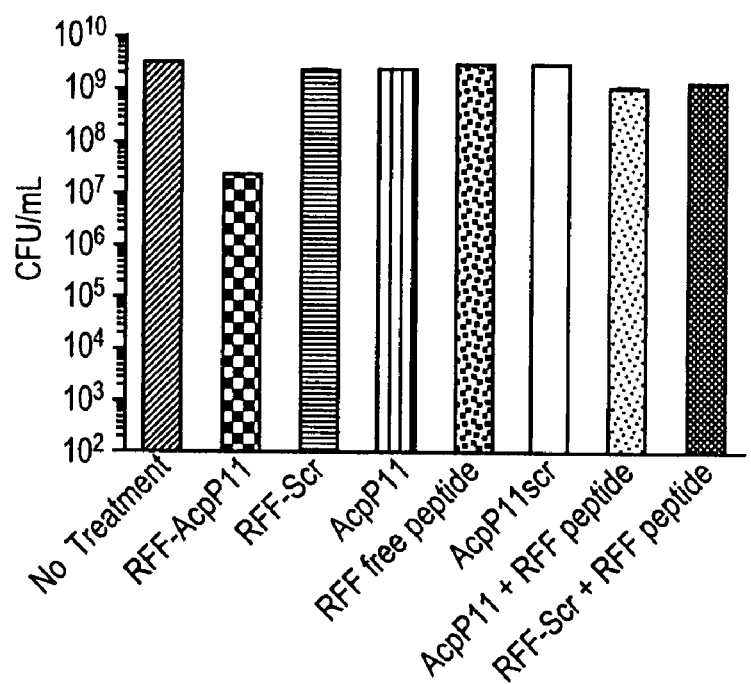
FIGS. 15 and 16 show the effect of RFF-AcpP11 P-PMO on *S. typhimurium* and an enterpathogenic strain of *E. coli* (O127:H6) as measured by CFU/ml after eight hours of treatment compared to no treatment, AcpP11 alone, RFF peptide alone, scrambled controls, and a mixture of AcpP11 and RFF peptide.
Figure 16:
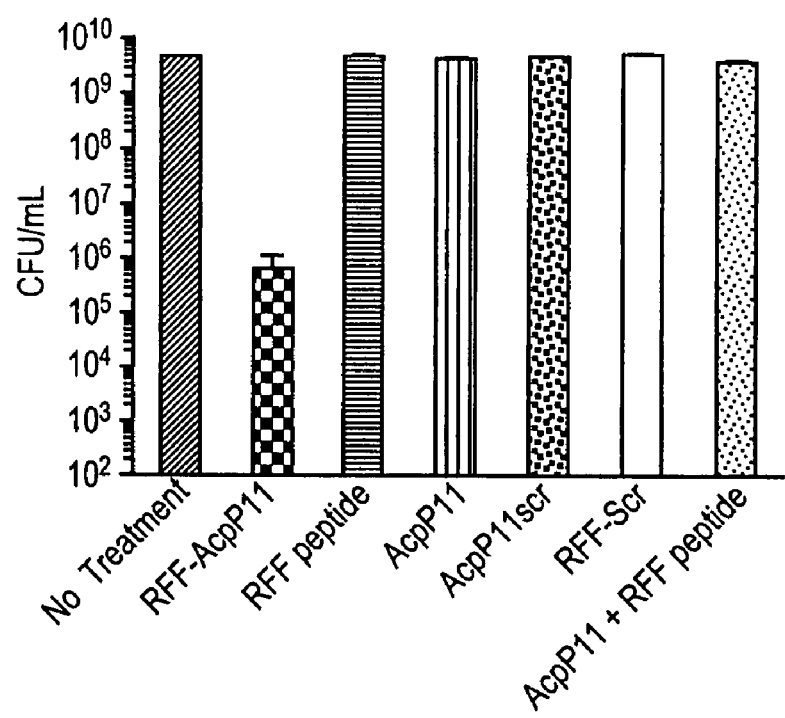

The sensitivity of *Salmonella typhimurium* 1535 and a clinically isolated enterpathogenic strain of *E. coli* (EPEC strain O127:H6) to RFF-AcpP11 P-PMO in culture was determined. The target sequences for AcpP11 (SEQ ID NOS:2 and 8) in *S. typhimurium* and *E. coli* are identical. Both strains were treated with 20 □M of RFF-AcpP11 P-PMO, RFF free peptide mixed with unconjugated AcpP11 PMO, AcpP11scr PMO, RFF-Scr P-PMO, RFF free peptide mixed with unconjugate AcpP11 PMO or no treatment. FIGS. 15 and 16 show the CFU/mL after 8 hours treatment for *S. typhimurium* and EPEC strain O127:H6. This data clearly demonstrate the utility of the RFF-AcpP11 compound as an antibacterial agent against clinically relevant bacterial isolates.

Example 24

Antibacterial Activity of Peptide-Conjugated PMO Targeting *Burkholderia* and *Pseudomonas* Species

Figure 17:
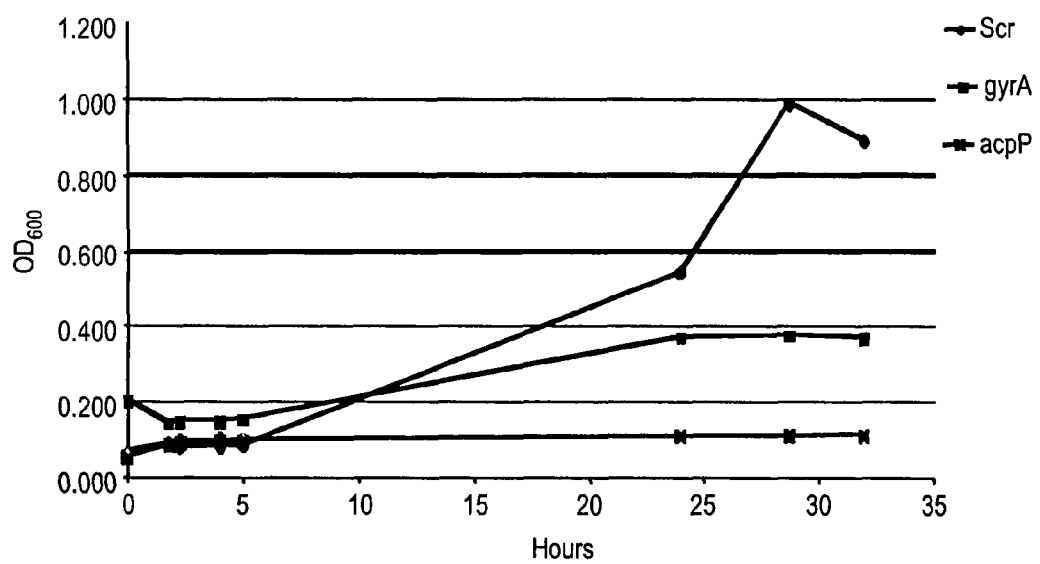
FIGS. 17 and 18 show the effect of RFFR-conjugated P-PMOs on the growth of *Burkholderia cenocepacia* and *Pseudomonas aeruginosa*, respectively.

*Burkholderia cenocepacia* growth in the presence of peptide-conjugated PMO was determined using the compounds of the invention. A stationary phase culture of *B. cenocepacia* was diluted to $5 \times 10^5$ cfu/ml in Mueller-Hinton broth. The peptide-conjugated PMO that target the acpP and gyrA genes were added to identical cultures to a final concentration of 200 µmol/L. The cultures were grown aerobically at 37° C. and optical density was monitored. After 36 hours, each culture was diluted and plated to determine viable cell count as colony forming units per ml (CFU/ml). All peptide-conjugated PMOs had the same peptide attached to the 5' end, which was (RFF)₃RAhxβAla (SEQ ID NO:81). All PMOs were 11 bases in length and targeted to regions around the start codon of acyl carrier protein (acpP) or the DNA gyrase subunit A (gyrA) as described above. Scr is a negative control, scrambled base sequence peptide-conjugated PMO that has no complementary target in *B. cenocepacia*. FIG. 17 shows the inhibition of *Burkholderia cenocepacia* growth, as measured by optical density, by the gyrA and acpP peptide-conjugated PMO compared to the Scr control. The viable cell count after 36 hours treatment was less than $1 \times 10^4$ CFU/ml for the peptide-conjugated PMOs targeting the acpP and gyrA genes whereas for the Scr control peptide-conjugated PMO the viable cell count was $8.5 \times 10^7$ CFU/ml. Similar results were obtained using these PMO against *B. multivorans* and B. gen.II.

Figure 18:
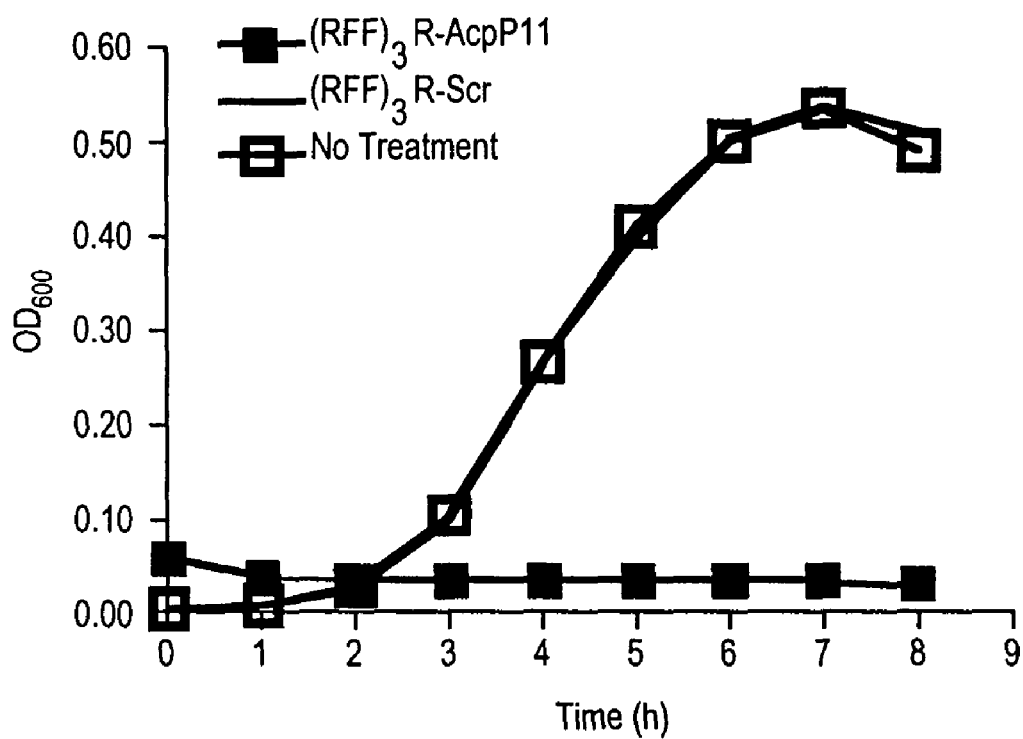

Similar experiments targeting *Pseudomonas aeruginosa* using RFFR (SEQ ID NO:81) conjugated to a PMO that targets the *P. aeruginosa* acpP gene. The RFFR-AcpP PMO targeted to acpP was added to a growing culture of *P. aeruginosa* in Mueller-Hinton broth at a 20 micromolar concentration. Aerobic growth at 37° C. was measured by optical density at 600 nm. The results shown in FIG. 18 show complete inhibition of growth and the scrambled base sequence control had no effect on growth.

Example 25

Enhanced In Vivo Anti-Bacterial Properties of a Peptide-Conjugated PMO Containing Cationic Intersubunit Linkages (P-PMO+)

A PMO having cationic intersubunit linkages and conjugated with an arginine rich peptide was evaluated for its antibacterial properties in a dose-response study. The 11mer cationic PMO+ that targets the *E. coli* acpP gene (C+TTCGA+TAGT+G, SEQ ID NO: 66) was used as the antisense oligomer moiety and conjugated at the 3' terminus to the (RAhxR)₄ peptide (SEQ ID NO: 97) to produce the cationic peptide-conjugated (RAhxR)₄-AcpP11+P-PMO+ (SEQ ID NO: 98).

Groups of 2 to 4 mice in each of six treatment groups were injected IP with $1.5 \times 10^7$ CFU of *E. coli* strain W3110. Each mouse was then injected IP with water control or a 1, 10, 30, 100, or 300 µg dose of (RAhxR)₄-AcpP11+ (SEQ ID NO: 98) administered both at 15 minutes and 12 hours post infection. Blood samples were collected and plated to determine CFU/mL at 2, 6, 12, 24, and 48 hours post infection. Body temperature was recorded as an objective criterion of terminal illness at the same time points as blood collection, with a threshold body temperature of 27.9° C. or below predicting terminal illness and ensuing death. Mouse survival was also tracked at same the time points as blood collection and scored as a death if body temperature dropped below 28° C. or if mouse was found dead.

The results show minor efficacy in the 1 µg group while full protection up to termination of the study at 48 hours post infection was observed in all groups of mice administered 10 µg and above (FIG. 19A). A dose-dependent reduction in CFU was observed, ranging from 0.5 to 4 orders of magnitude below water control for the 1 µg and 300 µg groups, respectively, by 2 hours post infection. By 12 hours post infection, CFU was reduced from 2 to 4 orders of magnitude below water control for the 10 µg and 300 µg groups, respectively (FIG. 19B). At 48 hours post infection, body temperatures ranged from 36.3 to 37.4° C. for the 10 µg and 300 µg groups, respectively, while all mice in the water control and 1 µg groups were dead by 12 and 24 hours post infection, respectively (FIG. 19C). No treatment-related toxicity was observed in any of the groups.

Although the application has been described with respect to particular embodiments, methods, and applications, it will be appreciated that various changes and modifications may be made without departing from the invention.

Sequence Listing:

Sequence Listing

| Name | Sequence (5' to 3') or (amino to carboxyl) | SEQ ID NO |
|---|---|---|
| E. coli ftsZ | GAGAGAAACTATGTTTGAACCAATGGAACTT | 1 |
| E. coli acpP | ATTTAAGAGTATGAGCACTATCGAAGAACGC | 2 |
| E. coli gyrA | TAGCGGTTAGATGAGCGACCTTGCGAGAGAA | 3 |
| E. coli O157:H7 ftsZ | GAGAGAAACTATGTTTGAACCAATGGAACTT | 4 |
| E. coli O157:H7 acpP | ATTTAAGAGTATGAGCACTATCGAAGAACGC | 5 |
| E. coli O157:H7 gyrA | TAGCGGTTAGATGAGCGACCTTGCGAGAGAA | 6 |
| S. typhimurium ftsZ | GAGAGAGATTATGTTTGAACCTATGGAACTA | 7 |
| S. typhimurium acpP | ATTTAAGAGTATGAGCACTATCGAAGAACGC | 8 |
| S. typhimurium gyrA | TAGCGGTTAGATGAGCGACCTTGCGAGAGAA | 9 |
| P. aeruginosa ftsZ | GAGAGGGGAAATGTTTGAACTGGTCGATAAC | 10 |
| P. aeruginosa acpP | AAAACAAGGTATGAGCACCATCGAAGAACGC | 11 |
| P. aeruginosa gyrA | CAGGCTTCTCATGGGCGAACTGGCCAAAGAA | 12 |
| V. cholera ftsZ | GAGATAACACATGTTTGAACCGATGATGGAA | 13 |
| V. cholera acpP | ACTATATTGGATGGTTTATATGTCTATCTCT | 14 |
| V. cholera gyrA | TAATGGCTCTATGAGCGATCTAGCTAAAGAG | 15 |
| N. ghonorrhoea ftsZ | GAGTTTTTGAATGGAATTTGTTTACGACGT | 16 |
| N. ghonorrhoea acpP | AACGACTGATATGTCAAACATCGAACAACA | 17 |
| N. ghonorrhoea gyrA | CATTGAAACCATGACCGACGCAACCATCCG | 18 |
| S. aureus ftsZ | GGAAATTTAAATGTTAGAATTTGAACAAGGA | 19 |
| S. aureus gyrA | GGAACTCTTGATGGCTGAATTACCTCAATCA | 20 |
| S. aureus fmhB | ATCATAAATCATGGAAAAGATGCATATCAC | 21 |
| M. tuberculosis ftsZ | CTCTAAGCCTATGGTTGAGGTTGAGAGTTTG | 22 |
| M. tuberculosis acpP | CCCGGGCGCGATGTGGCGATATCCACTAAGT | 23 |
| M. tuberculosis gyrA | CGAGGAATAGATGACAGACACGACGTTGCCG | 24 |
| M. tuberculosis pimA | GGAAAGCCTGATGCGGATCGGCATGATTTG | 25 |
| M. tuberculosis cysS2 | CTGGCACGTCGTGACCGATCGGGCTCGCTT | 26 |
| H. pylori ftsZ | GAATGTGGCTATGGTTCATCAATCAGAGATG | 27 |
| H. pylori acpP | AGTTTTAATTATGGCTTTATTTGAAGATATT | 28 |
| H. pylori gyrA | AGGGAGACACATGCAAGATAATTCAGTCAAT | 29 |
| S. pneumoniae ftsZ | AAAATAAATTATGACATTTTCATTTGATACA | 30 |
| S. pneumoniae acpP | GAGTCCTATCATGGCAGTATTTGAAAAAGTA | 31 |
| S. pneumoniae gyrA | GCATTTATTAATGCAGGATAAAAATTTAGTG | 32 |
| T. palladium ftsZ | TGGGAGGGGAATGATGAATATAGAGCTTGCA | 33 |
| T. palladium acpP | TGCCCCGTGGATGAGTTGTTCTTAAGAATGA | 34 |

Sequence Listing-continued

| Name | Sequence (5' to 3') or (amino to carboxyl) | SEQ ID NO |
|---|---|---|
| *T. palladium* gyrA | TGCCCGCCCTATGGAAGAAATTAGCACCCCA | 35 |
| *C. trachomatis* acpP | GGATCATAGGATGAGTTTAGAAGATGATGTA | 36 |
| *C. trachomatis* gyrA | AAACGAACTTATGAGCGACCTCTCGGACCTA | 37 |
| *B. henselae* ftsZ | AGGCAAATTAATTGGTAAAAAATTAGAGAG | 38 |
| *B. henselae* acpP | GGATTTCAACATGAGTGATACAGTAGAGCG | 39 |
| *B. henselae* gyrA | GTCTAAAGCTGTGACAGATCTAAACCCGCA | 40 |
| *H. influenza* ftsZ | GAGAACATCAATGCTATACCCAGAGTACCCT | 41 |
| *H. influenza* acpP | GGAAAAACAAATGAGTATTGAAGAACGCGTG | 42 |
| *H. influenza* gyrA | AGGAATACCAATGACGGATTCAATCCAATCA | 43 |
| *L. monocytogenes* ftsZ | AGGCAATAATATGTTAGAATTTGACACTAG | 44 |
| *L. monocytogenes* acpP | CGAACGCATAAAACTTTATGTGACCGGATA | 45 |
| *L. monocytogenes* gyrA | TTCTCTAACAATGGCAGAAACACCAAATCA | 46 |
| *Y. pestis* ftsZ | GAGAGAAACTATGTTTGAACCTATGGAACT | 47 |
| *Y. pestis* acpP | ATTTAAGAGTATGAGCACTATCGAAGAACG | 48 |
| *Y. pestis* gyrA | TAGCGGCTCAATGAGCGACCTTGCCAGAGA | 49 |
| *B. anthracis* ftsZ | GGATTTCGACATGTTAGAGTTTGATACTAC | 50 |
| *B. anthracis* acpP | GGTGAATGGAATGGCAGATGTTTTAGAGCG | 51 |
| *B. anthracis* gyrA | GTGCTCGTTGATGTCAGACAATCAACAACA | 52 |
| *B. mallei* ftsZ | GGAGGCAACAATGGAATTCGAAATGCTGGA | 53 |
| *B. mallei* acpP | CGGAGGGGTAATGGACAACATCGAACAACG | 54 |
| *B. mallei* gyrA | ATACGGATACATGGATCAATTCGCCAAAGA | 55 |
| *B. pseudomallei* ftsZ | GGAGGCAACAATGGAATTCGAAATGCTGGA | 56 |
| *B. pseudomallei* acpP | CGGAGGGGTAATGGACAACATCGAACAACG | 57 |
| *B. pseudomallei* gyrA | ATACGGATACATGGATCAATTCGCCAAAGA | 58 |
| *F. tularensis* ftsZ | GGAGTAAAATATGTTTGATTTTAACGATTC | 59 |
| *F. tularensis* acpP | AGGAAAAAATATGAGTACACATAACGAAGA | 60 |
| *F. tularensis* gyrA | GCGATAACTAATGTCTATAATTACTAAAGA | 61 |
| 62-1 | TTCTTCGATAGTGCTCATAC | 62 |
| 62-2 | TCTTCGATAGTGCTCATA | 63 |
| 62-3 | CTTCGATAGTGCTCAT | 64 |
| 62-4 | TCGATAGTGCTCAT | 65 |
| 169 (acpP, +5 to +15) | CTTCGATAGTG | 66 |
| (acpP+, +5 to +15) | C+TTCGA+TAGT+G | |
| 379 | TTCGATAGTG | 67 |
| 380 | TTCGATAGT | 68 |
| 381 | TCGATAGT | 69 |
| 382 | TCGATAG | 70 |
| 383 | CGATAG | 71 |

Sequence Listing-continued

| Name | Sequence (5' to 3') or (amino to carboxyl) | SEQ ID NO |
|---|---|---|
| 62-5 | TTGTCCTGAATATCACTTCG | 72 |
| 62-7 | GTCCTGAATATCACTT | 73 |
| 62-8 | TCGTGAGTATCACT | 74 |
| 170 | TCTCAGATGGT | 75 |
| 384 | AATCGGA | 76 |
| Luc | ACGTTGAGGC | 77 |
| Luc-nonsense | TCCACTTGCC | 78 |
| REF | N-RFFRFFRFFAhxβAla-COOH | 79 |
| RTR | N-RTRTRFLRRTAhxβAla-COOH | 80 |
| RFFR | N-RFFRFFRFFRAhxβAla-COOH | 81 |
| KTR | N-KTRTKFLKKTAhxβAla-COOH | 82 |
| KFF | N-KFFKFFKFFAhxβAla-COOH | 83 |
| KFFK | N-KFFKFFKFFKAhxβAla-COOH | 84 |
| (RFF)$_2$ | N-RFFRFFAhxβAla-COOH | 85 |
| (RFF)$_2$R | N-RFFRFFRAhxβAla-COOH | 86 |
| RAhx | N-RAhxAhxRAhxAhxRAhxAhxβAla-COOH | 87 |
| RFF-AcpP11 | N-RFFRFFRFFAhxβAla-CTTCGATAGTG | 88 |
| RTR-AcpP11 | N-RTRTRFLRRTAhxβAla-CTTCGATAGTG | 89 |
| RFFR-AcpP11 | N-RFFRFFRFFRAhxβAla-CTTCGATAGTG | 90 |
| (RFF)$_2$-AcpP11 | N-RFFRFFAhxβAla-CTTCGATAGTG | 91 |
| (RFF)$_2$R-AcpP11 | N-RFFRFFRAhxβAla-CTTCGATAGTG | 92 |
| RAhx-AcpP11 | N-RAhxAhxRAhxAhxRAhxAhxβAla- | 93 |
| acpP (−4 to +7) | TGCTCATACTC | 94 |
| acpP (+1 to +11) | ATAGTGCTCAT | 95 |
| acpP (+11 to +21) | GCGTTCTTCCG | 96 |
| (RAhxR)$_4$ | N-RAhxRRAhxRRAhxRRAhxRAhxβAla-COOH | 97 |
| (RAhxR)$_4$-AcpP11+ | N-RAhxRRAhxRRAhxRRAhxRAhxβAla- | 98 |

---

It is claimed:

1. A method for enhancing the antibacterial activity of an uncharged antisense oligonucleotide composed of morpholino subunits linked by phosphorus-containing intersubunit linkages joining a morpholino nitrogen of one subunit to a 5' exocyclic carbon of an adjacent subunit, where the oligonucleotide contains between 10-20 bases and a targeting sequence of at least 10 contiguous bases complementary to a bacterial RNA target, and where binding of the oligonucleotide to the RNA target region is effective to inhibit growth of a infectious bacterium in a mammalian host, comprising both of steps (a) and (b), or step (b) alone:
  (a) conjugating to the oligonucleotide, a carrier peptide (i) containing 8-14 amino acids composed of the subsequences selected from the group represented by XXY, XY, XZZ, XZ, XYX, YXX, YX, ZXZ, ZZX, and ZX, where (a) each X subunit independently represents arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$; (b) each Y subunit independently represents a neutral linear amino acid —C(O)—(CHR)m-NH—, where (i) m is 1 to 7 and each R is independently H or methyl, and (c) Z is an α-amino acid having a neutral side chain selected from a substituted or unsubstituted aralkyl, and (ii) coupled to the oligonucleotide at the peptide's C terminus, and
  (b) modifying the oligonucleotide to contain at least one and up to 50% intersubunit linkages comprising an optionally substituted piperazino group.

2. The method of claim 1, comprising both steps (a) and (b), wherein the carrier peptide is represented by the sequence $(RY'R)_p$ or $(RY')_n$, where R is arginine and Y' is a linear alkanoic acid having 2-7 carbon atoms in its backbone chain, and p is 2 to 5 and n is 2 to 8.

3. The method of claim 1, comprising both steps (a) and (b), wherein the carrier peptide is linked at its C-terminus to the 5' end of the oligonucleotide through a one- or two-amino acid linker.

4. The method of claim 3, wherein the linker is AhxβAla, where Ahx is 6-aminohexanoic acid and βAla is β-alanine.

5. The method of claim 1, comprising both steps (a) and (b), wherein the peptide is represented by $(RAhxR)_4$, where Ahx is 6-amino hexanoic acid.

6. The method of claim 1, comprising both steps (a) and (b), wherein the peptide is represented by $(RAhx)_6$, where Ahx is 6-amino hexanoic acid.

7. The method of claim 1, wherein said oligonucleotide has approximately equal-length 5', 3' and center regions, and the percentage of linkages comprising an optionally substituted piperazino group in said center region of the modified oligonucleotide is greater than about 70%.

8. The method of claim 1, wherein step (b) of the method is effective to enhance the anti-bacterial activity of said uncharged oligonucleotide, as measured by inhibition in bacterial growth in vitro over an eight-hour period, by a factor of at least 10 relative to the measured inhibition of the uncharged oligonucleotide in the absence of the carrier peptide.

9. The method of claim 8, wherein step (a) and step (b) of the method are effective to enhance the anti-bacterial activity of said uncharged oligonucleotide, as measured by inhibition in bacterial growth in vitro over an eight-hour period, by a factor of at least $10^2$ relative to the measured inhibition of the uncharged oligonucleotide in the absence of the carrier peptide.

10. The method of claim 1, wherein the morpholino subunits in the modified oligonucleotide are joined by phosphorodiamidate linkages, in accordance with the structure:

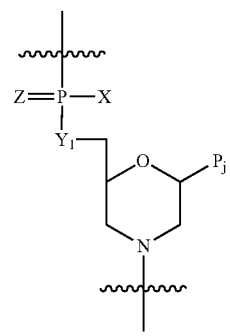

where
Z is S or O,
$X=NR^1R^2$ or $OR^6$,
Y=O or $NR^7$,
and intersubunit linkage is, at each occurrence, independently:
  (a) linkage (a), where each of $R^1$, $R^2$, $R^6$ and $R^7$ is independently hydrogen or lower alkyl; or (b1) linkage (b1), where X=$NR^1R^2$ and Y=O, and $NR^1R^2$ is a piperazino group, such that $R^1R^2$=—CHRCHRN($R^3$)($R^4$)CHRCHR—, wherein:

each R is, at each occurrence, independently H or $CH_3$, $R^4$ is H, $CH_3$ or an electron pair, and $R^3$ is H, lower alkyl, C(=NH)$NH_2$, Z-L-NHC(=NH)$NH_2$, or [C(O)CHR'NH]$_m$H, where Z is carbonyl (C(O)) or a direct bond, L is an optional linker up to 18 atoms in length comprising alkyl, alkoxy, or alkylamino groups, or combinations thereof, R' is a side chain of a naturally occurring amino acid or a one- or two-carbon homolog thereof, and m is 1 to 6;

and at least one linkage is linkage (b1).

11. The method of claim 10, wherein each of $R^1$ and $R^2$, in linkages of type (a), is methyl.

12. The method of claim 10, where, in linkages of type (b1), each R is H, $R^4$ is H, $CH_3$, or an electron pair, and $R^3$ is H, $CH_3$, C(=NH)$NH_2$, or C(O)-L-NHC(=NH)$NH_2$.

13. The method of claim 10 where, in linkages of type (b1), each R is H, $R^4$ is an electron pair, and $R^3$ is C(=NH)$NH_2$ or C(O)-L-NHC(=NH)$NH_2$.

14. The method of claim 13, wherein $R^3$ is C(O)-L-NHC(=NH)$NH_2$, and L is a hydrocarbon having the structure —$(CH_2)_n$—, where n is 1 to 12.

15. The method of claim 10, where, in linkages of type (b1), each R is H, and each of $R^3$ and $R^4$ is independently H or $CH_3$.

16. The method of claim 1, for treating a gram-negative bacterial infection, wherein the targeting sequence is complementary to a target sequence containing or within 20 bases, in a downstream direction, of the translational start codon of a bacterial mRNA that encodes acyl carrier protein (acpP).

17. The method of claim 1, for treating a gram-negative bacterial infection, wherein the targeting sequence is complementary to a target sequence containing or within 20 bases, in a downstream direction, of the translational start codon of a bacterial mRNA that encodes gyrase A subunit (gyrA).

* * * * *

SEQUENCE LISTING

<160> NUMBER OF SEQ ID NOS: 111

<210> SEQ ID NO 1
<211> LENGTH: 31
<212> TYPE: DNA
<213> ORGANISM: Escherichia coli

<400> SEQUENCE: 1
gagagaaact atgtttgaac caatggaact t          31

<210> SEQ ID NO 2

```
<211> LENGTH: 31
<212> TYPE: DNA
<213> ORGANISM: Escherichia coli

<400> SEQUENCE: 2
atttaagagt atgagcacta tcgaagaacg c                              31

<210> SEQ ID NO 3
<211> LENGTH: 31
<212> TYPE: DNA
<213> ORGANISM: Escherichia coli

<400> SEQUENCE: 3
tagcggttag atgagcgacc ttgcgagagaa                               31

<210> SEQ ID NO 4
<211> LENGTH: 31
<212> TYPE: DNA
<213> ORGANISM: Escherichia coli

<400> SEQUENCE: 4
gagagaaact atgtttgaac caatggaact t                              31

<210> SEQ ID NO 5
<211> LENGTH: 31
<212> TYPE: DNA
<213> ORGANISM: Escherichia coli

<400> SEQUENCE: 5
atttaagagt atgagcacta tcgaagaacg c                              31

<210> SEQ ID NO 6
<211> LENGTH: 31
<212> TYPE: DNA
<213> ORGANISM: Escherichia coli

<400> SEQUENCE: 6
tagcggttag atgagcgacc ttgcgagagaa                               31

<210> SEQ ID NO 7
<211> LENGTH: 31
<212> TYPE: DNA
<213> ORGANISM: Salmonella typhimurium

<400> SEQUENCE: 7
gagagagatt atgtttgaac ctatggaact a                              31

<210> SEQ ID NO 8
<211> LENGTH: 31
<212> TYPE: DNA
<213> ORGANISM: Salmonella typhimurium

<400> SEQUENCE: 8
atttaagagt atgagcacta tcgaagaacg c                              31

<210> SEQ ID NO 9
<211> LENGTH: 31
<212> TYPE: DNA
<213> ORGANISM: Salmonella typhimurium

<400> SEQUENCE: 9
tagcggttag atgagcgacc ttgcgagagaa                               31

<210> SEQ ID NO 10
```

```
<211> LENGTH: 31
<212> TYPE: DNA
<213> ORGANISM: Pseudomonas aeruginosa

<400> SEQUENCE: 10 gagagggaa atgtttgaac tggtcgataac                              31

<210> SEQ ID NO 11
<211> LENGTH: 31
<212> TYPE: DNA
<213> ORGANISM: Pseudomonas aeruginosa

<400> SEQUENCE: 11
aaaacaaggt atgagcacca tcgaagaacgc                             31

<210> SEQ ID NO 12
<211> LENGTH: 31
<212> TYPE: DNA
<213> ORGANISM: Pseudomonas aeruginosa

<400> SEQUENCE: 12
caggcttctc atgggcgaac tggccaaagaa                             31

<210> SEQ ID NO 13
<211> LENGTH: 31
<212> TYPE: DNA
<213> ORGANISM: Vibrio cholera

<400> SEQUENCE: 13
gagataacac atgtttgaac cgatgatgga a                            31

<210> SEQ ID NO 14
<211> LENGTH: 31
<212> TYPE: DNA
<213> ORGANISM: Vibrio cholera

<400> SEQUENCE: 14
actatattgg atggtttata tgtctatctc t                            31

<210> SEQ ID NO 15
<211> LENGTH: 31
<212> TYPE: DNA
<213> ORGANISM: Vibrio cholera

<400> SEQUENCE: 15
taatggctct atgagcgatc tagctaaaga g                            31

<210> SEQ ID NO 16
<211> LENGTH: 30
<212> TYPE: DNA
<213> ORGANISM: Neisseria gonorrhoea

<400> SEQUENCE: 16 gagttttga atggaatttg tttacgacgt                               30

<210> SEQ ID NO 17
<211> LENGTH: 30
<212> TYPE: DNA
<213> ORGANISM: Neisseria gonorrhoea

<400> SEQUENCE: 17
aacgactgat atgtcaaaca tcgaacaaca                              30

<210> SEQ ID NO 18
```

```
<211> LENGTH: 30
<212> TYPE: DNA
<213> ORGANISM: Neisseria gonorrhoea

<400> SEQUENCE: 18
cattgaaacc atgaccgacg caaccatccg                                      30

<210> SEQ ID NO 19
<211> LENGTH: 31
<212> TYPE: DNA
<213> ORGANISM: Staphylococcus aureus

<400> SEQUENCE: 19
ggaaatttaa atgttagaat ttgaacaagg a                                    31

<210> SEQ ID NO 20
<211> LENGTH: 31
<212> TYPE: DNA
<213> ORGANISM: Staphylococcus aureus

<400> SEQUENCE: 20
ggaactcttg atggctgaat tacctcaatc a                                    31

<210> SEQ ID NO 21
<211> LENGTH: 30
<212> TYPE: DNA
<213> ORGANISM: Staphylococcus aureus

<400> SEQUENCE: 21
atcataaatc atggaaaaga tgcatatcac                                      30

<210> SEQ ID NO 22
<211> LENGTH: 31
<212> TYPE: DNA
<213> ORGANISM: Mycobacterium tuberculosis

<400> SEQUENCE: 22
ctctaagcct atggttgagg ttgagagttt g                                    31

<210> SEQ ID NO 23
<211> LENGTH: 31
<212> TYPE: DNA
<213> ORGANISM: Mycobacterium tuberculosis

<400> SEQUENCE: 23
cccgggcgcg atgtggcgat atccactaagt                                     31

<210> SEQ ID NO 24
<211> LENGTH: 31
<212> TYPE: DNA
<213> ORGANISM: Mycobacterium tuberculosis

<400> SEQUENCE: 24
cgaggaatag atgacagaca cgacgttgccg                                     31

<210> SEQ ID NO 25
<211> LENGTH: 30
<212> TYPE: DNA
<213> ORGANISM: Mycobacterium tuberculosis

<400> SEQUENCE: 25
ggaaagcctg atgcggatcg gcatgatttg                                      30

<210> SEQ ID NO 26
```

```
<211> LENGTH: 30
<212> TYPE: DNA
<213> ORGANISM: Mycobacterium tuberculosis

<400> SEQUENCE: 26
ctggcacgtc gtgaccgatc gggctcgctt                                    30

<210> SEQ ID NO 27
<211> LENGTH: 31
<212> TYPE: DNA
<213> ORGANISM: Helicobacter pylori

<400> SEQUENCE: 27
gaatgtggct atggttcatc aatcagagat g                                  31

<210> SEQ ID NO 28
<211> LENGTH: 31
<212> TYPE: DNA
<213> ORGANISM: Helicobacter pylori

<400> SEQUENCE: 28
agttttaatt atggctttat ttgaagatat t                                  31

<210> SEQ ID NO 29
<211> LENGTH: 31
<212> TYPE: DNA
<213> ORGANISM: Helicobacter pylori

<400> SEQUENCE: 29
agggagacac atgcaagata attcagtcaa t                                  31

<210> SEQ ID NO 30
<211> LENGTH: 31
<212> TYPE: DNA
<213> ORGANISM: Streptococcus pneumoniae

<400> SEQUENCE: 30
aaaataaatt atgacatttt catttgatac a                                  31

<210> SEQ ID NO 31
<211> LENGTH: 31
<212> TYPE: DNA
<213> ORGANISM: Streptococcus pneumoniae

<400> SEQUENCE: 31
gagtcctatc atggcagtat ttgaaaaagt a                                  31

<210> SEQ ID NO 32
<211> LENGTH: 31
<212> TYPE: DNA
<213> ORGANISM: Streptococcus pneumoniae

<400> SEQUENCE: 32
gcatttatta atgcaggata aaaatttagt g                                  31

<210> SEQ ID NO 33
<211> LENGTH: 31
<212> TYPE: DNA
<213> ORGANISM: Treponema palladium

<400> SEQUENCE: 33
tgggagggga atgatgaata tagagcttgca                                   31

<210> SEQ ID NO 34
```

-continued

```
<211> LENGTH: 31
<212> TYPE: DNA
<213> ORGANISM: Treponema palladium

<400> SEQUENCE: 34
tgccccgtgg atgagttgtt cttaagaatg a                                    31

<210> SEQ ID NO 35
<211> LENGTH: 31
<212> TYPE: DNA
<213> ORGANISM: Treponema palladium

<400> SEQUENCE: 35
tgcccgccct atggaagaaa ttagcacccca                                     31

<210> SEQ ID NO 36
<211> LENGTH: 31
<212> TYPE: DNA
<213> ORGANISM: Chlamydia trachomatis

<400> SEQUENCE: 36
ggatcatagg atgagtttag aagatgatgt a                                    31

<210> SEQ ID NO 37
<211> LENGTH: 31
<212> TYPE: DNA
<213> ORGANISM: Chlamydia trachomatis

<400> SEQUENCE: 37
aaacgaactt atgagcgacc tctcggacct a                                    31

<210> SEQ ID NO 38
<211> LENGTH: 29
<212> TYPE: DNA
<213> ORGANISM: Bartonella henselae

<400> SEQUENCE: 38
aggcaaatta attggtaaaa aattagaga                                       29

<210> SEQ ID NO 39
<211> LENGTH: 30
<212> TYPE: DNA
<213> ORGANISM: Bartonella henselae

<400> SEQUENCE: 39
ggatttcaac atgagtgata cagtagagcg                                      30

<210> SEQ ID NO 40
<211> LENGTH: 30
<212> TYPE: DNA
<213> ORGANISM: Bartonella henselae

<400> SEQUENCE: 40
gtctaaagct gtgacagatc taaacccgca                                      30

<210> SEQ ID NO 41
<211> LENGTH: 31
<212> TYPE: DNA
<213> ORGANISM: Haemophilus influenzae

<400> SEQUENCE: 41
gagaacatca atgctatacc cagagtaccc t                                    31

<210> SEQ ID NO 42
```

```
<211> LENGTH: 31
<212> TYPE: DNA
<213> ORGANISM: Haemophilus influenzae

<400> SEQUENCE: 42
ggaaaaacaa atgagtattg aagaacgcgtg                                      31

<210> SEQ ID NO 43
<211> LENGTH: 31
<212> TYPE: DNA
<213> ORGANISM: Haemophilus influenzae

<400> SEQUENCE: 43
aggaatacca atgacggatt caatccaatc a                                     31

<210> SEQ ID NO 44
<211> LENGTH: 30
<212> TYPE: DNA
<213> ORGANISM: Listeria monocytogenes

<400> SEQUENCE: 44
aggcaataat atgttagaat ttgacactag                                       30

<210> SEQ ID NO 45
<211> LENGTH: 30
<212> TYPE: DNA
<213> ORGANISM: Listeria monocytogenes

<400> SEQUENCE: 45
cgaacgcata aaactttatg tgaccggata                                       30

<210> SEQ ID NO 46
<211> LENGTH: 30
<212> TYPE: DNA
<213> ORGANISM: Listeria monocytogenes

<400> SEQUENCE: 46
ttctctaaca atggcagaaa caccaaatca                                       30

<210> SEQ ID NO 47
<211> LENGTH: 30
<212> TYPE: DNA
<213> ORGANISM: Yersinia pestis

<400> SEQUENCE: 47
gagagaaact atgtttgaac ctatggaact                                       30

<210> SEQ ID NO 48
<211> LENGTH: 30
<212> TYPE: DNA
<213> ORGANISM: Yersinia pestis

<400> SEQUENCE: 48
atttaagagt atgagcacta tcgaagaacg                                       30

<210> SEQ ID NO 49
<211> LENGTH: 30
<212> TYPE: DNA
<213> ORGANISM: Yersinia pestis

<400> SEQUENCE: 49
tagcggctca atgagcgacc ttgccagaga                                       30

<210> SEQ ID NO 50
```

```
<211> LENGTH: 30
<212> TYPE: DNA
<213> ORGANISM: Bacillus anthracis

<400> SEQUENCE: 50
ggatttcgac atgttagagt ttgatactac                                30

<210> SEQ ID NO 51
<211> LENGTH: 30
<212> TYPE: DNA
<213> ORGANISM: Bacillus anthracis

<400> SEQUENCE: 51
ggtgaatgga atggcagatg ttttagagcg                                30

<210> SEQ ID NO 52
<211> LENGTH: 30
<212> TYPE: DNA
<213> ORGANISM: Bacillus anthracis

<400> SEQUENCE: 52
gtgctcgttg atgtcagaca atcaacaaca                                30

<210> SEQ ID NO 53
<211> LENGTH: 30
<212> TYPE: DNA
<213> ORGANISM: Burkholderia mallei

<400> SEQUENCE: 53
ggaggcaaca atggaattcg aaatgctgga                                30

<210> SEQ ID NO 54
<211> LENGTH: 30
<212> TYPE: DNA
<213> ORGANISM: Burkholderia mallei

<400> SEQUENCE: 54
cggaggggta atggacaaca tcgaacaacg                                30

<210> SEQ ID NO 55
<211> LENGTH: 30
<212> TYPE: DNA
<213> ORGANISM: Burkholderia mallei

<400> SEQUENCE: 55
atacggatac atggatcaat tcgccaaaga                                30

<210> SEQ ID NO 56
<211> LENGTH: 30
<212> TYPE: DNA
<213> ORGANISM: Burkholderia pseudomallei

<400> SEQUENCE: 56
ggaggcaaca atggaattcg aaatgctgga                                30

<210> SEQ ID NO 57
<211> LENGTH: 30
<212> TYPE: DNA
<213> ORGANISM: Burkholderia pseudomallei

<400> SEQUENCE: 57
cggaggggta atggacaaca tcgaacaacg                                30

<210> SEQ ID NO 58
```

```
<211> LENGTH: 30
<212> TYPE: DNA
<213> ORGANISM: Burkholderia pseudomallei

<400> SEQUENCE: 58
atacggatac atggatcaat tcgccaaaga                                              30

<210> SEQ ID NO 59
<211> LENGTH: 30
<212> TYPE: DNA
<213> ORGANISM: Francisella tularensis

<400> SEQUENCE: 59
ggagtaaaat atgtttgatt ttaacgattc                                              30

<210> SEQ ID NO 60
<211> LENGTH: 30
<212> TYPE: DNA
<213> ORGANISM: Francisella tularensis

<400> SEQUENCE: 60
aggaaaaaat atgagtacac ataacgaaga                                              30

<210> SEQ ID NO 61
<211> LENGTH: 30
<212> TYPE: DNA
<213> ORGANISM: Francisella tularensis

<400> SEQUENCE: 61
gcgataacta atgtctataa ttactaaaga                                              30

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 62
ttcttcgata gtgctcatac                                                         20

<210> SEQ ID NO 63
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 63
tcttcgatag tgctcata                                                           18

<210> SEQ ID NO 64
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 64
cttcgatagt gctcat                                                             16

<210> SEQ ID NO 65
<211> LENGTH: 14
<212> TYPE: DNA
<213> ORGANISM: Artificial Sequence
<220> FEATURE:
```

```
<223> OTHER INFORMATION: Synthetic Oligomer

<400> SEQUENCE: 65
tcgatagtgc tcat                                                         14

<210> SEQ ID NO 66
<211> LENGTH: 11
<212> TYPE: DNA
<213> ORGANISM: Artificial Sequence
<220> FEATURE:
<223> OTHER INFORMATION: Synthetic Oligomer

<400> SEQUENCE: 66
cttcgatagt g                                                            11

<210> SEQ ID NO 67
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 67
ttcgatagtg                                                              10

<210> SEQ ID NO 68
<211> LENGTH: 9
<212> TYPE: DNA
<213> ORGANISM: Artificial Sequence
<220> FEATURE:
<223> OTHER INFORMATION: Synthetic Oligomer

<400> SEQUENCE: 68 ttcgatagt                                                                9

<210> SEQ ID NO 69
<211> LENGTH: 8
<212> TYPE: DNA
<213> ORGANISM: Artificial Sequence
<220> FEATURE:
<223> OTHER INFORMATION: Synthetic Oligomer

<400> SEQUENCE: 69 tcgatagt                                                                 8

<210> SEQ ID NO 70
<211> LENGTH: 7
<212> TYPE: DNA
<213> ORGANISM: Artificial Sequence
<220> FEATURE:
<223> OTHER INFORMATION: Synthetic Oligomer

<400> SEQUENCE: 70 tcgatag                                                                  7

<210> SEQ ID NO 71
<211> LENGTH: 6
<212> TYPE: DNA
<213> ORGANISM: Artificial Sequence
<220> FEATURE:
<223> OTHER INFORMATION: Synthetic Oligomer

<400> SEQUENCE: 71 cgatag                                                                   6

<210> SEQ ID NO 72
```

```
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 72
ttgtcctgaa tatcacttcg                                                 20

<210> SEQ ID NO 73
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 73
gtcctgaata tcactt                                                     16

<210> SEQ ID NO 74
<211> LENGTH: 14
<212> TYPE: DNA
<213> ORGANISM: Artificial Sequence
<220> FEATURE:
<223> OTHER INFORMATION: Synthetic Oligomer

<400> SEQUENCE: 74
tcgtgagtat cact                                                       14

<210> SEQ ID NO 75
<211> LENGTH: 11
<212> TYPE: DNA
<213> ORGANISM: Artificial Sequence
<220> FEATURE:
<223> OTHER INFORMATION: Synthetic Oligomer

<400> SEQUENCE: 75
tctcagatgg t                                                          11

<210> SEQ ID NO 76
<211> LENGTH: 7
<212> TYPE: DNA
<213> ORGANISM: Artificial Sequence
<220> FEATURE:
<223> OTHER INFORMATION: Synthetic Oligomer

<400> SEQUENCE: 76 aatcgga                                                                7

<210> SEQ ID NO 77
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 77
acgttgaggc                                                            10

<210> SEQ ID NO 78
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 78
```
tccacttgcc    10

<210> SEQ ID NO 79
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 10
<223> OTHER INFORMATION: Xaa = 6-aminohexanoic acid
<220> FEATURE:
<221> NAME/KEY: MOD_RES
<222> LOCATION: 11
<223> OTHER INFORMATION: Xaa = beta-Alanine

<400> SEQUENCE: 79

Arg Phe Phe Arg Phe Phe Arg Phe Phe Xaa Xaa
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 11
<223> OTHER INFORMATION: Xaa = 6-aminohexanoic acid
<220> FEATURE:
<221> NAME/KEY: MOD_RES
<222> LOCATION: 12
<223> OTHER INFORMATION: Xaa = beta-Alanine

<400> SEQUENCE: 80

Arg Thr Arg Thr Arg Phe Leu Arg Arg Thr Xaa Xaa
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 11
<223> OTHER INFORMATION: Xaa = 6-aminohexanoic acid
<220> FEATURE:
<221> NAME/KEY: MOD_RES
<222> LOCATION: 12
<223> OTHER INFORMATION: Xaa = beta-Alanine

<400> SEQUENCE: 81

Arg Phe Phe Arg Phe Phe Arg Phe Phe Arg Xaa Xaa
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 11
<223> OTHER INFORMATION: Xaa = 6-aminohexanoic acid
<220> FEATURE:
<221> NAME/KEY: MOD_RES
<222> LOCATION: 12
<223> OTHER INFORMATION: Xaa = beta-Alanine

```
<400> SEQUENCE: 82

Lys Thr Arg Thr Lys Phe Leu Lys Lys Thr Xaa Xaa
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 10
<223> OTHER INFORMATION: Xaa = 6-aminohexanoic acid
<220> FEATURE:
<221> NAME/KEY: MOD_RES
<222> LOCATION: 11
<223> OTHER INFORMATION: Xaa = beta-Alanine

<400> SEQUENCE: 83

Lys Phe Phe Lys Phe Phe Lys Phe Phe Xaa Xaa
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 11
<223> OTHER INFORMATION: Xaa = 6-aminohexanoic acid
<220> FEATURE:
<221> NAME/KEY: MOD_RES
<222> LOCATION: 12
<223> OTHER INFORMATION: Xaa = beta-Alanine

<400> SEQUENCE: 84

Lys Phe Phe Lys Phe Phe Lys Phe Phe Lys Xaa Xaa
1               5                   10

<210> SEQ ID NO 85
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 7
<223> OTHER INFORMATION: Xaa = 6-aminohexanoic acid
<220> FEATURE:
<221> NAME/KEY: MOD_RES
<222> LOCATION: 8
<223> OTHER INFORMATION: Xaa = beta-Alanine

<400> SEQUENCE: 85

Arg Phe Phe Arg Phe Phe Xaa Xaa
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 8
<223> OTHER INFORMATION: Xaa = 6-aminohexanoic acid
```

```
<220> FEATURE:
<221> NAME/KEY: MOD_RES
<222> LOCATION: 9
<223> OTHER INFORMATION: Xaa = beta-Alanine

<400> SEQUENCE: 86

Arg Phe Phe Arg Phe Phe Arg Xaa Xaa
1               5

<210> SEQ ID NO 87
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 2, 3, 5, 6, 8, 9
<223> OTHER INFORMATION: Xaa = 6-aminohexanoic acid
<220> FEATURE:
<221> NAME/KEY: MOD_RES
<222> LOCATION: 10
<223> OTHER INFORMATION: Xaa = beta-Alanine

<400> SEQUENCE: 87

Arg Xaa Xaa Arg Xaa Xaa Arg Xaa Xaa Xaa
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 10
<223> OTHER INFORMATION: Xaa = 6-aminohexanoic acid
<220> FEATURE:
<221> NAME/KEY: MOD_RES
<222> LOCATION: 11
<223> OTHER INFORMATION: Xaa = beta-Alanine
<220> FEATURE:
<221> NAME/KEY: VARIANT
<222> LOCATION: (11)..(11)
<223> OTHER INFORMATION: amino acid conjugated to cttcgatagtg nucleotide
      sequence

<400> SEQUENCE: 88

Arg Phe Phe Arg Phe Phe Arg Phe Phe Xaa Xaa
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 11
<223> OTHER INFORMATION: Xaa = 6-aminohexanoic acid
<220> FEATURE:
<221> NAME/KEY: MOD_RES
<222> LOCATION: 12
<223> OTHER INFORMATION: Xaa = beta-Alanine
<220> FEATURE:
<221> NAME/KEY: VARIANT
<222> LOCATION: (12)..(12)
<223> OTHER INFORMATION: amino acid conjugated to cttcgatagtg nucleotide
      sequence

<400> SEQUENCE: 89
```

-continued

Arg Thr Arg Thr Arg Phe Leu Arg Arg Thr Xaa Xaa
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 11
<223> OTHER INFORMATION: Xaa = 6-aminohexanoic acid
<220> FEATURE:
<221> NAME/KEY: MOD_RES
<222> LOCATION: 12
<223> OTHER INFORMATION: Xaa = beta-Alanine
<220> FEATURE:
<221> NAME/KEY: VARIANT
<222> LOCATION: (12)..(12)
<223> OTHER INFORMATION: amino acid conjugated to cttcgatagtg nucleotide
      sequence

<400> SEQUENCE: 90

Arg Phe Phe Arg Phe Phe Arg Phe Phe Arg Xaa Xaa
1               5                   10

<210> SEQ ID NO 91
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 7
<223> OTHER INFORMATION: Xaa = 6-aminohexanoic acid
<220> FEATURE:
<221> NAME/KEY: MOD_RES
<222> LOCATION: 8
<223> OTHER INFORMATION: Xaa = beta-Alanine
<220> FEATURE:
<221> NAME/KEY: VARIANT
<222> LOCATION: (8)..(8)
<223> OTHER INFORMATION: amino acid conjugated to cttcgatagtg nucleotide
      sequence

<400> SEQUENCE: 91

Arg Phe Phe Arg Phe Phe Xaa Xaa
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 8
<223> OTHER INFORMATION: Xaa = 6-aminohexanoic acid
<220> FEATURE:
<221> NAME/KEY: MOD_RES
<222> LOCATION: 9
<223> OTHER INFORMATION: Xaa = beta-Alanine
<220> FEATURE:
<221> NAME/KEY: VARIANT
<222> LOCATION: (9)..(9)
<223> OTHER INFORMATION: amino acid conjugated to cttcgatagtg nucleotide
      sequence

<400> SEQUENCE: 92

Arg Phe Phe Arg Phe Phe Arg Xaa Xaa
1               5

```
<210> SEQ ID NO 93
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 2, 3, 5, 6, 8, 9
<223> OTHER INFORMATION: Xaa = 6-aminohexanoic acid
<220> FEATURE:
<221> NAME/KEY: MOD_RES
<222> LOCATION: 10
<223> OTHER INFORMATION: Xaa = beta-Alanine
<220> FEATURE:
<221> NAME/KEY: VARIANT
<222> LOCATION: (10)..(10)
<223> OTHER INFORMATION: amino acid conjugated to cttcgatagtg nucleotide
      sequence

<400> SEQUENCE: 93

Arg Xaa Xaa Arg Xaa Xaa Arg Xaa Xaa Xaa
1               5                   10

<210> SEQ ID NO 94
<211> LENGTH: 11
<212> TYPE: DNA
<213> ORGANISM: Artificial Sequence
<220> FEATURE:
<223> OTHER INFORMATION: Synthetic Oligomer

<400> SEQUENCE: 94
tgctcatact c                                                          11

<210> SEQ ID NO 95
<211> LENGTH: 11
<212> TYPE: DNA
<213> ORGANISM: Artificial Sequence
<220> FEATURE:
<223> OTHER INFORMATION: Synthetic Oligomer

<400> SEQUENCE: 95
atagtgctca t                                                          11

<210> SEQ ID NO 96
<211> LENGTH: 11
<212> TYPE: DNA
<213> ORGANISM: Artificial Sequence
<220> FEATURE:
<223> OTHER INFORMATION: Synthetic Oligomer

<400> SEQUENCE: 96
gcgttcttcc g                                                          11

<210> SEQ ID NO 97
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 2, 5, 8, 11, 13
<223> OTHER INFORMATION: Xaa = 6-aminohexanoic acid
<220> FEATURE:
<221> NAME/KEY: MOD_RES
<222> LOCATION: 14
<223> OTHER INFORMATION: Xaa = beta-Alanine

<400> SEQUENCE: 97
```

-continued

Arg Xaa Arg Arg Xaa Arg Arg Xaa Arg Arg Xaa Arg Xaa Xaa
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 2, 5, 8, 11, 13
<223> OTHER INFORMATION: Xaa = 6-aminohexanoic acid
<220> FEATURE:
<221> NAME/KEY: MOD_RES
<222> LOCATION: 14
<223> OTHER INFORMATION: Xaa = beta-Alanine
<220> FEATURE:
<221> NAME/KEY: VARIANT
<222> LOCATION: (14)..(14)
<223> OTHER INFORMATION: Xaa = amino acid conjugated to cttcgatagtg
      nucleotide sequence

<400> SEQUENCE: 98

Arg Xaa Arg Arg Xaa Arg Arg Xaa Arg Arg Xaa Arg Xaa Xaa
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 3, 6, 9, 12
<223> OTHER INFORMATION: Xaa = 6-aminohexanoic acid
<220> FEATURE:
<221> NAME/KEY: MOD_RES
<222> LOCATION: 13
<223> OTHER INFORMATION: Xaa = beta-Alanine

<400> SEQUENCE: 99

Arg Arg Xaa Arg Arg Xaa Arg Arg Xaa Arg Arg Xaa Xaa
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 2, 5, 8, 11, 13
<223> OTHER INFORMATION: Xaa = 6-aminohexanoic acid
<220> FEATURE:
<221> NAME/KEY: MOD_RES
<222> LOCATION: 14
<223> OTHER INFORMATION: Xaa = beta-Alanine

<400> SEQUENCE: 100

Arg Xaa Arg Arg Xaa Arg Arg Xaa Arg Arg Xaa Arg Xaa Xaa
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Synthetic Peptide
<220> FEATURE:

```
<221> NAME/KEY: MOD_RES
<222> LOCATION: 1, 4, 7, 10, 13
<223> OTHER INFORMATION: Xaa = 6-aminohexanoic acid
<220> FEATURE:
<221> NAME/KEY: MOD_RES
<222> LOCATION: 14
<223> OTHER INFORMATION: Xaa = beta-Alanine

<400> SEQUENCE: 101

Xaa Arg Arg Xaa Arg Arg Xaa Arg Arg Xaa Arg Arg Xaa Xaa
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 2, 4, 6, 8, 10, 12
<223> OTHER INFORMATION: Xaa = 6-aminohexanoic acid
<220> FEATURE:
<221> NAME/KEY: MOD_RES
<222> LOCATION: 13
<223> OTHER INFORMATION: Xaa = beta-Alanine

<400> SEQUENCE: 102

Arg Xaa Arg Xaa Arg Xaa Arg Xaa Arg Xaa Arg Xaa Xaa
1               5                   10

<210> SEQ ID NO 103
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 2, 4, 6, 8, 10, 12, 14
<223> OTHER INFORMATION: Xaa = 6-aminohexanoic acid
<220> FEATURE:
<221> NAME/KEY: MOD_RES
<222> LOCATION: 15
<223> OTHER INFORMATION: Xaa = beta-Alanine

<400> SEQUENCE: 103

Arg Xaa Arg Xaa Arg Xaa Arg Xaa Arg Xaa Arg Xaa Arg Xaa Xaa
1               5                   10                  15

<210> SEQ ID NO 104
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 2, 5, 8, 10
<223> OTHER INFORMATION: Xaa = 6-aminohexanoic acid
<220> FEATURE:
<221> NAME/KEY: MOD_RES
<222> LOCATION: 11
<223> OTHER INFORMATION: Xaa = beta-Alanine

<400> SEQUENCE: 104

Arg Xaa Arg Arg Xaa Arg Arg Xaa Arg Xaa Xaa
1               5                   10

<210> SEQ ID NO 105
<211> LENGTH: 14
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 2, 8, 13
<223> OTHER INFORMATION: Xaa = 6-aminohexanoic acid
<220> FEATURE:
<221> NAME/KEY: MOD_RES
<222> LOCATION: 5, 11, 14
<223> OTHER INFORMATION: Xaa = beta-Alanine

<400> SEQUENCE: 105

Arg Xaa Arg Arg Xaa Arg Arg Xaa Arg Arg Xaa Arg Xaa Xaa
1               5                   10

<210> SEQ ID NO 106
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 8, 16
<223> OTHER INFORMATION: Xaa = 6-aminohexanoic acid
<220> FEATURE:
<221> NAME/KEY: MOD_RES
<222> LOCATION: 2, 4, 6, 10, 12, 14, 17
<223> OTHER INFORMATION: Xaa = beta-Alanine

<400> SEQUENCE: 106

Arg Xaa Arg Xaa Arg Xaa Arg Xaa Arg Xaa Arg Xaa Arg Xaa Arg Xaa
1               5                   10                  15

Xaa

<210> SEQ ID NO 107
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 107
gtgctcatgg tgcacggtc                                               19

<210> SEQ ID NO 108
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 108
gccatggttt tttctcagg                                               19

<210> SEQ ID NO 109
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 109
tgggtatgtt gtagccat                                                18

<210> SEQ ID NO 110
<211> LENGTH: 20
<212> TYPE: DNA
```

```
<213> ORGANISM: Artificial Sequence
<220> FEATURE:
<223> OTHER INFORMATION: Synthetic Oligomer

<400> SEQUENCE: 110
cctgcccttt gttctagttg                                              20

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 111
ctgggatgag atccatcact                                              20
```